United States Patent
Zhao et al.

(10) Patent No.: US 9,427,442 B2
(45) Date of Patent: *Aug. 30, 2016

(54) FLUOROALKYL AND FLUOROCYCLOALKYL 1,4-BENZODIAZEPINONE COMPOUNDS

(71) Applicant: BRISTOL-MYERS SQUIBB COMPANY, Princeton, NJ (US)

(72) Inventors: Yufen Zhao, Pennington, NJ (US); Ashvinikumar V. Gavai, Princeton Junction, NJ (US); Patrice Gill, Levittown, PA (US); Soong-Hoon Kim, Titusville, NJ (US); Brian E. Fink, Yardley, PA (US); Libing Chen, Newtown, PA (US); Mark G. Saulnier, Higganum, CT (US); Wen-Ching Han, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/429,958

(22) PCT Filed: Sep. 20, 2013

(86) PCT No.: PCT/US2013/060841
§ 371 (c)(1),
(2) Date: Mar. 20, 2015

(87) PCT Pub. No.: WO2014/047397
PCT Pub. Date: Mar. 27, 2014

(65) Prior Publication Data
US 2015/0231152 A1    Aug. 20, 2015

Related U.S. Application Data

(60) Provisional application No. 61/703,937, filed on Sep. 21, 2012.

(51) Int. Cl.
*C07D 243/24*  (2006.01)
*A61K 31/5513*  (2006.01)
*A61K 45/06*  (2006.01)

(52) U.S. Cl.
CPC .......... *A61K 31/5513* (2013.01); *A61K 45/06* (2013.01); *C07D 243/24* (2013.01)

(58) Field of Classification Search
CPC .................................................. C07D 243/24
See application file for complete search history.

(56) References Cited

U.S. PATENT DOCUMENTS 4,981,847  A    1/1991  Sato et al.
5,322,842  A    6/1994  Sato et al.

(Continued)

FOREIGN PATENT DOCUMENTS

EP    0669334    8/1995
WO    WO 97/36879    10/1997

(Continued)

OTHER PUBLICATIONS

U.S. Appl. No. 14/627,573, filed Feb. 20, 2015, Gavai et al.

(Continued)

*Primary Examiner* — Bruck Kifle
(74) *Attorney, Agent, or Firm* — Gary D. Greenblatt

(57) ABSTRACT

Disclosed are compounds of Formula (I): (Formula (I)) wherein: $R_1$ is —$CH_2CH_2CF_3$; $R_2$ is —$CH_2CH_2CH_2F$, —$CH_2CF_2CH_3$, —$CH_2CH_2CF_3$, —$CH_2CH(CH_3)CF_3$, —$CH_2CH_2CF_2CH_3$, (Formulae (II), (III), (IV), (V) or (VI): $R_3$ is H or —$CH_3$; Ring A is phenyl or pyridinyl; and $R_x$, $R_y$, $R_a$, $R_b$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

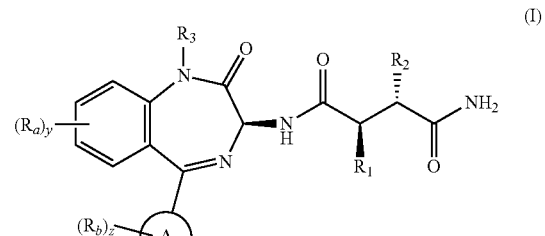

(I)

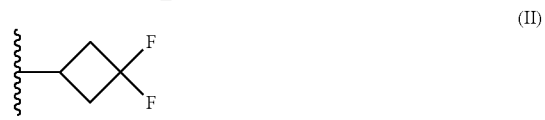

(II)

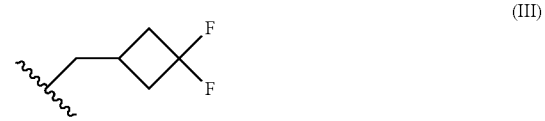

(III)

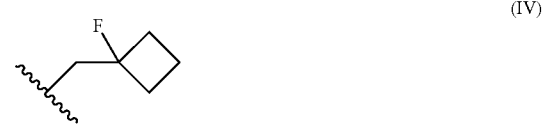

(IV)

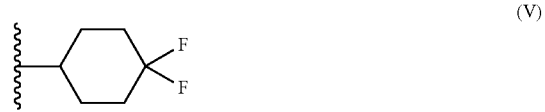

(V)

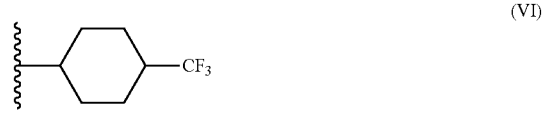

(VI)

7 Claims, No Drawings

(56) References Cited

U.S. PATENT DOCUMENTS

| | | |
|---|---|---|
| 5,324,726 A | 6/1994 | Bock et al. |
| 5,852,010 A | 12/1998 | Graham et al. |
| 5,998,407 A | 12/1999 | Graham et al. |
| 6,331,408 B1 | 12/2001 | Zaczek et al. |
| 6,495,540 B2 | 12/2002 | Thompson |
| 6,503,901 B1 | 1/2003 | Thompson et al. |
| 6,503,902 B2 | 1/2003 | Olson et al. |
| 6,509,333 B2 | 1/2003 | Olson |
| 6,525,044 B2 | 2/2003 | Olson et al. |
| 6,544,978 B2 | 4/2003 | Wu et al. |
| 6,632,812 B2 | 10/2003 | Han et al. |
| 6,653,303 B1 | 11/2003 | Wu et al. |
| 6,713,476 B2 | 3/2004 | Yang et al. |
| 6,737,038 B1 | 5/2004 | Zaczek et al. |
| 6,756,511 B2 | 6/2004 | Castro Pineiro et al. |
| 6,759,404 B2 | 7/2004 | Olson et al. |
| 6,794,381 B1 | 9/2004 | Olson et al. |
| 6,878,363 B2 | 4/2005 | Zaczek et al. |
| 6,900,199 B2 | 5/2005 | Han et al. |
| 6,958,329 B2 | 10/2005 | Olson |
| 6,960,576 B2 | 11/2005 | Olson et al. |
| 6,962,913 B2 | 11/2005 | Olson et al. |
| 6,984,626 B2 | 1/2006 | Nadin et al. |
| 7,001,901 B2 | 2/2006 | Yang |
| 7,053,081 B2 | 5/2006 | Olson et al. |
| 7,053,084 B1 | 5/2006 | Olson |
| 7,101,870 B2 | 9/2006 | Olson et al. |
| 7,105,509 B2 | 9/2006 | Castro Pineiro et al. |
| 7,112,583 B2 | 9/2006 | Olson et al. |
| 7,125,866 B1 | 10/2006 | Glick et al. |
| 7,153,491 B2 | 12/2006 | Zaczek et al. |
| 7,160,875 B2 | 1/2007 | Flohr et al. |
| 7,276,495 B2 | 10/2007 | Han et al. |
| 7,276,496 B2 | 10/2007 | Olson et al. |
| 7,304,049 B2 | 12/2007 | Olson |
| 7,304,055 B2 | 12/2007 | Olson et al. |
| 7,304,056 B2 | 12/2007 | Olson et al. |
| 7,342,008 B2 | 3/2008 | Olson et al. |
| 7,354,914 B2 | 4/2008 | Olson |
| 7,375,099 B2 | 5/2008 | Galley et al. |
| 7,390,802 B2 | 6/2008 | Han et al. |
| 7,390,896 B2 | 6/2008 | Olson et al. |
| 7,423,033 B2 | 9/2008 | Olson et al. |
| 7,456,172 B2 | 11/2008 | Olson |
| 7,456,278 B2 | 11/2008 | Olson |
| 7,498,324 B2 | 3/2009 | Han et al. |
| 7,528,249 B2 | 5/2009 | Olson et al. |
| 7,544,679 B2 | 6/2009 | Flohr et al. |
| 7,582,624 B2 | 9/2009 | Carter et al. |
| 7,655,647 B2 | 2/2010 | Han et al. |
| 7,718,795 B2 | 5/2010 | Olson |
| 8,629,136 B2 | 1/2014 | Gavai et al. |
| 8,822,454 B2 | 9/2014 | Gavai et al. |
| 8,999,918 B2 | 4/2015 | Gavai et al. |
| 2007/0185094 A1 | 8/2007 | Lattmann et al. |
| 2009/0181944 A1 | 7/2009 | Boylan et al. |
| 2014/0357605 A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047374 | 3/2014 |
| WO | WO 2014/047390 | 3/2014 |
| WO | WO 2014/047391 | 3/2014 |
| WO | WO 2014/047392 | 3/2014 |
| WO | WO 2014/047393 | 3/2014 |

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

Seiffert, D., et al., "Presenilin-1 and -2 Are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): A gamma-secretase inhibitor with A beta lowering activity in a transgenic mouse model of Alzheimer's disease," Bioorganic & Medicinal Chemistry Letters 17 pp. 4006-4011 (2007).

Jun, H.T., et al., "Top NOTCH Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060841 International Search Report mailed Nov. 7, 2013.

PCT/US2013/060841 Preliminary Report on Patentability mailed Apr. 2, 2015.

FLUOROALKYL AND FLUOROCYCLOALKYL 1,4-BENZODIAZEPINONE COMPOUNDS

This application is a national phase application under 35 U.S.C. §371 of International Patent Application No. PCT/US2013/060841, filed Sep. 20, 2013, which claims priority to U.S. Provisional Application 61/703,937, filed Sep. 21, 2012, which are expressly incorporated fully herein by reference.

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell*, 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing bis(fluoroalkyl)1,4-benzodiazepinone compounds that are useful as selective inhibitors of Notch signaling pathway.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds are Notch inhibitors that may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the present invention provides at least one compound of Formula (I):

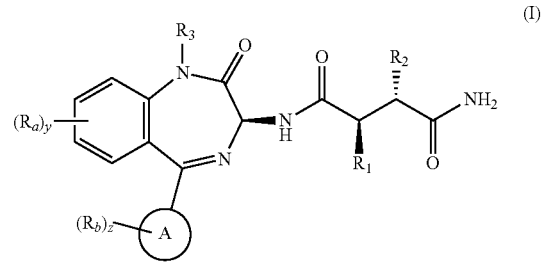

or at least one prodrug thereof, wherein:
$R_1$ is —$CH_2CH_2CF_3$;
$R_2$ is —$CH_2CH_2CH_2F$, —$CH_2CF_2CH_3$, —$CH_2CH_2CF_3$, —$CH_2CH(CH_3)CF_3$, —$CH_2CH_2CF_2CH_3$,

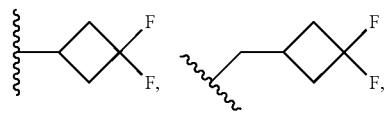

-continued

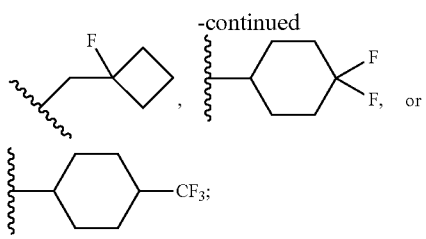

R$_3$ is H or —CH$_3$;
Ring A is phenyl or pyridinyl;
each R$_a$ is independently F, Cl, —CN, —OH, —CH$_3$, cyclopropyl, —CF$_3$, —OCH$_3$, —OCF$_3$, and/or —O(cyclopropyl);
each R$_b$ is independently F, Cl, —CH$_3$, —CF$_3$, —CN, and/or —OCH$_3$;
y is zero, 1, or 2; and
z is zero, 1, or 2;
provided that one and only one of R$_1$ and R$_2$ is —CH$_2$CH$_2$CF$_3$.

One embodiment provides at least one compound of Formula (I) wherein Ring A is phenyl; and R$_1$, R$_2$, R$_3$, R$_a$, R$_b$, y, and z are defined in the first aspect. Included in this embodiment are compounds in which R$_3$ is H. Also included in this embodiment are compounds in which R$_3$ is H and z is 1 or 2.

One embodiment provides at least one compound of Formula (I) wherein Ring A is pyridinyl; and R$_1$, R$_2$, R$_3$, R$_a$, R$_b$, y, and z are defined in the first aspect. Included in this embodiment are compounds in which R$_3$ is H. Also included in this embodiment are compounds in which R$_3$ is H and z is 1 or 2.

One embodiment provides at least one compound of Formula (I) wherein R$_2$ is —CH$_2$CH$_2$CH$_2$F, —CH$_2$CF$_2$CH$_3$, —CH$_2$CH$_2$CF$_3$, —CH$_2$CH(CH$_3$)CF$_3$, or —CH$_2$CH$_2$CF$_2$CH$_3$; and R$_1$, R$_3$, Ring A, R$_a$, R$_b$, y, and z are defined in the first aspect. Included in this embodiment are compounds in which Ring A is phenyl. Also included in this embodiment are compounds in which Ring A is phenyl and R$_3$ is H.

One embodiment provides at least one compound of Formula (I) wherein R$_2$ is

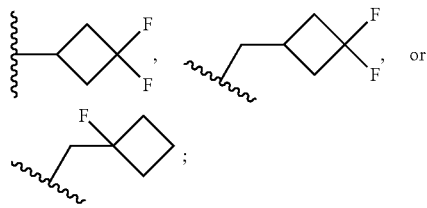

and R$_1$, R$_3$, Ring A, R$_a$, R$_b$, y, and z are defined in the first aspect. Included in this embodiment are compounds in which Ring A is phenyl. Also included in this embodiment are compounds in which Ring A is phenyl and R$_3$ is H.

One embodiment provides at least one compound of Formula (I) wherein R$_2$ is

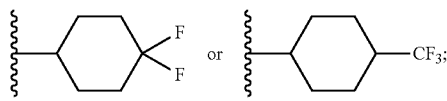

and R$_1$, R$_3$, Ring A, R$_a$, R$_b$, y, and z are defined in the first aspect. Included in this embodiment are compounds in which Ring A is phenyl. Also included in this embodiment are compounds in which Ring A is phenyl and R$_3$ is H.

One embodiment provides at least one compound of Formula (I) wherein R$_3$ is H; and R$_1$, R$_2$, Ring A, R$_a$, R$_b$, y, and z are defined in the first aspect. Included in this embodiment are compounds in which R$_3$ is deuterium (D) or tritium (T). Also included in this embodiment are compounds in which Ring A is phenyl.

One embodiment provides a compound of Formula (I) wherein R$_3$ is —CH$_3$; and R$_1$, R$_2$, R$_a$, R$_b$, y, and z are defined in the first aspect. R$_3$ includes methyl groups in which one or more hydrogen atoms are isotopically substituted with deuterium (D) and/or tritium (T). In one example of this embodiment, R$_3$ is —CD$_3$. Also included in this embodiment are compounds in which Ring A is phenyl.

One embodiment provides at least one compound of Formula (I) wherein y is 1, and R$_1$, R$_2$, R$_3$, Ring A, R$_x$, R$_y$, R$_a$, R$_b$, and z are defined in the first aspect. Included in the embodiment are compounds in which Ring A is phenyl. Also included in this embodiment are compounds in which Ring A is phenyl and z is zero or 1.

One embodiment provides at least one compound of Formula (I) wherein R$_3$ is H; Ring A is phenyl; each R$_a$ is independently F, Cl, —CH$_3$, cyclopropyl, —OCH$_3$, and/or —O(cyclopropyl); R$_b$ is F or —CH$_3$; z is zero or 1; and R$_1$, R$_2$, and y are defined in the first aspect.

One embodiment provides at least one compound of Formula (I) having the structure:

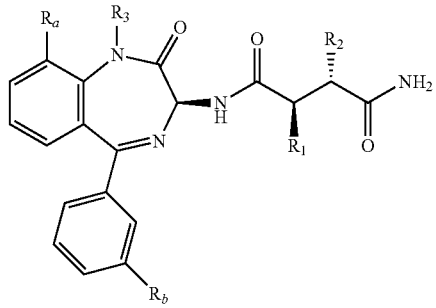

wherein R$_1$, R$_2$, R$_3$, R$_a$, and R$_b$ are defined in the first aspect. Included in this embodiment are compounds in which R$_a$ is F, Cl, —CH$_3$, —OCH$_3$, cyclopropyl, or —O(cyclopropyl); and R$_b$ is F or —CH$_3$. Also included in this embodiment are compounds in which R$_a$ is F or —CH$_3$; and R$_b$ is F or —CH$_3$.

One embodiment provides at least one compound of Formula (I) having the structure:

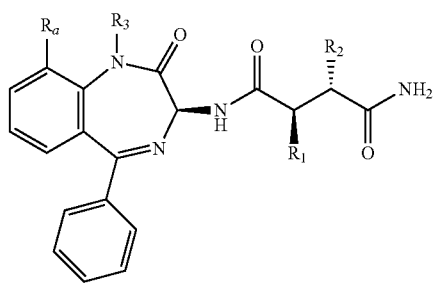

wherein R₁, R₂, R₃, and Rₐ are defined in the first aspect. Included in this embodiment are compounds in which Rₐ is F, Cl, —CH₃, —OCH₃, cyclopropyl, or —O(cyclopropyl). Also included in this embodiment are compounds in which Rₐ is F, Cl, or —CH₃.

One embodiment provides a compound of Formula (I) selected from: (2R,3S)-3-((3,3-difluorocyclobutyl)methyl)-N-((3S)-9-methyl-2-oxo-5-phenyl-2,3-dihydro-1H-1,4-benzodiazepin-3-yl)-2-(3,3,3-trifluoropropyl)succinamide (1); (2R,3S)-3-(4,4-difluorocyclohexyl)-N-((3S)-9-methoxy-2-oxo-5-phenyl-2,3-dihydro-1H-1,4-benzodiazepin-3-yl)-2-(3,3,3-trifluoropropyl)succinamide (2); (2R,3S)—N-((3S)-9-(cyclopropyloxy)-5-(3-fluorophenyl)-2-oxo-2,3-dihydro-1H-1,4-benzodiazepin-3-yl)-3-(4,4-difluorocyclohexyl)-2-(3,3,3-trifluoropropyl)succinamide (3); (2R,3S)—N-((3S)-9-chloro-2-oxo-5-phenyl-2,3-dihydro-1H-1,4-benzodiazepin-3-yl)-3-(4-(trifluoromethyl)cyclohexyl)-2-(3,3,3-trifluoropropyl)succinamide (4); (2R,3S)—N-((3S)-9-chloro-2-oxo-5-phenyl-2,3-dihydro-1H-1,4-benzodiazepin-3-yl)-3-(4,4-difluorocyclohexyl)-2-(3,3,3-trifluoropropyl)succinamide (5); (2R,3S)-3-((3,3-difluorocyclobutyl)-N-((3S)-2-oxo-5-phenyl-2,3-dihydro-1H-1,4-benzodiazepin-3-yl)-2-(3,3,3-trifluoropropyl) succinamide (6); (2R,3S)—N-((3S)-9-(cyclopropyloxy)-2-oxo-5-phenyl-2,3-dihydro-1H-1,4-benzodiazepin-3-yl)-3-((3,3-difluorocyclobutyl)methyl)-2-(3,3,3-trifluoropropyl)succinamide (7); (2R,3S)-3-((3,3-difluorocyclobutyl)methyl)-N-((3S)-9-methoxy-2-oxo-5-phenyl-2,3-dihydro-1H-1,4-benzodiazepin-3-yl)-2-(3,3,3-trifluoropropyl)succinamide (8); (2R,3S)-3-((3,3-difluorocyclobutyl)methyl)-N-((3S)-5-(3-fluorophenyl)-9-methyl-2-oxo-2,3-dihydro-1H-1,4-benzodiazepin-3-yl)-2-(3,3,3-trifluoropropyl)succinamide (9); (2R,3S)—N-((3S)-9-chloro-5-(3-methylphenyl)-2-oxo-2,3-dihydro-1H-1,4-benzodiazepin-3-yl)-3-((3,3-difluorocyclobutyl)methyl)-2-(3,3,3-trifluoropropyl)succinamide (10); (2R,3S)-3-((3,3-difluorocyclobutyl)methyl)-N-((3S)-9-fluoro-5-(3-methylphenyl)-2-oxo-2,3-dihydro-1H-1,4-benzodiazepin-3-yl)-2-(3,3,3-trifluoropropyl)succinamide (11); (2R,3S)—N-((3S)-9-cyclopropyl-2-oxo-5-phenyl-2,3-dihydro-1H-1,4-benzodiazepin-3-yl)-3-((3,3-difluorocyclobutyl)methyl)-2-(3,3,3-trifluoropropyl)succinamide (12); (2R,3S)—N-((3S)-9-chloro-2-oxo-5-phenyl-2,3-dihydro-1H-1,4-benzodiazepin-3-yl)-3-((3,3-difluorocyclobutyl)methyl)-2-(3,3,3-trifluoropropyl)succinamide (13); (2R,3S)-3-((3,3-difluorocyclobutyl)methyl)-N-((3S)-9-fluoro-2-oxo-5-phenyl-2,3-dihydro-1H-1,4-benzodiazepin-3-yl)-2-(3,3,3-trifluoropropyl)succinamide (14); (2R,3S)-3-((3,3-difluorocyclobutyl)methyl)-N-((3S)-2-oxo-5-phenyl-2,3-dihydro-1H-1,4-benzodiazepin-3-yl)-2-(3,3,3-trifluoropropyl)succinamide (15); (2R,3S)-3-(3-fluoropropyl)-N-((3S)-9-methoxy-2-oxo-5-phenyl-2,3-dihydro-1H-1,4-benzodiazepin-3-yl)-2-(3,3,3-trifluoropropyl)succinamide (16); (2R,3S)-3-(3-fluoropropyl)-N-((3S)-8-methoxy-2-oxo-5-phenyl-2,3-dihydro-1H-1,4-benzodiazepin-3-yl)-2-(3,3,3-trifluoropropyl)succinamide (17); (2R,3S)-3-(2,2-difluoropropyl)-N-((3S)-2-oxo-5-phenyl-2,3-dihydro-1H-1,4-benzodiazepin-3-yl)-2-(3,3,3-trifluoropropyl)succinamide (18); (2R,3S)—N-((3S)-9-fluoro-2-oxo-5-phenyl-2,3-dihydro-1H-1,4-benzodiazepin-3-yl)-3-((2S)-3,3,3-trifluoro-2-methylpropyl)-2-(3,3,3-trifluoropropyl)succinamide (19); (2R,3S)—N-((3S)-9-chloro-2-oxo-5-phenyl-2,3-dihydro-1H-1,4-benzodiazepin-3-yl)-3-(3-fluoropropyl)-2-(3,3,3-trifluoropropyl)succinamide (20); (2R,3S)-3-((3,3-difluorobutyl)-N-((3S)-9-methoxy-2-oxo-5-phenyl-2,3-dihydro-1H-1,4-benzodiazepin-3-yl)-2-(3,3,3-trifluoropropyl)succinamide (21); (2R,3S)—N-((3S)-9-chloro-2-oxo-5-phenyl-2,3-dihydro-1H-1,4-benzodiazepin-3-yl)-3-((2R)-3,3,3-trifluoro-2-methylpropyl)-2-(3,3,3-trifluoropropyl)succinamide (22); (2R,3S)—N-((3S)-9-chloro-2-oxo-5-phenyl-2,3-dihydro-1H-1,4-benzodiazepin-3-yl)-3-((2S)-3,3,3-trifluoro-2-methylpropyl)-2-(3,3,3-trifluoropropyl)succinamide (23); (2R,3S)—N-((3S)-9-chloro-2-oxo-5-phenyl-2,3-dihydro-1H-1,4-benzodiazepin-3-yl)-3-((3,3-difluorobutyl)-2-(3,3,3-trifluoropropyl)succinamide (24); and (2R,3S)-3-((1-fluorocyclobutyl)methyl)-N-((3S)-9-methyl-2-oxo-5-phenyl-2,3-dihydro-1H-1,4-benzodiazepin-3-yl)-2-(3,3,3-trifluoropropyl)succinamide (25).

One embodiment provides at least one compound of Formula (I) having a metabolic half life value of at least 45 minutes as measured in the human metabolic stability half-life assay described herein.

One embodiment provides at least one compound of Formula (I) having a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen", as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Any compound that can be converted in vivo to provide the bioactive agent (i.e., the compound of Formula (I)) is a prodrug within the scope and spirit of the invention.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising at least one compound of Formula (I); and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), or a prodrug thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof at least one compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I) in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment at least one compound of Formula (I) for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I); and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including $IGFR_1$ inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of one at least one compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I); and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I); administering dasatinib; and optionally, one or more additional anticancer agents.

In one embodiment, a method is provided for treating cancer comprising administering to a mammal in need thereof at least one compound of Formula (I); administering paclitaxel; and optionally, one or more additional anticancer agents.

In one embodiment, a method is provided for treating cancer comprising administering to a mammal in need thereof at least one compound of Formula (I); administering tamoxifen; and optionally, one or more additional anticancer agents.

In one embodiment, a method is provided for treating cancer comprising administering to a mammal in need thereof at least one compound of Formula (I); administering a glucocorticoid; and optionally, one or more additional anticancer agents. An example of a suitable glucocorticoid is dexamethasone.

In one embodiment, a method is provided for treating cancer comprising administering to a mammal in need thereof at least one compound of Formula (I); administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I); one or more additional agents selected from a kinase inhibitory agent (small molecule, polypeptide, and antibody), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week;

administration in cycles (e.g., daily administration for two to eight consecutive weeks followed by a rest period with no administration for up to one week); or administration on alternate days.

In one embodiment, at least one compound of Formula (I) is administered continuously to a patient in need thereof, one or more times daily. For example, a therapeutically effective amount of the compound of Formula (I) is administered to a patient in need thereof, one or more times daily for continuous days.

In one embodiment, at least one compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, at least one compound of Formula (I) is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, at least one compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) is administered on one day, followed by 6 days of rest, and repeated on a weekly schedule.

In one embodiment, at least one compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) is administered on two consecutive days, followed by 5 days of rest, and repeated on a weekly schedule.

In one embodiment, at least one compound of Formula (I) is administered on three consecutive days followed by four days of rest, and repeated on a weekly schedule.

In one embodiment, at least one compound of Formula (I) is administered on one day, followed by 10 to 13 days of rest.

In one embodiment, at least one compound of Formula (I) is administered once each day (QD). This embodiment includes once daily oral administration.

In one embodiment, at least one compound of Formula (I) is administered twice each day (BID). This embodiment includes twice daily oral administration.

In one embodiment, at least one compound of Formula (I) is administered on alternate days: one day on followed by one day of rest. This two day cycle can be repeated one or more times.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 7.

Scheme 1

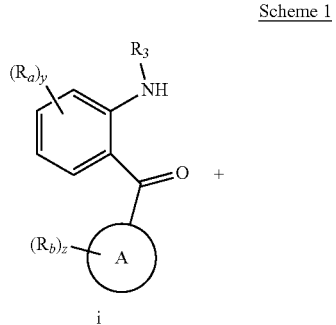

The preparation of benzodiazepinone (iv) may be accomplished in multitude of methods known to one skilled in the art. For example, as shown in Scheme 1, an appropriately substituted 2-aminobenzophenone (i) (for example, from Walsh, D. A., *Synthesis*, 677 (1980); and references cited therein, or other methods known to one skilled in the art) may be coupled to the protected glycine derivative (ii) (PG=protecting group, for example PG=CBz, see Katritzky, A. R. et al., *J. Org. Chem.*, 55:2206-2214 (1990)), treated with a reagent such as ammonia and subjected to cyclization to afford the benzodiazepinone (iii), according to the procedure outlined in the literature (for example Sherrill, R. G. et al., *J. Org. Chem.*, 60:730 (1995); or other routes known to one skilled in the art). The resulting racemic mixture may be separated (using procedures known to one skilled in the art) to afford the individual enantiomers, or used as a racemate. Also, if $R_3$ is H, (iii) may be, for example, treated with a reagent such as MeI and a base such as $K_2CO_3$ in a solvent such as DMF to prepare $R_3$ is methyl.

Step 2: The deprotection of (iii) may be accomplished in several ways known to one skilled in the art. For example, with PG=CBz, Compound (iii) may be treated with a reagent such as HBr in a solvent such as AcOH. Compound (iv) may be used as a racemate. Alternatively, compound (iv) may be subjected to enantiomeric resolution using standard methods (e.g., chiral preparative chromatography).

Scheme 2

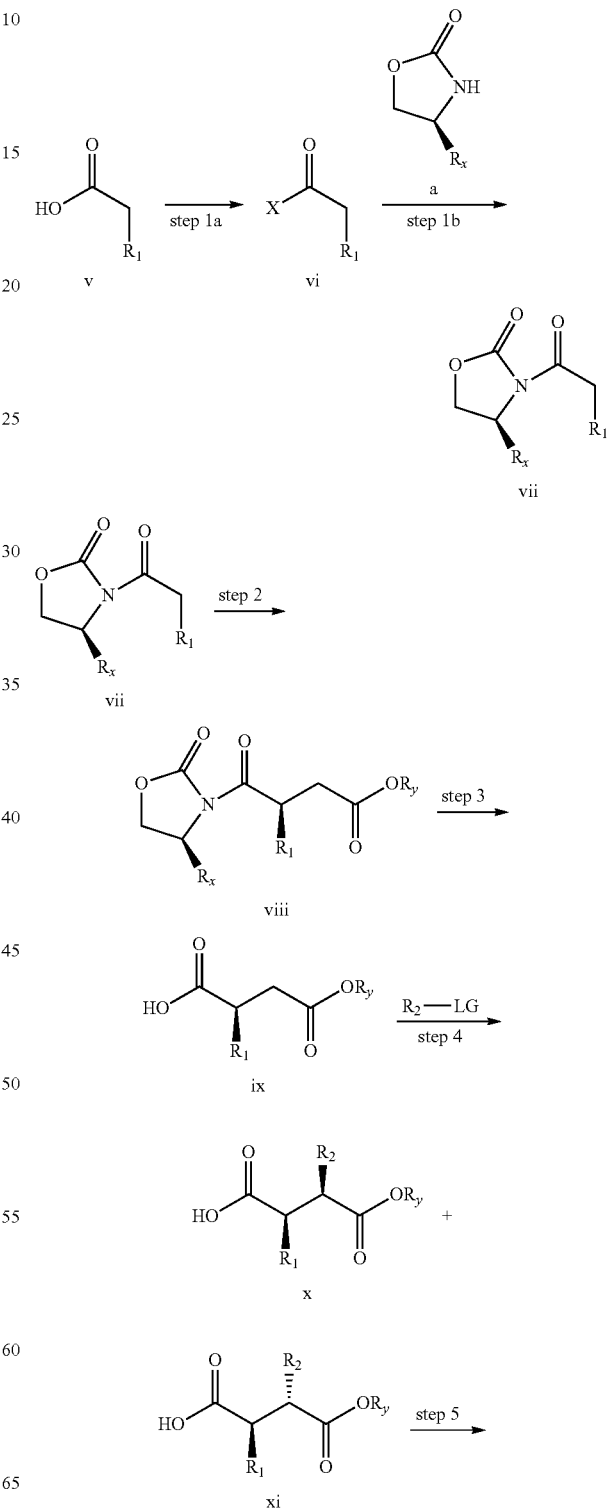

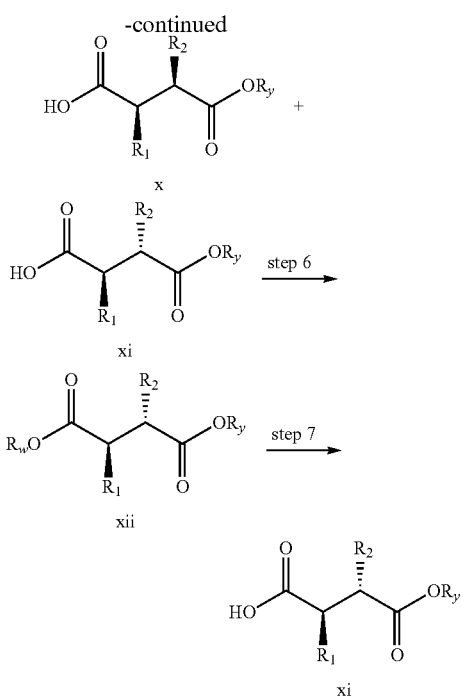

Compound (xii) in Scheme 2 may be prepared by a synthetic sequence outlined in Scheme 2.

Step 1: Acid (v) can be converted to compound (vii) in multiple ways known to one skilled in the art. For example, treatment of acid (v) with a reagent such as oxalyl chloride in a solvent such as DCM gives the acid chloride (vi). Compound (vi) can be treated with an oxazolidinone (a) under standard conditions to give compound (vii) (Evans, D. A. et al., *J. Am. Chem. Soc.*, 112:4011 (1990)).

Step 2: The second step of Scheme 2 is accomplished by treating compound (vii) with a base such as sodium bis(trimethylsilyl)-amide or lithium diisopropyl amide in a solvent such as THF at low temperature such as −78° C. under an inert atmosphere. The resulting enolate of (vii) is treated with a reagent such as tert-butyl bromoacetate to provide compound (viii), $R_y$=t-Butyl).

Step 3: Conversion of compound (viii) to (ix) may be accomplished by treating compound (viii) with hydrogen peroxide and lithium hydroxide at an appropriate temperature using a mixture of solvents such as THF/water.

Step 4: Compound (ix) may be converted to a mixture of compound (x) and compound (xi) by generating the enolate of (ix) with a base such as LDA in a solvent such as THF at low temperature such as −78° C. under an inert atmosphere and further treatment with a reagent ($R_2$-LG) bearing an appropriate leaving group (e.g., LG=triflate). The resulting mixture of diastereomers (x/xi) may then be utilized in subsequent synthetic steps.

Step 5: Alternately, the mixture (x/xi) may be subjected to epimerization conditions, for example by treatment with LDA and diethylaluminum chloride followed by quenching with methanol or acetic acid to enrich the desired diastereomer. The resulting diastereomerically enriched mixture of compound (x/xi) may then be utilized in subsequent synthetic steps or the mixture of diastereoisomers may be separated if desired, employing suitable conditions such as preparative HPLC, preparative chiral HPLC or silica gel chromatography, and the resulting pure desired diastereoisomer (xi) used in the subsequent steps.

Step 6: Alternatively, the mixture of diastereomeric acids (x) and (xi) may be protected by treatment with, for example, benzyl bromide in the presence of a base such as $K_2CO_3$ in a solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xii) used in the subsequent step.

Step 7: The last step of Scheme 2 is a deprotection step and may be accomplished in several ways known to one skilled in the art. For example, for $R_w$=benzyl in compound (xii), treatment under hydrogenation conditions using a catalyst such as palladium on carbon in a solvent such as MeOH under a hydrogen atmosphere may provide compound (xi) that may subsequently be utilized.

Alternatively, compound (xi) may be prepared according to the sequence of steps found in Scheme 3.

Scheme 3

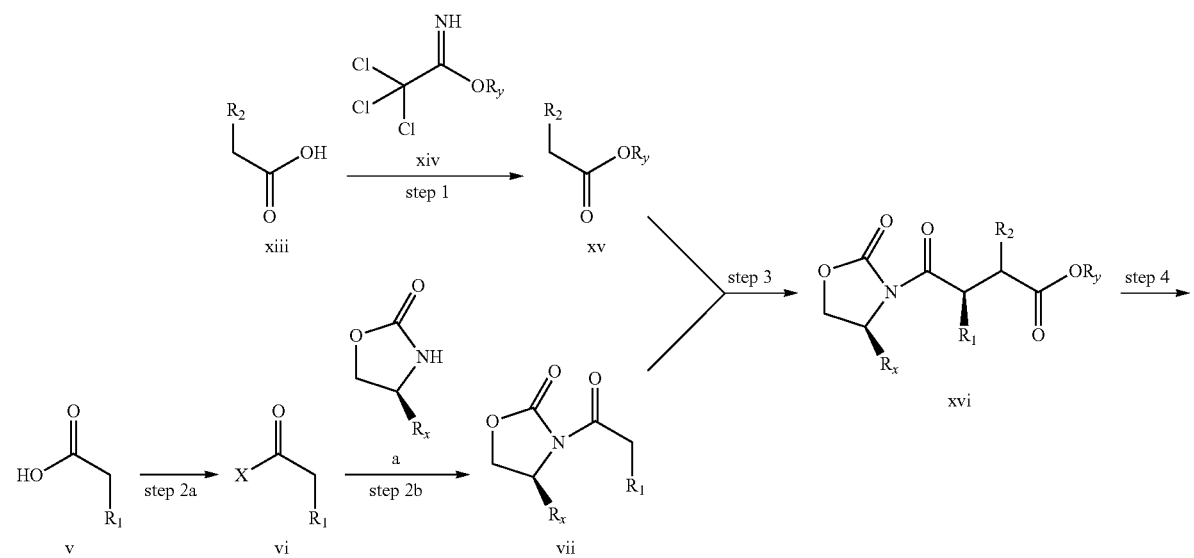

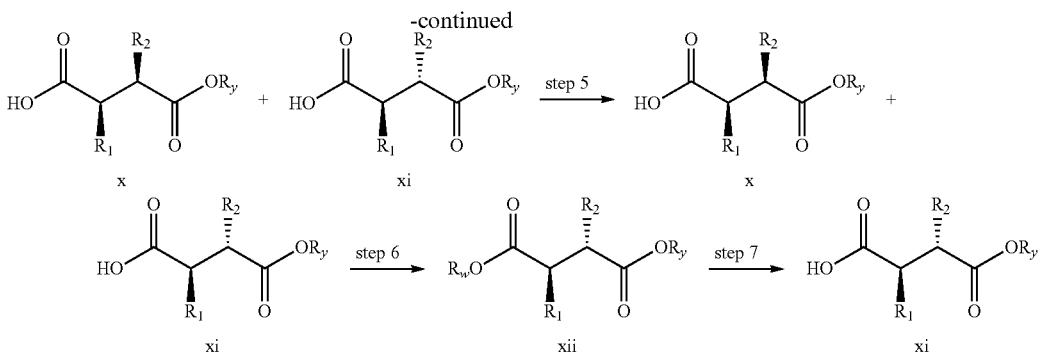

Step 1: The first step of Scheme 3 is accomplished by converting compound (xiii) to an ester (xv), employing one of the multiple ways known to one skilled in the art, such as treatment with a substituted acetimidate such as compound (xiv) in the presence of a reagent such as boron trifluoride etherate at an appropriate temperature in a solvent such as THF.

Step 2: Acid (v) can be converted to compound (vi) in multiple ways known to one skilled in the art. For example, treatment of acid (v) with a reagent such as oxalyl chloride in a solvent such as DCM gives the acid chloride (vi). Compound (vi) can be treated with an oxazolidinone (a) under standard conditions to give compound (vii) (Evans, D. A. et al., *J. Am. Chem. Soc.*, 112:4011 (1990)).

Step 3: Compound (vii) can be converted to a mixture of diastereomers (xvi) in multiple ways (Baran, P. et al., *J. Am. Chem. Soc.*, 130(34):11546 (2008)). For example, compound (xv) is treated with a base such as LDA in a solvent such as toluene, at low temperature such as –78° C. under an inert atmosphere such as $N_2$. The resulting mixture is added to a solution of compound (vii) treated with lithium chloride and a base such as LDA in a solvent such as toluene under an inert atmosphere such as $N_2$. To the resulting mixture of the enolates of compounds (xv) and (vii) is added bis(2-ethylhexanoyloxy) copper at a low temperature such as –78° C. under an inert atmosphere such as $N_2$ and warmed to room temperature to provide compound (xvi).

Step 4: Conversion of compound (xvi) to a mixture of compound (x) and compound (xi) may be accomplished by treating it with hydrogen peroxide and lithium hydroxide at an appropriate temperature using a mixture of solvents such as THF/water. The resulting mixture of diastereomers may then be utilized in subsequent synthetic steps. If necessary, the resulting mixture of diastereomers may be separated at this point via silica gel chromatography or preparative HPLC.

Step 5: Alternately, the mixture (x/xi) may be subjected to epimerization conditions, for example by treatment with LDA and diethylaluminum chloride followed by quenching with methanol or acetic acid to enrich the desired diastereomer. The resulting diastereomerically enriched mixture of compound may then be utilized in subsequent synthetic steps or the mixture of diastereoisomers may be separated if desired, employing suitable conditions such as preparative HPLC, preparative chiral HPLC or silica gel chromatography, and the resulting pure desired diastereoisomer (xi) used in the subsequent steps.

Step 6: Alternatively, the mixture of diastereomeric acids (x) and (xi) may be protected by treatment with, for example, benzyl bromide in the presence of a base such as $K_2CO_3$ in a solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xii) used in the subsequent steps.

Step 7: The last step of Scheme 3 is a deprotection step and may be accomplished in several ways known to one skilled in the art. For example, for $R_w$=benzyl in compound (xii), treatment under hydrogenation conditions using a catalyst such as palladium on carbon in a solvent such as MeOH under a hydrogen atmosphere may provide compound (xi) that may subsequently be utilized, for example, in step 1 of Scheme 4.

Scheme 4

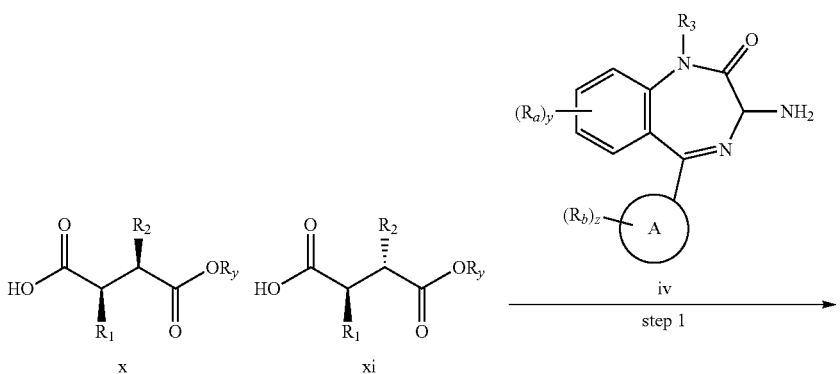

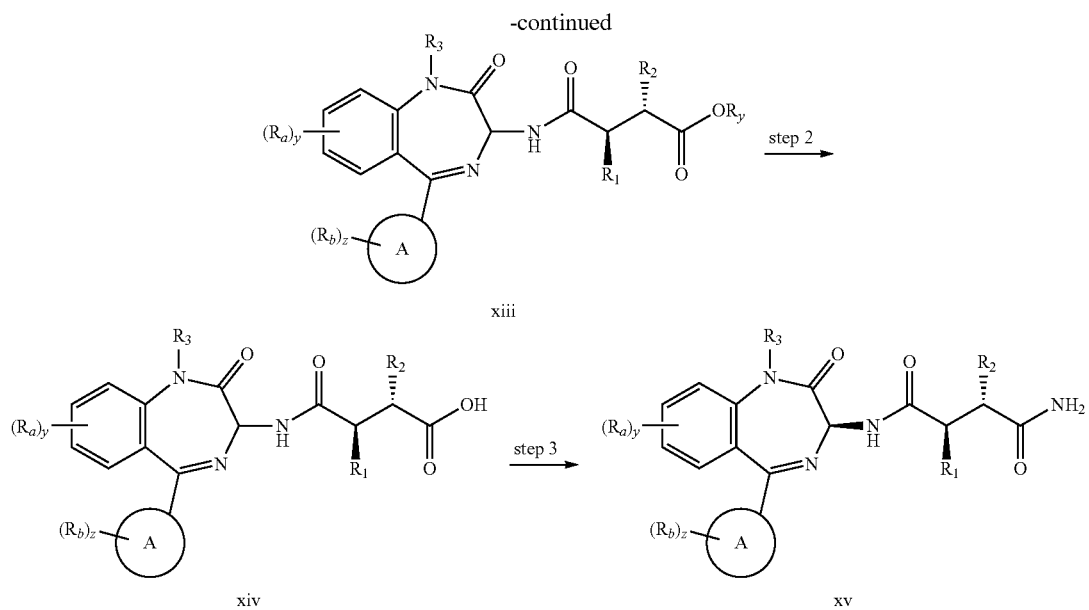

Step 1: Compounds of structure (iv) may be coupled to either pure diastereomer compound (xi) or a diastereomeric mixture of compounds (x/xi) in the presence of a coupling reagent such as TBTU and a base such as TEA, in a solvent such as DMF to provide compound (xiii) as either a diastereomerically pure compound or as a mixture of diastereoisomers, as appropriate, depending on the enantiomeric and/or diastereomeric purity of the coupling partners. This mixture may be used as such in the subsequent step, or if desired, may be purified using an appropriate separation technique, such as chiral preparative chromatography to provide the diastereomerically pure compounds.

Step 2: Treatment of compound (xiii) with an acid such as TFA at an appropriate temperature such as 0° C., in a solvent such as DCM provides compound (xiv) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 3: Conversion of compound (xiv) to compound (xv, $R_4$=H) may be accomplished via coupling of compound (xiv) with an appropriate amine source such as ammonium chloride or ammonia, a carbodiimide such as EDC, HOBT and a base such as TEA in a solvent such as DMF. If necessary the diastereomeric mixture can be separated using an appropriate separation technique, such as chiral preparative chromatography.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

AcOH acetic acid
$AlMe_3$ trimethyl aluminum
Bn benzyl
Boc tert-butoxycarbonyl
$Boc_2O$ di-tert-butyl dicarbonate
CBz benzyloxycarbonyl
DCC 1,3-dicyclohexylcarbodiimide
DCM dichloromethane
DMAP dimethylaminopyridine
DME dimethyl ether
DMF dimethylformamide
DMSO dimethyl sulfoxide
EDC 1-(3-dimethylaminopropyl)-3-ethylcarbodiimide hydrochloride
$Et_3N$ triethyl amine
$Et_2O$ diethyl ether
EtOH ethanol
EtOAc ethyl acetate
equiv. equivalence
g gram
h hour(s)
HOBt hydroxybenzotriazole
HPLC high pressure liquid chromatography
KOtBu potassium tert-butoxide
LCMS Liquid Chromatography-Mass Spectroscopy
LDA lithium diisopropylamide
LiHMDS lithium bis(trimethylsilyl)amide
MeI methyl iodide
MeOH methanol
min minute(s)
mL milliliter
mmol millimolar
NaHMDS sodium bis(trimethylsilyl)amide
n-BuLi n-butyl lithium
$NH_4Oac$ ammonium acetate
$Pd(OAc)_2$ palladium acetate
RT retention time
t-Bu tertiary butyl
tBuOH tertiary butyl alcohol tBuOMe tert-butyl methyl ether
TBTU O-(1H-benzotriazol-1-yl)-N,N,N',N'-tetramethyluronium tetrafluoroborate
TEA triethylamine
TFA trifluoroacetic acid
THF tetrahydrofuran Intermediate S-1: (R)-2-((S)-1-(tert-Butoxy)-3-((3,3-difluorocyclobutyl)-1-oxopropan-2-yl)-5,5,5-trifluoropentanoic acid

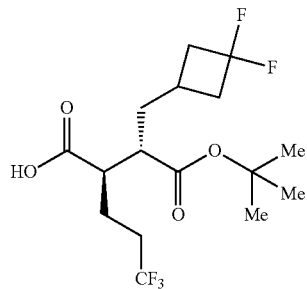

(S-1)

Intermediate S-1A: Diethyl 2-((2,2-dichloro-3-oxocyclobutyl)methyl)malonate

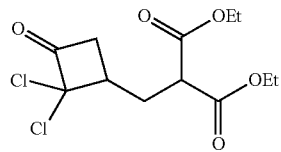

(S-1A)

To a stirred suspension of Cu.Zn (1.771 g, 13.73 mmol) and diethyl 2-allylmalonate (1.084 mL, 5.49 mmol) in anhydrous Et₂O (20 mL) at reflux was added a solution of phosphorus oxychloride (1.127 mL, 12.09 mmol) and 2,2,2-trichloroacetyl chloride (1.357 mL, 12.09 mmol) in Et₂O (10 mL) dropwise through an addition funnel over 2 h. The resulting mixture was then heated at reflux overnight. After cooling to room temperature, the mixture was filtered through CELITE® and washed with EtOAc. The filtrate was concentrated and the residue was purified by silica gel column chromatography (80 g, EtOAc/hexane=0-50%) to afford Intermediate S-1A (1.59 g, 93%). $^1$H NMR (400 MHz, chloroform-d) δ 4.32-4.23 (m, 4H), 3.58 (dd, J=8.9, 6.1 Hz, 1H), 3.47-3.32 (m, 1H), 3.16-2.92 (m, 2H), 2.51 (ddd, J=14.3, 7.2, 6.1 Hz, 1H), 2.40-2.25 (m, 1H), 1.36-1.30 (m, 6H).

Intermediate S-1B: Diethyl 2-((3-oxocyclobutyl)methyl)malonate

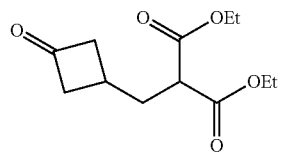

(S-1B)

To a vigorously stirred mixture of zinc (10.42 g, 159 mmol) in acetic acid (50 mL) at 0° C. was added a solution of Intermediate S-1A (12.4 g, 39.9 mmol) in acetic acid (50 mL) dropwise. The mixture was then heated to 60° C. overnight. After cooling to room temperature, the reaction mixture was poured into ice-water and extracted with EtOAc. The organic layer was washed with water, saturated aqueous NaHCO₃ and brine, and then dried and concentrated. The residue was purified by silica gel column chromatography (220 g column, EtOAc/hexane=0-40%) to afford Intermediate S-1B (6.91 g, 71.6%). $^1$H NMR (400 MHz, chloroform-d) δ 4.29-4.19 (m, 4H), 3.35 (t, J=7.5 Hz, 1H), 3.25-3.12 (m, 2H), 2.82-2.71 (m, 2H), 2.53-2.38 (m, 1H), 2.24 (t, J=7.6 Hz, 2H), 1.33-1.28 (m, 6H).

Intermediate S-1C: Diethyl 2-((3,3-difluorocyclobutyl)methyl)malonate

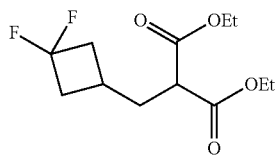

(S-1C)

To a solution of Intermediate S-1B (6.9 g, 28.5 mmol) in DCM (100 mL) at 0° C. was added DAST (12 mL, 91 mmol) dropwise. The mixture was stirred at room temperature overnight. After cooling to 0° C., saturated aqueous NaHCO₃ was carefully added. The mixture was stirred for 30 min until bubbling ceased. The organic layer was separated, dried and concentrated. The residue was purified by silica gel column chromatography (80 g column, EtOAc/hexane=0-20%) to afford Intermediate S-1C (6.48 g, 86%). $^1$H NMR (400 MHz, chloroform-d) δ 4.27-4.16 (m, 4H), 3.28 (t, J=7.3 Hz, 1H), 2.79-2.61 (m, 2H), 2.30-2.07 (m, 5H), 1.33-1.26 (m, 6H).

Intermediate S-1D: 2-((3,3-Difluorocyclobutyl)methyl)malonic acid

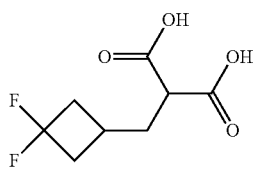

(S-1D)

To a solution of Intermediate S-1C (6.48 g, 24.52 mmol) in EtOH (25 mL) was added 4 N NaOH (25 mL, 100 mmol). The mixture was heated to reflux at 100° C. for 2 h. After cooling to room temperature, the mixture was concentrated to about half of the volume. The residue was then extracted with ether, and the ether layer was back extracted with some water. The combined aqueous layers were acidified with conc. HCl, and extracted with EtOAc. The combined extracts were dried over MgSO₄, filtered and concentrated. The crude residue was sonicated with hexane, and the solid precipitate was collected by filtration, rinsed with hexane, and dried to afford Intermediate S-1D (4.86 g, 95%). $^1$H NMR (400 MHz, DMSO-d₆) δ 12.75 (br. s., 1H), 3.18 (t, J=7.4 Hz, 1H), 2.69-2.53 (m, 2H), 2.33-2.14 (m, 2H), 2.14-1.99 (m, 1H), 1.95-1.85 (m, 2H).

Intermediate S-1E: 3-(3,3-Difluorocyclobutyl)propanoic acid

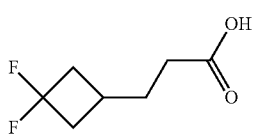

Intermediate S-1D (4.86 g, 23.35 mmol), in a 30 mL closed vial equipped with a balloon was heated at 160° C. for 1 h. The reaction mixture was cooled to room temperature to afford Intermediate S-1E (3.8 g, 99%). MS(ES):m/z=163 [M−H⁺]; ¹H NMR (400 MHz, DMSO-d₆) δ 12.10 (br. s., 1H), 2.73-2.54 (m, 2H), 2.29-2.00 (m, 5H), 1.69 (q, J=7.5 Hz, 2H).

Intermediate S-1F: tert-Butyl 3-(3,3-difluorocyclobutyl)propanoate

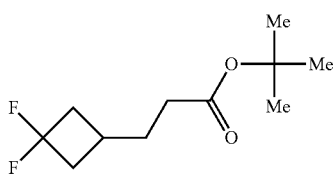

To a cool (0° C.), stirred solution of Intermediate S-1E (3.8 g, 23.15 mmol) in hexane (20 mL) and THF (20 mL) under N₂ was added tert-butyl 2,2,2-trichloroacetimidate (8.29 mL, 46.3 mmol) portionwise over 5 min and the reaction mixture was stirred for 15 min. Boron trifluoride ether complex (0.293 mL, 2.315 mmol) was added at 0° C. and the reaction mixture was allowed to warm to room temperature as the bath warmed and stirred overnight. To the clear reaction mixture was added NaHCO₃ (5 g) and stirring continued for 60 min. The suspension was filtered through MgSO₄, washed with 300 mL of hexane and the resulting solution was allowed to sit for several hours. The resulting solid was filtered through the same MgSO₄ filter, and washed with hexane (100 mL). The filtrate was concentrated and the crude material was purified by silica gel chromatography (120 g column) eluting with 100% hexane to 20% EtOAc in hexane to afford Intermediate S-1F (4.4 g, 19.98 mmol, 86% yield). ¹H NMR (400 MHz, chloroform-d) δ 2.85-2.53 (m, 2H), 2.31-2.08 (m, 5H), 1.80 (q, J=7.2 Hz, 2H), 1.47 (s, 9H).

Intermediate S-1G: (S)-4-Isopropyl-3-(5,5,5-trifluoropentanoyl)oxazolidin-2-one

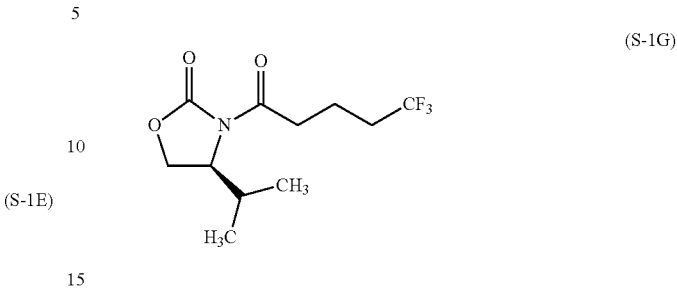

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min. The solution was stirred until all bubbling subsided. The reaction mixture was concentrated under reduced pressure to give a pale yellow oil. To a separate flask, charged with a solution of (4S)-4-(propan-2-yl)-1,3-oxazolidin-2-one (4.18 g, 32.4 mmol) in THF (100 mL) at −78° C. was added n-BuLi (13.0 mL, 32.5 mmol, 2.5M in hexane) dropwise via syringe over 5 min. After stirring for 10 min, the above acid chloride, dissolved in THF (20 mL), was added via cannula over 15 min. The reaction mixture was warmed to 0° C. and was allowed to warm to room temperature as the bath warmed and stirred overnight. To the reaction mixture was then added saturated NH₄Cl, and it was then extracted with EtOAc (2×). The combined organics were washed with brine, dried (Na₂SO₄), filtered and concentrated under reduced pressure. The crude material was purified by silica gel chromatography (hexanes/EtOAc) to provide Intermediate S-1G (7.39 g, 86%) as a colorless oil: ¹H NMR (400 MHz, CDCl₃) δ 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Intermediate S-1H: (2S,3R)-tert-Butyl 2-((3,3-difluorocyclobutyl)methyl)-6,6,6-trifluoro-3-(((S)-4-isopropyl-2-oxooxazolidine-3-carbonyl)hexanoate, and Intermediate S-1I: (2R,3R)-tert-Butyl 2-((3,3-difluorocyclobutyl)methyl)-6,6,6-trifluoro-3-((S)-4-isopropyl-2-oxooxazolidine-3-carbonyl)hexanoate

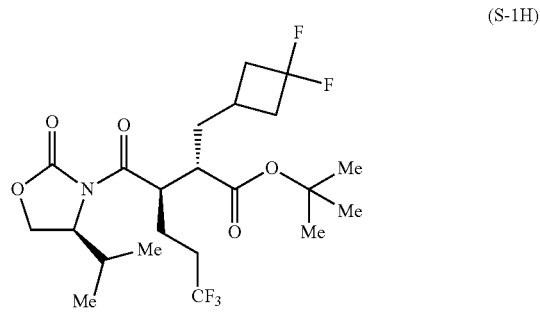

31
-continued (S-1I)

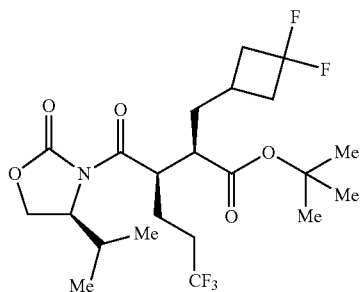

Diisopropylamine (3.01 mL, 21.11 mmol) was dissolved in 28.8 mL of THF and cooled to −78° C. nBuLi (1.6 M in hexane) (13.10 mL, 20.95 mmol) was added dropwise over a period of 5 minutes. After 5 minutes, the ~0.5 M LDA solution was kept at 0° C. In a separate flask, lithium chloride (1.221 g, 28.8 mmol) was dried in an oven overnight, and then under high vacuum while heating with a heat gun and then cooled under nitrogen. Intermediate S-1G (1.4 g, 5.24 mmol), having been azeotroped once with toluene, was transferred (under nitrogen) with toluene (10 mL) to the flask containing LiCl, and then cooled to −78° C. Intermediate S-1F (2.077 g, 9.43 mmol), having been azeotroped once with toluene, was dissolved in toluene (10 mL) and cooled to −78° C. The solution of LDA (13.1 mL of a 0.5 M LDA solution) was added dropwise to the LiCl/oxazolidinone (1.4 g, 5.24 mmol) solution at −78° C. over a period of 5 minutes. The reaction mixture was stirred at −78° C. for 15 minutes, and then at 0° C. for 10 minutes and then cooled to −78° C. A solution of LDA (23.6 mL of a 0.5 M LDA solution) was added dropwise to the solution of Intermediate S-1F and stirred at −78° C. for 30 minutes. This solution was then added via cannula (fast negative pressure, all added within 30 seconds) to the LiCl/oxazolidone solution at −78° C. After 1 minute following the transfer, solid bis((2-ethylhexanoyl)oxy)copper (5.50 g, 15.72 mmol), having been dried in an oven overnight, was added at −78° C., and the flask was transferred to a 40° C. water bath and swirled for 15 minutes. The reaction was quenched with 5% NH$_4$OH solution (30 mL saturated NH$_4$OH in 150 mL water), and extracted 2×100 mL with ethyl acetate. The combined extracts were washed with brine, dried and concentrated. The crude mixture was purified by silica gel chromatography (40 g column, EtOAc/hexane, 0-35%) to give a 1.3:1 mixture of Intermediates S-1H and S-1I (1.196 g, 47%).

Intermediate S-1: (R)-2-((S)-1-(tert-Butoxy)-3-((3,3-difluorocyclobutyl)-1-oxopropan-2-yl)-5,5,5-trifluoropentanoic acid, and Intermediate S-1J: (R)-2-((R)-1-(tert-Butoxy)-3-((3,3-difluorocyclobutyl)-1-oxopropan-2-yl)-5,5,5-trifluoropentanoic acid (S-1)

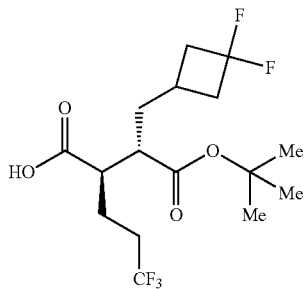

32
-continued (S-1J)

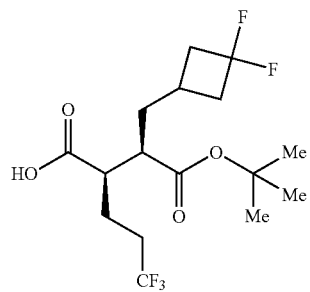

To an ice-water cooled solution of LiOH (0.176 g, 7.35 mmol) in water (7 mL) was added 50% H$_2$O$_2$ (1.502 mL, 24.51 mmol) dropwise. The resulting solution was added dropwise to a solution of a 1.3:1 mixture of S-1H and S-1I (1.85 g, 4.23 mmol) in THF (21 mL) at 0° C. The mixture was stirred at 0° C. and the warmed to room temperature over a weekend. The resulting mixture was treated with sat. aqueous NaHCO$_3$ (10 mL), followed by the slow addition of aqueous Na$_2$S$_2$O$_3$ (20 mL). The mixture was stirred for 1 h and then concentrated to remove the THF. To the aqueous layer was added 1N NaOH (4 mL), and the mixture was extracted with DCM. The aqueous layer was cooled in an ice-water bath and slowly acidified with conc. HCl to pH 3. The resulting mixture was saturated with solid NaCl and extracted with EtOAc. The combine extracts were washed with sat NaCl, dried with MgSO$_4$, filtered and concentrated to afford Intermediates S-1 and S-1J (1.19 g, as a diastereomer mixture of S-1J:S-1=1:1.3). (ES):m/z=373 [M−H$^+$].

Intermediate S-1: (R)-2-((S)-1-(tert-Butoxy)-3-((3,3-difluorocyclobutyl)-1-oxopropan-2-yl)-5,5,5-trifluoropentanoic acid, and Intermediate S-1J: (R)-2-((R)-1-(tert-Butoxy)-3-((3,3-difluorocyclobutyl)-1-oxopropan-2-yl)-5,5,5-trifluoropentanoic acid (S-1J)

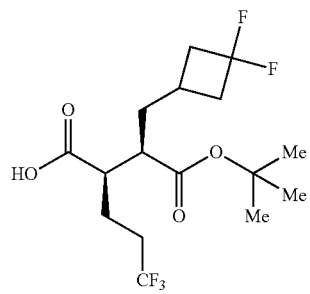

To a cold (−78° C.), stirred solution of a 1.3:1 mixture of Intermediate S-1: Intermediate S-1J (1.08 g, 2.89 mmol) in THF (16 mL) was added LDA (2.0M in THF/hexane/ethyl benzene, Aldrich) (3.5 mL, 7.00 mmol) dropwise via syringe over 5 min (internal temperature never exceeded −64° C., J-KEM® probe in reaction solution). The reaction mixture was stirred for 15 min, and then warmed to room temperature (24° C. water bath) and stirred for 15 min. The mixture was then cooled to −78° C. for 15 min. To the reaction mixture was added Et$_2$AlCl (1M in hexane, Aldrich) (7.2 mL, 7.20 mmol) via syringe (internal temperature never exceeded −55° C.) and stirred for 10 min, and then warmed to room temperature (24° C. bath) for 15 min. The mixture was then cooled back to −78° C. for 15 min. The reaction mixture was transferred via cannula over 5 min to a 250 mL RB flask charged with MeOH (26 mL, 643 mmol), pre-cooled to −78° C. with vigorous stirring. The flask was removed from the bath, ice was added followed by the slow addition of 1N HCl (26 mL, 26.0 mmol). The reaction mixture was allowed to warm to room temperature, during which the gas evolution subsided. The reaction mixture was diluted with EtOAc (250 mL), and the organic phase was separated. The organic phase was washed with a solution of potassium fluoride (1.51 g, 26.0 mmol) and 1N HCl (7.2 mL, 7.20 mmol) in water (50 mL, 2775 mmol), followed by brine, and then dried (Na$_2$SO$_4$) filtered and concentrated to dryness to afford a 12.3:1 (S-1:S-1J) mixture of diastereomers. The crude material was used in the next step without further purification.

Intermediate S-1K: (2R,3S)-1-Benzyl 4-tert-butyl 3-((3,3-difluorocyclobutyl)methyl)-2-(3,3,3-trifluoropropyl)succinate

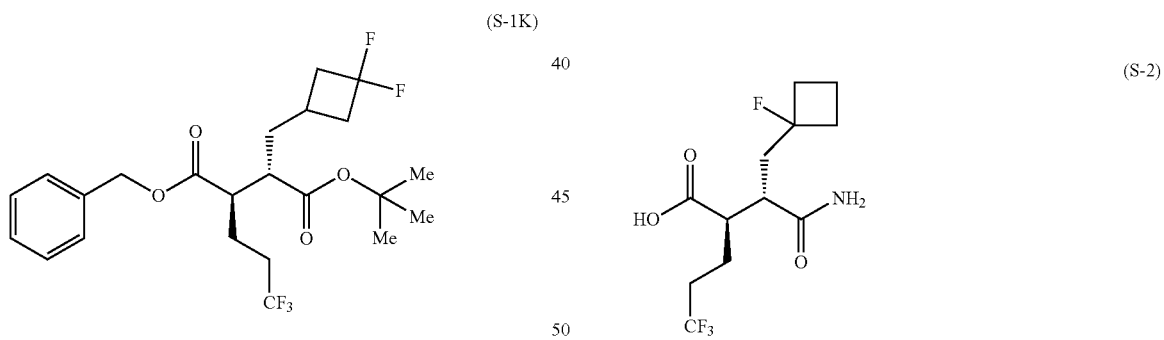

To a solution of the mixture of S-1 and S-1J (1.1 g, 2.94 mmol) from above in DMF (10 mL) was added K$_2$CO$_3$ (0.690 g, 5.00 mmol) and benzyl bromide (0.524 mL, 4.41 mmol). The mixture was stirred at room temperature overnight. Water (100 mL) was added and the mixture was extracted with EtOAc (2×100 mL). The combined extracts were washed with 10% LiCl (2×100 mL), then brine (100 mL) and dried (Na$_2$SO$_4$), filtered and concentrated to dryness. The crude mixture of diastereomers were separated by silica gel chromatography (SiO$_2$, 120 g column, 0% toluene/hexanes to 80% toluene/hexanes, 15 min. gradient) to afford Intermediate S-1K (0.89, 65%). $^1$H NMR (400 MHz, chloroform-d) δ 7.43-7.35 (m, 5H), 5.24-5.15 (m, 2H), 2.72-2.55 (m, 3H), 2.48 (td, J=10.2, 3.5 Hz, 1H), 2.17-1.95 (m, 5H), 1.93-1.81 (m, 2H), 1.79-1.69 (m, 1H), 1.46 (s, 9H), 1.37-1.28 (m, 1H).

Intermediate S-1: (R)-2-((S)-1-(tert-Butoxy)-3-((3,3-difluorocyclobutyl)-1-oxopropan-2-yl)-5,5,5-trifluoropentanoic acid

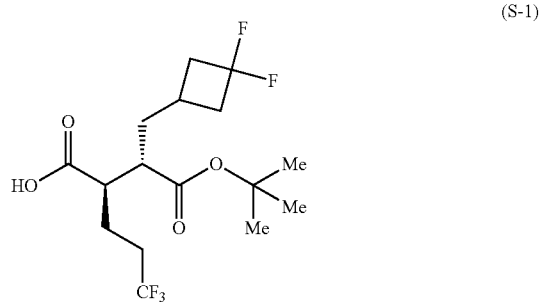 [SMILES: CC(C)(C)OC(=O)[C@@H](CC1CC(F)(F)C1)[C@@H](CCC(F)(F)F)C(=O)O]

A solution of Intermediate S-1K (870 mg, 1.873 mmol) in MeOH (37.500 ml) was treated with 10% palladium on carbon (100 mg, 0.940 mmol) under a nitrogen atmosphere. The reaction mixture was purged with nitrogen and then with H$_2$ gas. The reaction mixture was stirred under a hydrogen atmosphere at room temperature. After 4 hours the reaction mixture was filtered through a pad of CELITE® and the filter cake was washed with MeOH. The filtrate was concentrated to dryness to afford Intermediate S-1 (660 mg, 94%). $^1$H NMR (400 MHz, chloroform-d) δ 2.77-2.63 (m, 3H), 2.56 (ddd, J=10.3, 8.6, 3.7 Hz, 1H), 2.36-2.06 (m, 5H), 2.05-1.87 (m, 2H), 1.84-1.72 (m, 1H), 1.61-1.52 (m, 1H), 1.49 (s, 9H).

Intermediate S-2: (R)-2-((S)-1-Amino-3-(1-fluorocyclobutyl)-1-oxopropan-2-yl)-5,5,5-trifluoropentanoic acid

Intermediate S-2A: 1-Allylcyclobutanol (S-2A)

HO

To a solution of cyclobutanone (3.48 g, 49.7 mmol) in tetrahydrofuran (30 mL) at 0° C. was added 2.0 M allylmagnesium chloride (49.7 mL, 99 mmol) dropwise. The mixture was stirred at 0° C. for 1 h, and then at room temperature for 1 h. The reaction was quenched with saturated aqueous NH₄Cl, followed by 6N HCl. The residue was extracted with EtOAc. The combined extracts were washed with saturated aqueous NaHCO₃ and brine, and then dried and concentrated. The residue was purified by silica gel column chromatography (40 g column, EtOAc/hexane=0-50%) to afford Intermediate S-2A. (4.55 g, yield 81%). $^1$H NMR (400 MHz, chloroform-d) δ 5.98-5.82 (m, 1H), 5.26-5.14 (m, 2H), 2.40 (d, J=7.3 Hz, 2H), 2.14-2.04 (m, 4H), 1.92 (s, 1H), 1.84-1.71 (m, 1H), 1.63-1.48 (m, 1H).

Intermediate S-2B:
1-(3-Hydroxypropyl)cyclobutanol

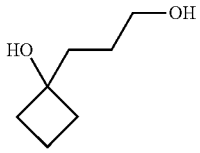

To a solution of Intermediate S-2A (0.92 g, 8.20 mmol) in THF (15 mL) was added 1.0 M borane tetrahydrofuran complex (16.40 mL, 16.40 mmol) dropwise and the solution was stirred at room temperature for 1 h. The mixture was cooled to 0° C., and 1N NaOH (15 mL) was added carefully, followed by 50% H₂O₂ (2 mL). The mixture was stirred at room temperature overnight and then concentrated to remove the THF. The residue was diluted with water and extracted with EtOAc. The combined extracts were washed with brine, dried and concentrated. The residue was purified by silica gel column chromatography (40 g column, EtOAc/hexane=50-100%) to afford Intermediate S-2B as a colorless oil (0.69 g, yield 65%). $^1$H NMR (400 MHz, chloroform-d) δ 3.72 (t, J=5.7 Hz, 1H), 2.59 (br. s., 1H), 2.35 (br. s., 1H), 2.16-1.97 (m, 2H), 1.84-1.67 (m, 2H), 1.62-1.47 (m, 1H).

Intermediate S-2C: 3-(1-Hydroxycyclobutyl)propyl benzoate

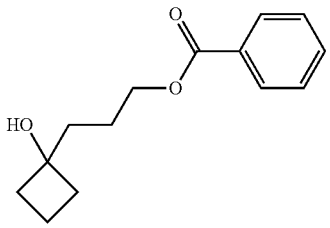

To a solution of Intermediate S-2B (0.69 g, 5.30 mmol) in DCM (15 mL) at 0° C. was added TEA (1.108 mL, 7.95 mmol), followed by a solution of benzoyl chloride (1.02 g, 7.25 mmol) in DCM (2 mL). The mixture was stirred at 0° C. for 2 h and then diluted with DCM, washed with water and brine, dried and concentrated. The residue was purified by silica gel column chromatography (24 g column, EtOAc/hexane=0-40%) to afford Intermediate S-2C (1.2 g, 97%). $^1$H NMR (400 MHz, chloroform-d) δ 8.11-8.05 (m, 2H), 7.62-7.56 (m, 1H), 7.51-7.44 (m, 2H), 4.41 (t, J=6.5 Hz, 2H), 2.18-1.99 (m, 4H), 1.97-1.87 (m, 2H), 1.86-1.75 (m, 2H), 1.60-1.55 (m, 2H).

Intermediate S-2D: 3-(1-Hydroxycyclobutyl)propyl benzoate

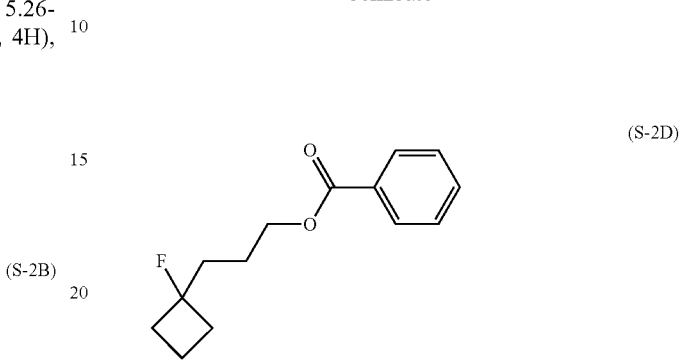

To a solution of Intermediate S-2C (12.75 g, 54.4 mmol) in DCM (150 mL) at 0° C. was added DAST (12.8 mL, 97 mmol). The mixture was stirred at room temperature for 3.5 h. Saturated NaHCO₃ was then added carefully, and the mixture was extracted with DCM. The combined extracts were washed with brine, dried and concentrated. The residue was purified by silica gel column chromatography (220 g column, EtOAc/hexane=0-25%) to afford Intermediate S-2D (9.6 g, 75%). $^1$H NMR (400 MHz, chloroform-d) δ 8.17-7.98 (m, 2H), 7.64-7.56 (m, 1H), 7.51-7.43 (m, 2H), 4.44-4.35 (m, 2H), 2.45-2.25 (m, 2H), 2.22-2.06 (m, 2H), 2.01-1.77 (m, 5H), 1.55-1.47 (m, 1H).

Intermediate S-2E:
3-(1-Fluorocyclobutyl)propan-1-ol

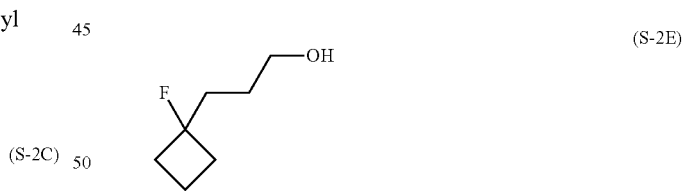

To a solution of Intermediate S-2D (9.6 g, 40.6 mmol) in THF (150 mL)/MeOH (150 mL) was added 1N NaOH (81 mL, 81 mmol). The mixture was stirred at room temperature for 4.5 h and then concentrated to about 30% original volume. The residue was extracted with EtOAc, and the combined extracts were washed with sat NaHCO₃ and brine, and then dried and concentrated. The residue was purified by silica gel column chromatography (120 g column, EtOAc/hexane=0-50%) to afford Intermediate S-2E (4.63 g, 86%). $^1$H NMR (400 MHz, chloroform-d) δ 3.72 (q, J=5.9 Hz, 2H), 2.44-2.22 (m, 2H), 2.18-2.05 (m, 2H), 1.92-1.76 (m, 3H), 1.76-1.66 (m, 2H), 1.55-1.46 (m, 1H), 1.38 (t, J=5.0 Hz, 1H).

Intermediate S-2F: 3-(1-Fluorocyclobutyl)propanoic acid

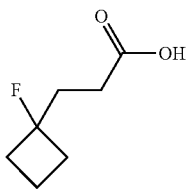

(S-2F)

To a solution of Intermediate S-2E (4.63 g, 35.0 mmol) in acetone (150 mL) was added Jones reagent (38.9 mL, 52.5 mmol). The mixture was stirred at room temperature for 2.5 h. The reaction mixture was then diluted with EtOAc and washed with 10% NaHSO$_3$. The aqueous layer was extracted with EtOAc and the combined extracts were washed with brine, dried over MgSO$_4$, filtered and concentrated to afford the crude acid, which was triturated with hexane to give Intermediate S-2F (4.28 g, 84%) $^1$H NMR (400 MHz, DMSO-d$_6$) δ 12.13 (s, 1H), 2.32-2.03 (m, 6H), 2.02-1.89 (m, 2H), 1.81-1.68 (m, 1H), 1.48 (dquind, J=11.1, 8.8, 2.4 Hz, 1H).

Intermediate S-2G: 3-(1-Fluorocyclobutyl)propanoic acid

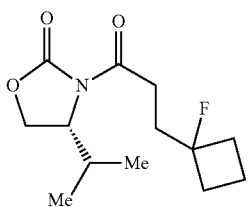

(S-2G)

Intermediate S-2G (2.22 g, 63%) was prepared from (R)-4-isopropyloxazolidin-2-one (1.944 g, 15.05 mmol) and Intermediate S-2F (2 g, 13.68 mmol) in a similar way as Intermediate S-1G. $^1$H NMR (400 MHz, chloroform-d) δ 4.46 (dt, J=8.4, 3.5 Hz, 1H), 4.33-4.27 (m, 1H), 4.26-4.21 (m, 1H), 3.07 (qdd, J=17.1, 9.1, 6.2 Hz, 2H), 2.47-2.26 (m, 3H), 2.23-2.03 (m, 4H), 1.92-1.78 (m, 1H), 1.56-1.46 (m, 1H), 0.97-0.88 (m, 6H).

Intermediate S-2H: tert-Butyl 5,5,5-trifluoropentanoate

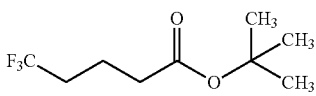

(S-2H)

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid NaHCO$_3$ (5 g) and stirred for 30 min. The mixture was filtered through MgSO$_4$ and washed with hexanes (200 mL). The solution was allowed to rest for 45 min, and the resulting solid material was removed by filtering on the same MgSO$_4$ filter again, washed with hexanes (100 mL) and concentrated under reduced pressure without heat. The volume was reduced to about 30 mL, filtered through a clean fritted funnel, washed with hexane (5 mL), and then concentrated under reduced pressure without heat. The resulting neat oil was filtered through a 0.45 µm nylon membrane filter disk to provide Intermediate S-2H (6.6 g, 31.4 mmol 98% yield) as a colorless oil: $^1$H NMR (400 MHz, CDCl$_3$) δ ppm 1.38 (s, 9H) 1.74-1.83 (m, 2H) 2.00-2.13 (m, 2H) 2.24 (t, J=7.28 Hz, 2H).

Intermediate S-2I: (R)-tert-Butyl 5,5,5-trifluoro-2-((S)-3-(1-fluorocyclobutyl)-1-((R)-4-isopropyl-2-oxooxazolidin-3-yl)-1-oxopropan-2-yl)pentanoate, and

Intermediate S-2J: (S)-tert-Butyl 5,5,5-trifluoro-2-((S)-3-(1-fluorocyclobutyl)-1-((R)-4-isopropyl-2-oxooxazolidin-3-yl)-1-oxopropan-2-yl)pentanoate

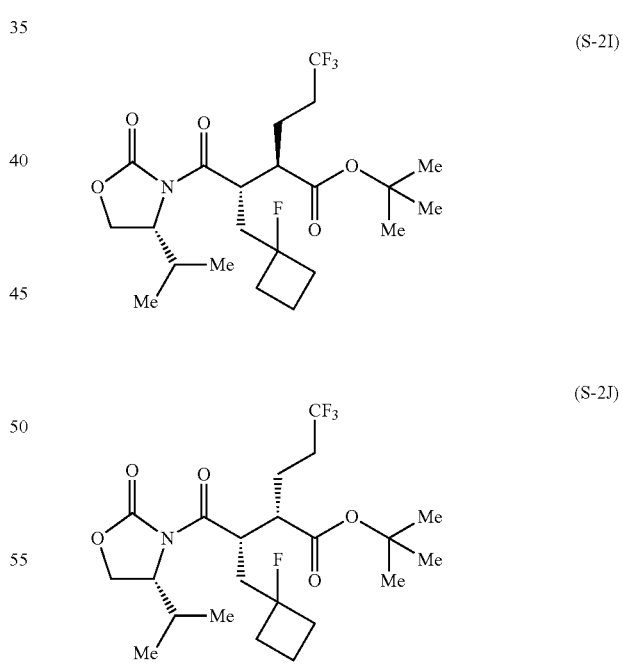

A 1.2:1 mixture of Intermediates S-2I:S-2J (1.03 g, 52%) was prepared from Intermediate S-2G (1.1 g, 4.28 mmol) and Intermediate S-2H (1.59 g, 7.48 mmol) in a similar way as Intermediate S-1H. HPLC: RT=3.200 min (H$_2$O/MeOH with TFA, CHROMOLITH® SpeedROD column 4.6×50 mm, gradient=15 min, wavelength=220 nm); MS(ES):m/z=468 [M+H$^+$].

Intermediate S-2K: (R)-tert-Butyl 2-((S)-1-amino-3-(1-fluorocyclobutyl)-1-oxopropan-2-yl)-5,5,5-trifluoropentanoate

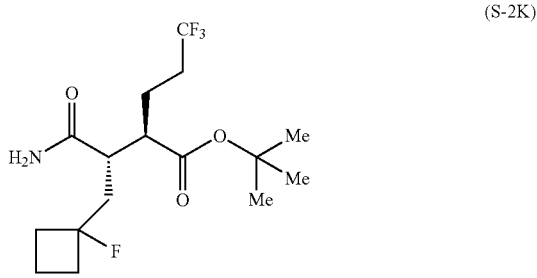 [SMILES: CC(C)(C)OC(=O)[C@H](CCC(F)(F)F)[C@H](CC1(F)CCC1)C(N)=O]

(S-2K)

To a solution of a 1.2:1 mixture of Intermediate S-2I and Intermediate S-2J (1.03 g, 2.203 mmol) in THF (20 mL) at 0° C. was added a cold solution of LiOH (0.158 g, 6.61 mmol) and 50% $H_2O_2$ (1.215 mL, 19.83 mmol) in water (5 mL). After the addition, the mixture was stirred at room temperature overnight. A saturated aqueous solution of $NaHCO_3$ (10 mL) was added, followed by the slow addition of aqueous $Na_2S_2O_3$ (20 mL). The mixture was stirred for 1 h and then concentrated to remove the THF. To the aqueous layer was added 1N NaOH (4 mL), and the mixture was extracted with DCM. The aqueous layer was cooled in an ice-water bath and slowly acidified with conc. HCl to pH 3. The resulting mixture was saturated with solid NaCl and extracted with EtOAc. The combine extracts were washed with sat NaCl, dried with $MgSO_4$, filtered and concentrated to give the crude acid (0.560 g) as a colorless oil. To a solution of the crude mixture of acids (390 mg, 1.094 mmol) in THF (12 mL) at 10° C. was added HOBT (503 mg, 3.28 mmol), followed by EDC (629 mg, 3.28 mmol). The mixture was stirred for 5 min, and then 2N ammonia in MeOH (3.28 mL, 6.57 mmol) was added. The mixture was then stirred at room temperature overnight. The reaction mixture was diluted with EtOAc and was washed with water, saturated aqueous $NaHCO_3$ and brine. The organics were dried $MgSO_4$, filtered and concentrated to dryness. The residue was purified by silica gel column chromatography (24 g column, EtOAc/hexane=0-50%) to give Intermediate S-2K (183 mg, 47%). MS(ES):m/z=356 [M+H$^+$]; $^1$H NMR (400 MHz, chloroform-d) δ 5.71 (br. s., 1H), 5.37 (br. s., 1H), 2.74-2.49 (m, 2H), 2.44-2.24 (m, 3H), 2.23-2.08 (m, 4H), 1.93-1.74 (m, 4H), 1.51 (s, 9H).

Intermediate S-2: (R)-2-((S)-1-Amino-3-(1-fluorocyclobutyl)-1-oxopropan-2-yl)-5,5,5-trifluoropentanoic acid

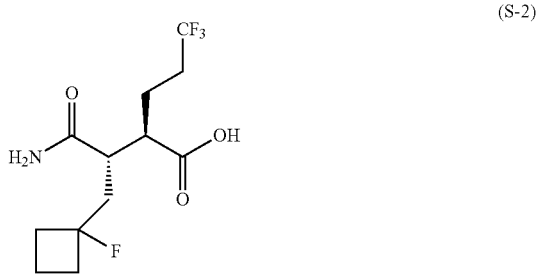 [SMILES: NC(=O)[C@@H](CC1(F)CCC1)[C@@H](CCC(F)(F)F)C(=O)O]

(S-2)

To a solution of Intermediate S-2K (182 mg, 0.512 mmol) in DCM (4 mL) was added TFA (4 mL). The mixture was stirred at room temperature for 3 h. The reaction mixture was then diluted with toluene and concentrate to give the desired product as a white solid (152 mg, 99%). $^1$H NMR (400 MHz, DMSO-d$_6$) δ 12.73 (br. s., 1H), 7.59 (br. s., 1H), 7.01 (br. s., 1H), 2.62-2.53 (m, 1H), 2.39 (td, J=9.6, 4.5 Hz, 1H), 2.31-1.95 (m, 7H), 1.83-1.52 (m, 4H), 1.49-1.30 (m, 1H).

Intermediate S-3: (2R)-2-(2-(tert-Butoxy)-1-(4,4-difluorocyclohexyl)-2-oxoethyl)-5,5,5-trifluoropentanoic acid

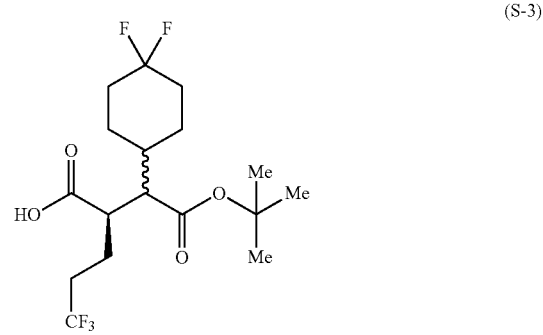 [SMILES: CC(C)(C)OC(=O)C(C1CCC(F)(F)CC1)[C@@H](CCC(F)(F)F)C(=O)O]

(S-3)

Intermediate S-3A: tert-Butyl 2-(4,4-difluorocyclohexylidene)acetate

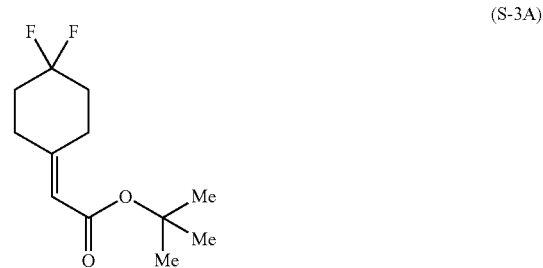 [SMILES: CC(C)(C)OC(=O)C=C1CCC(F)(F)CC1]

(S-3A)

A suspension of sodium hydride (0.298 g, 7.46 mmol) in THF (10 mL) was cooled to 0° C. tert-Butyl diethylphosphonoacetate (1.751 mL, 7.46 mmol) diluted with THF (10 mL) was added dropwise. The reaction mixture was removed from the cooling bath and stirred at room temperature for 30 min. The reaction mixture was then cooled to 0° C. and 4,4-difluorocyclohexanone (1 g, 7.46 mmol) diluted with THF (2 mL) was added. The reaction mixture was stirred at room temperature under nitrogen over night. The reaction was quenched with sat $NH_4Cl$ (50 mL). The aqueous phase was extracted with diethyl ether (3×25 mL). The combined organic layers were dried with $Na_2SO_4$, filtered and concentrated. The crude material was purified by flash chromatography (Teledyne ISCO CombiFlash Rf, 0% to 50% solvent A/B=hexanes/EtOAc, REDISEP® SiO$_2$ 40 g). Concentration of the appropriate fractions provided Intermediate S-3A (1.43 g, 83%). $^1$H NMR (400 MHz, chloroform-d) δ

5.68 (s, 1H), 3.02 (td, J=6.7, 0.9 Hz, 2H), 2.43-2.36 (m, 2H), 2.12-1.97 (m, 4H), 1.51 (s, 9H).

Intermediate S-3B: tert-Butyl 2-(4,4-difluorocyclohexyl)acetate

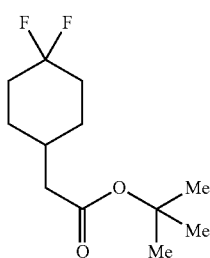

A solution of Intermediate S-3A (1.4 g, 6.03 mmol) in MeOH (20 mL) was treated with 10% palladium on carbon (1 g, 0.940 mmol) to give a suspension. The mixture was then purge three times with nitrogen and then purged three times with hydrogen. After stirring under hydrogen for 2 h, the reaction mixture was filtered through CELITE® and evaporated under reduced pressure to provide Intermediate S-3B (1.4 g, 100%). $^1$H NMR (400 MHz, chloroform-d) δ 2.19 (d, J=6.8 Hz, 2H), 2.15-2.03 (m, 2H), 1.91-1.74 (m, 4H), 1.77-1.65 (m, 1H), 1.47 (s, 9H), 1.42-1.27 (m, 2H).

Intermediate S-3C: (3R)-tert-Butyl 2-(4,4-difluorocyclohexyl)-6,6,6-trifluoro-3-(((S)-4-isopropyl-2-oxooxazolidine-3-carbonyl)hexanoate

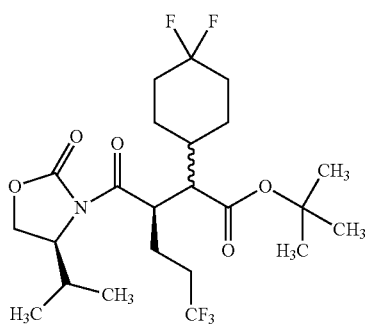

Intermediate S-3C (0.473 g, 56%) was prepared from Intermediate S-3B (0.456 g, 1.71 mmol) and Intermediate S-1G (0.7 g, 2.99 mmol), in a similar way as Intermediate S-1H. $^1$H NMR showed the product was a 1:1 mixture of diastereomers as determined by the integration of the singlet at 1.45 and 1.47 ppm: $^1$H NMR (400 MHz, chloroform-d) δ 4.57-4.17 (m, 4H), 2.80-2.56 (m, 1H), 2.49-2.27 (m, 1H), 2.28-1.57 (m, 9H), 1.49-1.43 (m, 9H), 1.36-1.23 (m, 4H), 1.01-0.86 (m, 6H).

Intermediate S-3: (2R)-2-(2-(tert-Butoxy)-1-(4,4-difluorocyclohexyl)-2-oxoethyl)-5,5,5-trifluoropentanoic acid

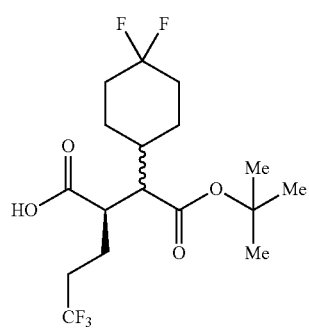

To a cool (0° C.), stirred solution of Intermediate S-3C (0.473 g, 0.947 mmol) in THF (11.6 mL) and water (3.9 mL) was sequentially added hydrogen peroxide (30% in water) (1.07 g, 9.47 mmol) and LiOH (68 mg, 2.84 mmol) and the mixture was stirred for 1 hr. At this time the reaction vessel was removed from the cooling bath and then stirred for 6 hr. To the reaction mixture was added saturated NaHCO$_3$ (10 mL) and saturated Na$_2$SO$_3$ (15 mL), and then the mixture was partially concentrated under reduced pressure. The resulting crude solution was extracted with DCM (2×). The aqueous phase was acidified to pH~1-2 with 1N HCl, extracted with DCM (3×) and EtOAc (1×). The combined organics were washed with brine, dried (Na$_2$SO$_4$), filtered and concentrated under reduced pressure to provide Intermediate S-3 (0.3 g, 82%) as a colorless oil: $^1$H NMR (400 MHz, chloroform-d) δ 2.32-2.05 (m, 4H), 1.99-1.55 (m, 12H), 1.55-1.45 (m, 9H). $^1$H NMR showed a 1:1.

Intermediate S-4: (2R)-3-(tert-Butoxycarbonyl)-5,5-difluoro-2-(3,3,3-trifluoropropyl)hexanoic acid

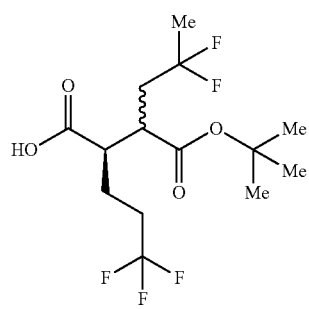

Intermediate S-4A: Benzyl 4,4-difluoropentanoate

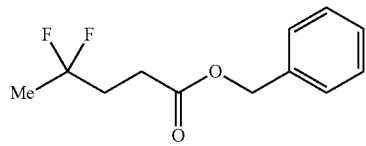

(S-4A)

DAST (19.22 mL, 145 mmol) was added dropwise to a cold (0° C.) solution of benzyl 4-oxopentanoate (20 g, 97 mmol) in DCM (120 mL). The mixture was allowed to warm to room temperature and then heated at 40° C. for 72 hours. The mixture was poured slowly into ice and saturated aqueous sodium bicarbonate mixture. The mixture was stirred 30 minutes until no additional bubbling was observed. The organic layer was separated and the aqueous solution was extracted with DCM (2×240 mL). The combined organic extracts were dried (MgSO$_4$), and the solvent was carefully removed under reduced pressure. The crude material was purified by silica gel chromatography (120 g column) eluting with 100% hexane to 40% EtOAc in hexane to afford the product Intermediate S-4A (7.87 g, 34.5 mmol, 35.6% yield) as a yellow oil $^1$H NMR (400 MHz, chloroform-d) δ ppm 7.29-7.51 (5H, m), 5.17 (2H, s), 2.53-2.67 (2H, m), 2.14-2.36 (2H, m), 1.63 (3H, t, J=18.38 Hz).

Intermediate S-4B: 4-Difluoropentanoic acid

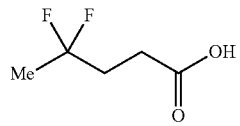

(S-4B)

To a solution of Intermediate S-4A (5000 mg, 21.91 mmol) in THF (45 mL) and MeOH (15 mL) was added a solution of LiOH (32.9 mL, 32.9 mmol) and then the mixture was stirred at room temperature for 1 hour. The reaction mixture was concentrated to remove the organics, diluted with water (10 mL), and extracted with DCM (20 mL). The aqueous layer was acidified to pH 2 with 1N HCl, and then extracted 3×20 mL with DCM. The combined organic phases were dried over Na$_2$SO$_4$ and then concentrated under reduced pressure to obtain Intermediate S-4B (2062 mg, 14.93 mmol, 68.2% yield) as a yellow oil. $^1$H NMR (400 MHz, chloroform-d) δ ppm 11.20-11.61 (1H, m), 2.58 (2H, t, J=7.81 Hz), 2.10-2.32 (2H, m, J=16.18, 16.18, 8.03, 7.81 Hz), 1.63 (3H, t, J=18.38 Hz).

Intermediate S-4C: 4-Difluoropentanoic acid

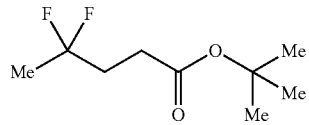

(S-4C)

To a cool (0° C.) (pre-cooled for at least 15 min), stirred solution of Intermediate S-4B (700 mg, 5.07 mmol) in n-hexane (6 mL) and THF (6 mL) under N$_2$ was added tert-butyl 2,2,2-trichloroacetimidate (1.814 mL, 10.14 mmol) portionwise over 5 min and the mixture was stirred for 15 min. Boron trifluoride diethyl etherate (0.065 mL, 0.512 mmol) was added and the reaction mixture was allowed to warm to room temperature as the bath warmed overnight. To the clear reaction mixture was added NaHCO$_3$ (3 g) and the suspension was stirred for 60 min. The suspension was filtered through MgSO$_4$, and washed with 300 mL hexane. The filtrate was allowed to sit for 30 min, and the resulting solid was filtered through the same MgSO$_4$ filter, and washed with hexane (100 mL). The filtrate was concentrated and the crude material was purified by silica gel chromatography (40 g column) eluting with 100% hexane to 50% EtOAc in hexane to afford the product Intermediate S-4C (519 mg, 2.67 mmol, 52.7% yield) as a light yellow oil. 1H NMR (400 MHz, chloroform-d) δ ppm 2.34 (2H, d, J=8.14 Hz), 2.01-2.16 (2H, m), 1.53 (3H, t, J=18.38 Hz), 1.38 (9H, s).

Intermediate S-4D: (3R)-tert-Butyl 2-(2,2-difluoropropyl)-6,6,6-trifluoro-3-((S)-4-isopropyl-2-oxooxazolidine-3-carbonyl)hexanoate

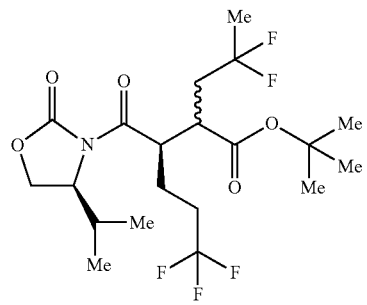

(S-4D)

Intermediate S-4D, as a 1.2:1 mixture of diastereomers (279 mg, 0.607 mmol, 45.3% yield), was prepared from Intermediate S-4C (455 mg, 2.343 mmol) and Intermediate S-1G (358 mg, 1.339 mmol), by the methods described for Intermediate S-1H. $^1$H NMR (400 MHz, chloroform-d) δ ppm 4.43-4.53 (2H, m), 4.22-4.36 (4H, m), 4.03-4.11 (1H, m), 3.02-3.10 (1H, m), 2.93-3.02 (1H, m), 2.48-2.65 (1H, m), 2.35-2.49 (2H, m), 2.23-2.35 (1H, m), 1.91-2.23 (3H, m), 1.74-1.89 (2H, m), 1.53-1.70 (3H, m), 1.42-1.51 (9H, m).

Intermediate S-4: (3R)-tert-Butyl 2-(2,2-difluoropropyl)-6,6,6-trifluoro-3-((S)-4-isopropyl-2-oxooxazolidine-3-carbonyl)hexanoate

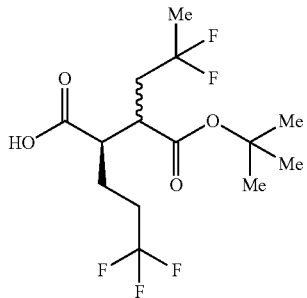

(S-4)

To a cool (0° C.), stirred solution of Intermediate S-4D (279 mg, 0.607 mmol) in THF (9 mL) and water (3 mL) was added H$_2$O$_2$ (0.375 mL, 6.12 mmol) followed by LiOH (44.1 mg, 1.840 mmol). The reaction mixture was gradually warmed to room temperature and stirred for 3 h. A solution of saturated aqueous Na$_2$SO$_3$ (5 mL) and 10 mL sat NaHCO$_3$ was added. The mixture was stirred for 5 min, and then the reaction mixture was partially concentrated. The mixture was extracted with DCM (15 mL) and the aqueous phase was acidified to pH ~2 with 1N HCl, saturated with NaCl, and extracted with DCM (2×30 mL). The combined extracts were dried over MgSO$_4$, filtered and concentrated to give the product as a 1.2:1 mixture of diastereomers Intermediates S-4 (169 mg, 0.485 mmol, 80% yield). $^1$H NMR (400 MHz, chloroform-d) δ ppm 2.89-3.04 (1H, m), 2.68-2.86 (1H, m), 2.38-2.60 (2H, m), 2.19-2.38 (1H, m), 2.07-2.20 (1H, m), 1.87-2.03 (2H, m), 1.73-1.88 (1H, m), 1.63 (3H, t, J=18.49 Hz), 1.37-1.53 (9H, m).

Intermediate S-5: (2R)-3-(tert-Butoxycarbonyl)-6,6,6-trifluoro-5-methyl-2-(3,3,3-trifluoropropyl)hexanoic acid

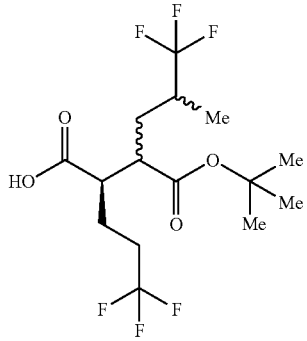

(S-5)

Intermediate S-5A: (E)-tert-Butyl 5,5,5-trifluoro-4-methylpent-2-enoate

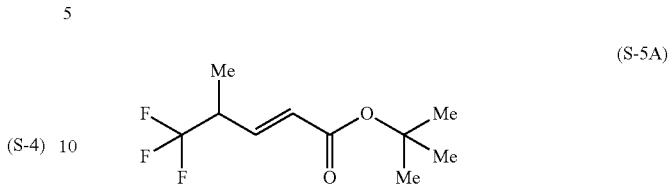

(S-5A)

A solution of tert-butyl 2-(dimethoxyphosphoryl)acetate (9.78 g, 43.6 mmol) in THF (10 mL) was slowly transferred to a suspension of NaH (60% dispersion in mineral oil) (1.903 g, 47.6 mmol) in THF (30 mL) at 0° C. under a nitrogen atmosphere. After the addition was complete, the reaction mixture was stirred at 0° C. for 10 min, and then warmed to room temperature. After being stirred for 30 min, the reaction mixture was cooled to 0° C. again, and a solution of 3,3,3-trifluoro-2-methylpropanal (5 g, 39.7 mmol) in THF (10 mL) was added, and the ice bath was removed. After 12 h at 25° C., the mixture was partitioned between water (60 mL) and EtOAc (60 mL). The aqueous layer was extracted with EtOAc (60 mL), and the combined organic layers were successively washed with water (60 mL) and brine. The resulting solution was dried over MgSO$_4$, concentration under reduced pressure, and purified by silica gel flash chromatography (330 g column, 0% to 15% EtOAc in hexane over 20 min) to obtain Intermediate S-5A (3.61 g, 16.10 mmol, 40.6% yield). $^1$H NMR (400 MHz, chloroform-d) δ 6.77 (dd, J=15.8, 7.7 Hz, 1H), 5.95 (dd, J=15.7, 0.6 Hz, 1H), 3.12-2.93 (m, 1H), 1.56-1.47 (m, 9H), 1.37-1.27 (m, 3H).

Intermediate S-5B: tert-Butyl 5,5,5-trifluoro-4-methylpentanoate

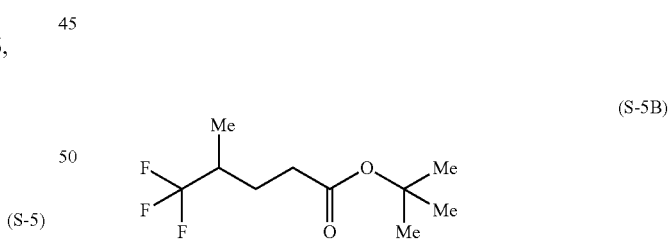

(S-5B)

To a stirred solution of Intermediate S-5A (2 g, 8.92 mmol) in MeOH (30 mL) under a nitrogen atmosphere was added 10% Pd/C (0.949 g, 0.892 mmol) and the suspension was hydrogenated (1 atm, balloon) for 4 h. The suspension was filtered through a pad of CELITE® and the filter cake was rinsed with MeOH (3×10 mL). The combined filtrate and rinses were concentrated in vacuo to give Intermediate S-5B (1.55 g, 6.85 mmol, 77% yield) as a clear oil. $^1$H NMR (400 MHz, methanol-d$_4$) δ 2.46-2.23 (m, 3H), 2.04-1.90 (m, 1H), 1.65-1.53 (m, 1H), 1.51-1.43 (m, 9H), 1.13 (d, J=7.0 Hz, 3H).

Intermediate S-5C: (3R)-tert-Butyl 6,6,6-trifluoro-3-(((S)-4-isopropyl-2-oxooxazolidine-3-carbonyl)-2-(3,3,3-trifluoro-2-methylpropyl)hexanoate

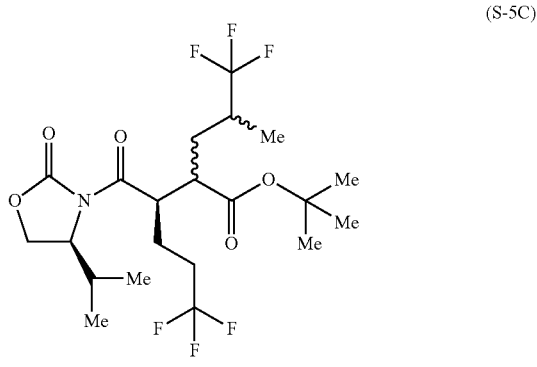 [SMILES: CC(C)[C@H]1COC(=O)N1C(=O)[C@H](CCC(F)(F)F)C(CC(C)C(F)(F)F)C(=O)OC(C)(C)C]

(S-5C)

Intermediate S-5C (1.79 g, 3.64 mmol, 36.1% yield) was prepared from Intermediate S-5B (4.11 g, 18.19 mmol) and Intermediate S-1G (2.7 g, 10.10 mmol), in a similar way as Intermediate S-1H. LC/MS, m/z 490.5 (M−1). HPLC RT=1.86 min. LC/MS (Luna C18 4.6×30 mm, 3µ, 0% to 95% B in 2 min, Flow rate=4 ml/min, detection at 220 nm, A:10:90 H₂O:ACN NH₄OAc/B:10:90 H₂O:ACN NH₄OAc). The diastereomeric ratios were determined to be 2.8:2.2:1.3:1 by integration of the t-butyl signals in the ¹H NMR.

Intermediate S-5: (2R)-3-(tert-Butoxycarbonyl)-6,6,6-trifluoro-5-methyl-2-(3,3,3-trifluoropropyl)hexanoic acid

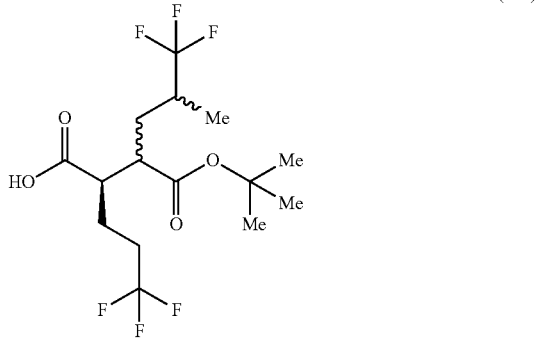

(S-5)

To a cool (0° C.), stirred solution of Intermediate S-5C (2.5 g, 5.09 mmol) in THF (21 mL) and water (7 mL) was added H₂O₂ (50% in water) (3.12 mL, 50.9 mmol) followed by lithium hydroxide monohydrate (0.640 g, 15.26 mmol). The reaction mixture was warmed to room temperature over 1.5 h. After 3.5 h, stirred ice was added (to control exotherm), and the reaction mixture was treated with sat NaHCO₃ (25 mL) and 10% Na₂SO₃ (50 mL), and then stirred at room temperature for 30 min. The aqueous phase was acidified (to pH∼1-2) with 1N HCl, saturated with NaCl, and extracted with DCM (2×125 mL). The extracts were combined, dried (Na₂SO₄), filtered and concentrated to give a mixture of four diastereomers (1.97 g, 5.18 mmol, 102% yield) as a clear oil which was used in the next step without further purification. LC/MS, m/z 379.4 (M−1). HPLC RT=1.27 min. LC/MS (Luna C18 4.6×30 mm, 3 g, 0% to 95% B in 2 min, Flow rate=4 ml/min, detection at 220 nm, A:10:90 H₂O:ACN NH₄OAc/B:10:90 H₂O:ACN NH₄OAc). The diastereomeric ratios were determined to be 2.8:2.2:1.3:1.

Intermediate S-6: (2R,3S)-3-(tert-Butoxycarbonyl)-6,6,6-trifluoro-2-(3-fluoropropyl)hexanoic acid

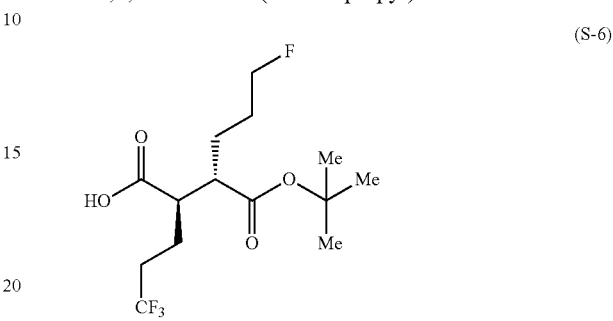

(S-6)

Intermediate S-6A: 3-Fluoropropyltrifluoromethanesulfonate

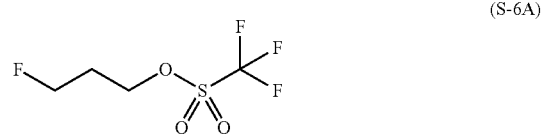 [SMILES: O=S(=O)(OCCCF)C(F)(F)F]

(S-6A)

To a cold (−25° C.), stirred solution of 2,6-lutidine (4.60 mL, 39.5 mmol) in DCM (30 mL) was added triflic anhydride (6.00 mL, 35.5 mmol) over 3 min. Then 3-fluorpropane-1-ol (Oakwood, cat. 010306-25G, 1.61 g, 20.6 mmol) was added. The reaction mixture was warmed to room temperature for 2.5 h. The reaction mixture was concentrated to half its volume and purified by flash chromatography (Teledyne ISCO CombiFlash, isocratic DCM, REDISEP® SiO₂ 120 g, detecting at 254 nM, and monitoring at 220 nM). Concentration of the appropriate fractions provided Intermediate S-6A (2.92 g, 67.4%). ¹H NMR (400 MHz, chloroform-d) δ ppm 4.69 (2H, t, J=6.16 Hz), 4.65 (1H, t, J=5.50 Hz), 4.54 (1H, t, J=5.61 Hz), 2.25 (1H, dt, J=11.39, 5.86 Hz), 2.19 (1H, dt, J=11.44, 5.94 Hz).

Intermediate S-6B: (4S)-4-Benzyl-3-(5,5,5-trifluoropentanoyl)-1,3-oxazolidin-2-one

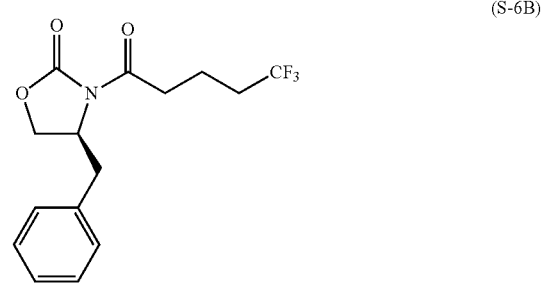 [SMILES: O=C(CCCC(F)(F)F)N1C(=O)OC[C@@H]1Cc1ccccc1]

(S-6B)

To a stirring solution of 5,5,5-trifluoropentanoic acid (14.76 g, 95 mmol) and DMF (0.146 mL) in DCM (50 mL)

was slowly added oxalyl chloride (8.27 mL, 95 mmol). After 2 h, the mixture was concentrated to dryness. A separate flask was changed with (S)-4-benzyloxazolidin-2-one (16.75 g, 95 mmol) in THF (100 mL) and then cooled to −78° C. To the solution was slowly added n-BuLi (2.5M, 37.8 mL, 95 mmol) over 10 min, stirred for 10 min, and then a solution of the above acid chloride in THF (50 mL) was slowly added over 5 min. The mixture was stirred for 30 min, and then warmed to room temperature. The mixture was quenched with saturated aqueous $NH_4Cl$, 10% aq LiCl was then added, and the mixture was extracted with $Et_2O$. The organic layer was washed with saturated aqueous $NaHCO_3$ then with brine, dried ($MgSO_4$), filtered and concentrated to dryness. The residue was purified by $SiO_2$ chromatography (ISCO, 330 g column, eluting with a gradient from 100% hexane to 100% EtOAc) to afford the product Intermediate S-6B; (25.25 g, 85%): $^1$H NMR (400 MHz, $CDCl_3$) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Intermediate S-6C: tert-Butyl (3R)-3-(((4S)-4-benzyl-2-oxo-1,3-oxazolidin-3-yl)carbonyl)-6,6,6-trifluorohexanoate

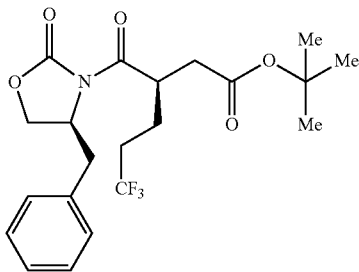

(S-6C)

To a cold (−78° C.), stirred solution of Intermediate S-6B (3.03 g, 9.61 mmol) in THF (20 mL) was added NaHMDS (1.0M in THF) (10.6 mL, 10.60 mmol) under a nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated $NH_4Cl$ and EtOAc. The organic phase was separated, and the aqueous phase was extracted with EtOAc (3×). The combined organics were washed with brine, dried ($Na_2SO_4$), filtered and concentrated under reduced pressure. The residue was purified by flash chromatography (Teledyne ISCO CombiFlash Rf, 5% to 100% solvent A/B=hexanes/EtOAc, REDISEP® $SiO_2$ 120 g). Concentration of the appropriate fractions provided Intermediate S-6C (2.79 g, 67.6%) as a colorless viscous oil: $^1$H NMR (400 MHz, $CDCl_3$) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Intermediate S-6D: (2R)-2-(2-tert-Butoxy-2-oxo-ethyl)-5,5,5-trifluoropentanoic acid

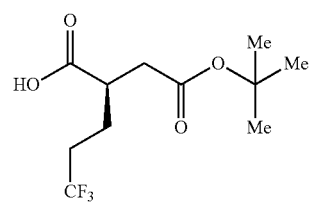

(S-6D)

To a cool (0° C.), stirred solution of Intermediate S-6C (2.17 g, 5.05 mmol) in THF (50 mL) and water (15 mL) was added a solution of LiOH (0.242 g, 10.11 mmol) and $H_2O_2$ (2.065 mL, 20.21 mmol) in $H_2O$ (2 mL). After 10 min, the reaction mixture was removed from the ice bath, stirred for 1 h, and then recooled to 0° C. Saturated aqueous $NaHCO_3$ (25 mL) and saturated aqueous $Na_2SO_3$ (25 mL) were added to the reaction, stirred for 10 min, and then partially concentrated. The resulting mixture was extracted with DCM (2×), cooled with ice and made acidic with conc. HCl to pH 3. The mixture was saturated with solid NaCl, extracted with EtOAc (3×), and then dried over $MgSO_4$, filtered and concentrated to a colorless oil to afford Intermediate S-6D (1.25 g, 92%): $^1$H NMR (400 MHz, $CDCl_3$) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Intermediate S-6: (2R,3S)-3-(tert-Butoxycarbonyl)-6-fluoro-2-(3,3,3-trifluoropropyl)hexanoic acid, and Intermediate S-6E: (2R,3R)-3-(tert-Butoxycarbonyl)-6,6,6-trifluoro-2-(3-fluoropropyl)hexanoic acid

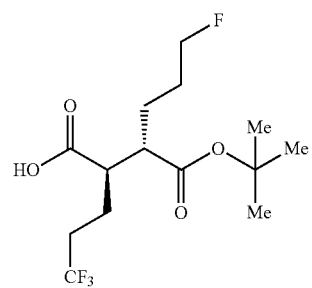

(S-6)

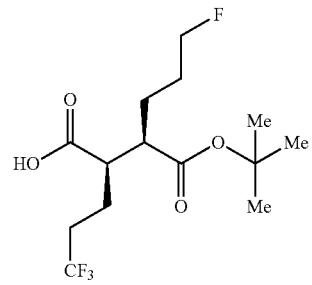

(S-6E)

To a cold (−78° C.), stirred solution of S-6D (1.01 g, 3.73 mmol) in THF (15 mL) was slowly added LDA (4.56 mL, 8.21 mmol) over 5 min. After stirring for 1.5 h, Intermediate S-6A (1.02 g, 4.85 mmol) was added to the reaction mixture over 3 min. After 17 min, the reaction mixture was warmed to −25° C. (ice/MeOH/dry ice) for 1.5 h. The reaction was quenched with water (15 mL) and was extracted with CH$_2$Cl$_2$ (3×20 mL). The organic layer was again extracted with 1N NaOH (3×20 mL) and the aqueous layers were combined. The aqueous layer was cooled in an ice/water bath and then acidified with 6N HCl to pH 1. Next, the aqueous layer was saturated with solid NaCl and extracted with EtOAc (2×85 mL). The combined organics were washed with brine, dried over anhydrous magnesium sulfate, and concentrated under reduced pressure to provide a 1:6.4 mixture of Intermediate S-6 and Intermediate S-6E (0.96 g, 78%) as an oil. $^1$H NMR (400 MHz, chloroform-d) δ ppm 4.48-4.56 (1H, m), 4.36-4.44 (1H, m), 2.75-2.83 (1H, m), 2.61-2.72 (1H, m), 2.08-2.34 (2H, m), 1.83-1.98 (3H, m), 1.66-1.82 (4H, m), 1.44-1.51 (9H, m).

Intermediate S-6: (2R,3S)-3-(tert-Butoxycarbonyl)-6-fluoro-2-(3,3,3-trifluoropropyl)hexanoic acid, and Intermediate S-6E: (2R,3R)-3-(tert-Butoxycarbonyl)-6,6,6-trifluoro-2-(3-fluoropropyl) hexanoic acid

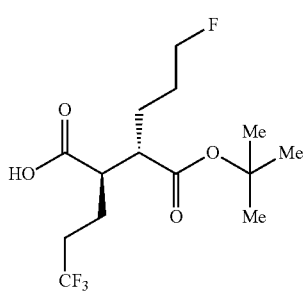

(S-6)

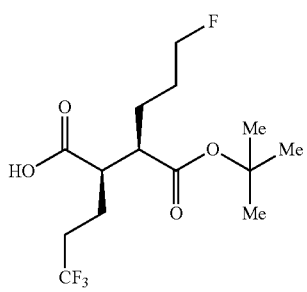

(S-6E)

A 1:6.4 mixture of Intermediate S-6 and Intermediate S-6E (0.30 g, 0.91 mmol) was dissolved in THF (5 mL) to give a colorless solution which was cooled to −78° C. Then, LDA (1.11 mL, 2.00 mmol) (1.8M in heptane/THF/ethylbenzene) was slowly added to the reaction mixture over 3 min. After stirring for 15 min the reaction mixture was placed in a room temperature water bath. After 15 min the reaction mixture was placed back in −78° C. bath and then diethylaluminum chloride (1.91 mL, 1.91 mmol) (1M in hexane) was added slowly over 5 min. The reaction mixture was stirred at −78° C. After 15 min the reaction mixture was placed in a room temperature water bath for 10 min and then cooled back to −78° C. bath. After 15 min the reaction was quenched with MeOH (5.51 mL, 136 mmol), removed from the −78° C. bath and concentrated. To the reaction mixture was added ice and HCl (8.17 mL, 8.17 mmol) and then the mixture was extracted with EtOAc (2×). The combined organic layers were washed with potassium fluoride (0.48 g, 8.26 mmol) in 16 mL of H$_2$O and conc. HCl (10.0 mL, 10.0 mmol). The organics were dried over anhydrous magnesium sulfate and concentrated under reduced pressure to provide a 9:1 mixture of Intermediate S-6 and Intermediate S-6E (0.20 g, 65% yield) as a light yellow oil. $^1$H NMR (400 MHz, chloroform-d) δ ppm 4.47-4.56 (1H, m), 4.33-4.43 (1H, m), 2.59-2.76 (2H, m), 2.21-2.35 (1H, m), 2.06-2.19 (1H, m), 1.88-2.00 (1H, m), 1.59-1.85 (6H, m), 1.47 (9H, s).

Intermediate S-7: (2R,3S)-3-(tert-Butoxycarbonyl)-6,6-difluoro-2-(3,3,3-trifluoropropyl)heptanoic acid

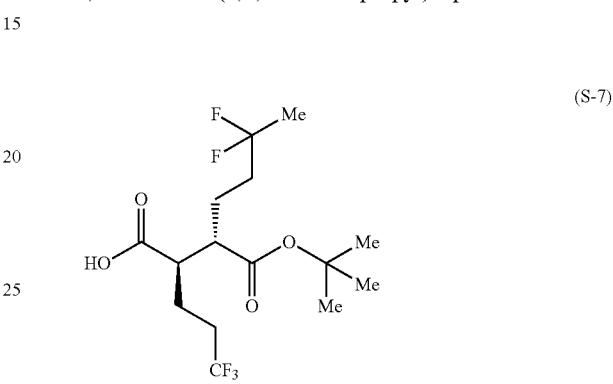

(S-7)

Intermediate S-7A: tert-Butyl 5-oxohexanoate

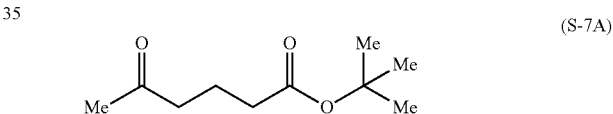

(S-7A)

To a solution of 5-oxohexanoic acid (25 g, 192 mmol) in t-butyl acetate (600 mL) was added perchloric acid (500 μL, 8.31 mmol) and the resulting pale yellow solution was allowed to stir at room temp, with a drying tube in place, for 65 h. The reaction was diluted with ethyl acetate (400 mL) and then quenched with a mixture of sodium bicarbonate (50 g, 595 mmol) and water (100 mL). The organic layer was extracted with saturated aqueous sodium bicarbonate (5×150 mL), water (1×100 mL), brine (1×75 mL), dried over sodium sulfate, and filtered. The solvent was removed in vacuo to give the title compound (30.55 g, 85%) as a light oil. $^1$H NMR (500 MHz, chloroform-d) δ 2.50 (t, J=7.2 Hz, 2H), 2.25 (t, J=7.3 Hz, 2H), 2.16 (s, 3H), 1.89-1.83 (m, 2H), 1.46 (s, 9H).

Intermediate S-7B: tert-Butyl 5,5-difluorohexanoate

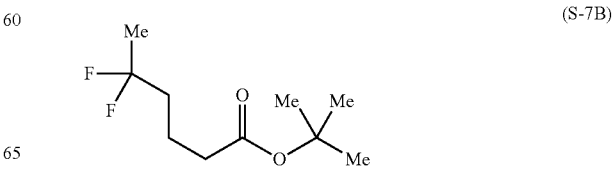

(S-7B)

To a dry 75 mL pressure bottle under nitrogen was added material from Intermediate S-7A (6.0 g, 32.2 mmol) and anhydrous dichloromethane (37.5 mL). The resulting pale yellow solution was cooled slightly under a gentle stream of argon and (diethylamino)sulfur trifluoride (18 ml, 136 mmol) was slowly added. The reaction was securely capped, stirred at room temp for 2 h and then heated to 37° C. for 18 h. The reaction was cooled to −20° C. and slowly (over 30 min) quenched into a beaker containing sodium bicarbonate (110 g, 1.31 mmol), ice water (1600 mL) and dichloromethane (400 mL). The resulting two phase mixture was diluted with dichloromethane (1200 mL), washed with water (1×75 mL), brine (1×75 mL), dried over sodium sulfate, filtered and evaporated to dryness to give 10.3 g of a crude yellow oil. After silica gel purification using a hexane/dichloromethane gradient, the title compound (4.45 g, 66.3%) was isolated as a colorless oil. $^1$H NMR (500 MHz, chloroform-d) δ 2.30 (t, J=7.2 Hz, 2H), 1.95-1.75 (m, 4H), 1.62 (t, J=18.5 Hz, 3H), 1.47 (s, 9H).

Intermediate S-7C: (3R)-tert-Butyl 2-(3,3-difluorobutyl)-6,6,6-trifluoro-3-((S)-4-isopropyl-2-oxooxazolidine-3-carbonyl)hexanoate

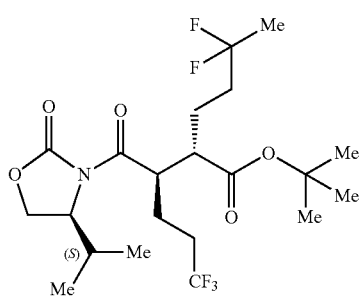

(S-7C)

Intermediate S-7C was prepared from Intermediate S-7B (3.8 g, 18.25 mmol) and Intermediate S-1G (3.21 g, 12.01 mmol) according to the general procedure as described earlier for S-1H. Purification by silica gel chromatography using an ethyl acetate/hexane gradient afforded Intermediate S-7C (390 mg) which was used directly in the subsequent reaction; HPLC: RT=4.23 min (MeOH/H$_2$O/0.1% TFA, Luna C18 2×50 mm×3μ, 4 min gradient, flow rate=0.8 mL/min, wavelength=220 nm); MS(ES) m/z=496 [M+Na]; $^1$H NMR (500 MHz, chloroform-d) δ 4.52 (dt, J=8.4, 3.3 Hz, 1H), 4.38-4.23 (m, 2H), 4.10-4.02 (m, 1H), 2.71 (ddd, J=10.4, 6.6, 3.9 Hz, 1H), 2.51-2.36 (m, 1H), 2.19-1.77 (m, 8H), 1.58 (t, J=18.3 Hz, 3H), 1.50-1.45 (m, 9H), 0.94 (dd, J=15.9, 7.1 Hz, 6H).

Intermediate S-7: (2R,3S)-3-(tert-Butoxycarbonyl)-6,6-difluoro-2-(3,3,3-trifluoropropyl)heptanoic acid

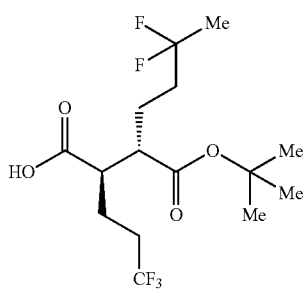

(S-7)

Intermediate S-7 was prepared from Intermediate S-7C (389.5 mg, 0.823 mmol), lithium hydroxide (62 mg, 2.59 mmol) and hydrogen peroxide, 30% in water (810 mL, 7.93 mmol) according to the general procedure as described earlier for Intermediate S-1I to give the title compound (340 mg, 100%). $^1$H NMR (500 MHz, chloroform-d) δ 2.76-2.70 (m, 1H), 2.65 (td, J=8.9, 4.0 Hz, 1H), 2.35-2.22 (m, 1H), 2.19-2.08 (m, 1H), 2.03-1.72 (m, 6H), 1.61 (t, J=18.4 Hz, 3H), 1.49 (s, 9H).

Intermediate S-8: (2R)-2-(2-(tert-Butoxy)-2-oxo-1-(4-(trifluoromethyl)cyclohexyl)ethyl)-5,5,5-trifluoropentanoic acid

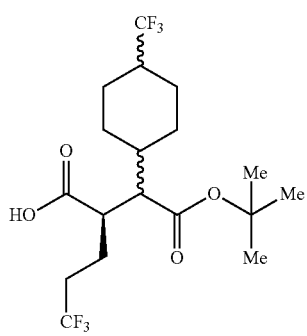

(S-8)

Intermediate S-8A: tert-Butyl 2-(4-(trifluoromethyl)cyclohexylidene)acetate

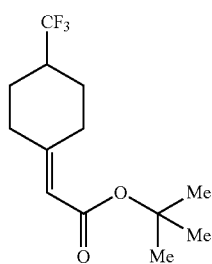

(S-8A)

A suspension of sodium hydride (0.241 g, 6.02 mmol) in hexanes (10 mL) was stirred for 15 minutes and then the hexanes were decanted and THF (10 mL) was added. After cooling to 0° C., tert-butyl diethylphosphonoacetate (1.41 mL, 6.06 mmol), diluted with THF (10 mL) was added dropwise. The reaction mixture was removed from the cooling bath and stirred at room temperature for 30 min. The reaction mixture was then cooled to 0° C. and 4,4-difluorocyclohexanone (1 g, 6.02 mmol), diluted with THF (2 mL) was added. The reaction mixture was stirred at room temperature under nitrogen overnight. The reaction was then quenched with saturated aqueous NH$_4$Cl (50 mL). The aqueous phase was extracted with diethyl ether (3×25 mL). The combined organic layers were dried with Na$_2$SO$_4$, filtered and concentrated. The crude material was purified by flash chromatography (Teledyne ISCO CombiFlash Rf, 0% to 50% solvent A/B=hexanes/EtOAc, REDISEP® SiO$_2$ 40 g). Concentration of the appropriate fractions provided Intermediate S-8A (1.16 g, 73%). $^1$H NMR (400 MHz, chloroform-d) δ 5.63 (s, 1H), 3.93 (d, J=14.3 Hz, 1H), 2.38 (d, J=13.6 Hz, 1H), 2.34-2.14 (m, 2H), 2.14-2.05 (m, 2H), 1.91 (td, J=13.9, 4.4 Hz, 1H), 1.55-1.43 (m, 11H).

Intermediate S-8B: tert-Butyl 2-(4-(trifluoromethyl)cyclohexyl)acetate

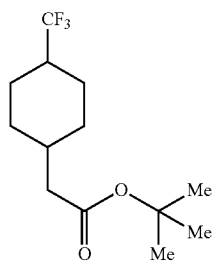

(S-8B)

A solution of Intermediate S-8A (1.15 g, 4.35 mmol) and 10% palladium on carbon (0.463 g, 0.435 mmol) in MeOH (20 mL) were mixed to give a suspension. The mixture was then purge three times with vacuum and nitrogen and then purged three times with vacuum and hydrogen. After stirring under hydrogen for 2 hrs, the reaction mixture was filtered through CELITE® and evaporated under reduced pressure to provide the desired compound (1.16 g, 100%). $^1$H NMR (400 MHz, chloroform-d) δ 2.32-2.23 (m, 1H), 2.22-2.04 (m, 2H), 2.02-1.85 (m, 3H), 1.83-1.68 (m, 1H), 1.67-1.52 (m, 3H), 1.47 (s, 8H), 1.44-1.28 (m, 1H), 1.09-0.95 (m, 1H).

Intermediate S-8C: (3R)-tert-Butyl 6,6,6-trifluoro-3-(((S)-4-isopropyl-2-oxooxazolidine-3-carbonyl)-2-(4-(trifluoromethyl)cyclohexyl)hexanoate

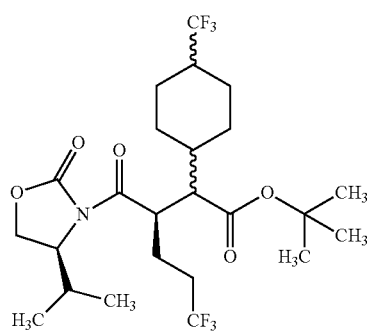

(S-8C)

A mixture of four diastereomers (S-8C) (0.428 g, 33%) was prepared from Intermediate S-8B (0.66 g, 2.47 mmol) and Intermediate S-1G (1.15 g, 4.32 mmol), in a similar way as Intermediate S-1H. $^1$H NMR (400 MHz, chloroform-d) δ 4.55-4.17 (m, 2H), 2.24-1.79 (m, 8H), 1.75-1.50 (m, 6H), 1.50-1.41 (m, 9H), 1.38-1.20 (m, 4H), 1.07-0.79 (m, 6H).

Intermediate S-8: (2R)-2-(2-(tert-Butoxy)-2-oxo-1-(4-(trifluoromethyl)cyclohexyl)ethyl)-5,5,5-trifluoropentanoic acid

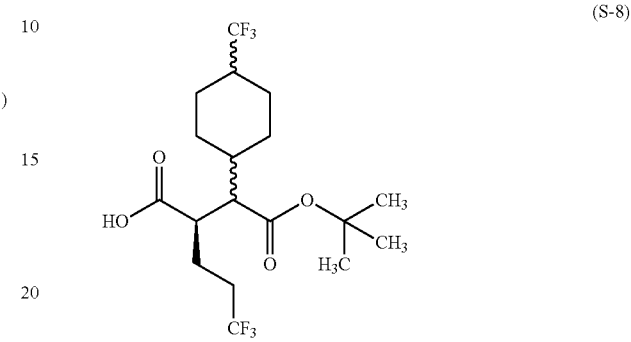

(S-8)

To a cool (0° C.), stirred solution of the mixture of S-8C (0.428 g, 0.805 mmol) described above in THF (10 mL) and water (3 mL) was sequentially added hydrogen peroxide (30% in water) (0.913 g, 8.05 mmol) and LiOH (58 mg, 2.42 mmol) and the mixture was stirred for 1 hr. At this time the reaction vessel was removed from the cold bath and then stirred for 6 hr. To the reaction mixture was added saturated NaHCO$_3$ (10 mL) and saturated Na$_2$SO$_3$ (15 mL), and it was then partially concentrated under reduced pressure. The resulting crude solution was extracted with DCM (2×). The aqueous phase was acidified to pH~1-2 with 1N HCl, extracted with DCM (3×) and EtOAc (1x). The combined organics were washed with brine, dried (Na$_2$SO$_4$), filtered and concentrated under reduced pressure to provide Intermediate S-8 as a mixture of diastereomers (0.3 g, 89%). $^1$H NMR (400 MHz, chloroform-d) δ 2.86-2.47 (m, 3H), 2.30-2.14 (m, 1H), 2.08-1.70 (m, 8H), 1.56-1.41 (m, 9H), 1.39-1.03 (m, 5H).

Intermediate S-9: (2R)-2-(2-(tert-Butoxy)-1-(3,3-difluorocyclobutyl)-2-oxoethyl)-5,5,5-trifluoropentanoic acid

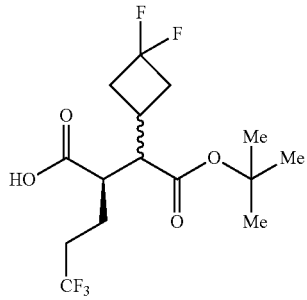

(S-9)

Intermediate S-9A: 2-(3,3-Difluorocyclobutyl)acetic acid

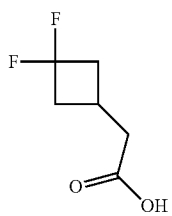
(S-9A)

A solution of 2-(3,3-difluorocyclobutyl)ethanol (270 mg, 2.0 mmol, prepared as described in Bogen, S. et al., *Bioorg. Med. Chem. Lett.*, 18:4219 (2008)) in acetone (5 mL) was treated with Jones reagent (2.7 mmol, 1 mL of 2.7 M solution) over a period of 30 minutes at room temperature. After 2 hours, additional Jones reagent (0.25 mL) was added. After 1 hour, the reaction mixture was filtered through CELITE®, and concentrated under reduced pressure. The reaction mixture was re-dissolved in ethyl acetate (10 mL), washed with water (2×20 mL), brine (20 mL), and then dried over MgSO$_4$, The mixture was then filtered and concentrated to isolate Intermediate S-9A (275 mg, 92% yield) as a tan solid. $^1$H NMR (500 MHz, chloroform-d) δ 2.74-2.87 (2H, m), 2.57-2.62 (2H, m), 2.48-2.56 (1H, m, J=8.60, 4.30, 4.30, 1.94 Hz), 2.23-2.35 (2H, m).

Intermediate S-9B: tert-Butyl 2-(3,3-difluorocyclobutyl)acetate

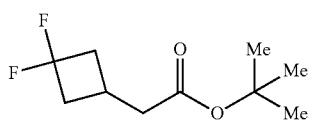
(S-9B)

tert-Butyl 2,2,2-trichloroacetimidate (1.58 mL, 8.3 mmol) was added to Intermediate S-9B (620 mg, 4.1 mmol) in THF (5 mL) and hexanes (5 mL) at 0° C. over a period of 5 minutes. After 30 minutes, BF$_3$-Et$_2$O (0.052 mL, 0.41 mmol) was added. After 1 hour, the reaction mixture was removed from the ice bath and stirred at room temperature. After 16 hours, the reaction mixture was poured over saturated NaHCO$_3$ (50 mL), extracted with hexanes (2×50 mL), dried over Na$_2$SO$_4$, filtered and concentrated under reduced pressure. The reaction mixture was purified by silica gel chromatography (DCM) to isolate Intermediate S-9B (720 mg, 3.5 mmol, 85% yield) as a clear oil. $^1$H NMR (500 MHz, chloroform-d) δ 2.74-2.87 (2H, m), 2.57-2.62 (2H, m), 2.48-2.56 (1H, m, J=8.60, 4.30, 4.30, 1.94 Hz), 2.23-2.35 (2H, m).

Intermediate S-9C: (3R)-tert-Butyl 2-(3,3-difluorocyclobutyl)-6,6,6-trifluoro-3-(((S)-4-isopropyl-2-oxooxazolidine-3-carbonyl)hexanoate

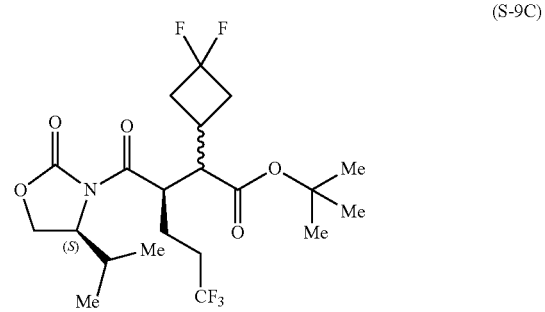
(S-9C)

Intermediate S-9C (500 mg, 44% yield), as a 1.4:1 mixture of diastereomers, was prepared from Intermediate S-9B (900 mg, 1.8 mmol) and S-1G (650 mg, 2.4 mmol) according to the general procedure described for Intermediate S-1H. HPLC: RT=2.25 min (LCMS: PHENOMENEX® Luna 5 micron C18 4.6×30 mm, 0 to 100 B in 2 min with 1 min hold time, Flow rate=5 ml/min, detection at 254 nm, Solvent A: 10% methanol/90% water 0.1% TFA; Solvent B: 10% water 90% methanol 0.1% TFA). MS(ES): m/z=494.24 [M+Na]$^+$.

Intermediate S-9

Intermediate S-9 (80 mg, 48% yield), as a 1.4:1 mixture of diastereomers, was prepared from Intermediate S-9C (220 mg, 0.47 mmol) according to the procedures described for Intermediate S-1I. HPLC: RT=1.57 min (LCMS: Luna C18 4.6×30 mm 3 micron; Solvent A: 10:90 H$_2$O:ACN, 10 mM NH$_4$OAc. Solvent B: 10:90 H$_2$O:ACN, 10 mM NH$_4$OAc; 0%-95% B in 2 min; 4 mL/min flow). MS(ES): m/z=359.4 [M−H]$^+$.

Intermediate A-1: (2-Amino-3-cyclopropoxyphenyl)(3-fluorophenyl)methanone

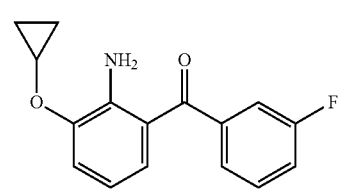
(A-1)

Intermediate A-1A: Methyl 2-nitro-3-(vinyloxy)benzoate

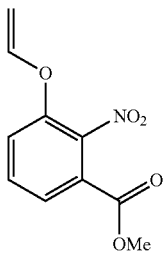

(A-1A)

A mixture of copper (II) acetate (11.98 g, 65.9 mmol) and dichloromethane (80 mL) were stirred at room temperature for 10 minutes, before the addition of 2,4,6-trivinyl-1,3,5, 2,4,6-trioxatriborinane with pyridine (1:1) (10.63 g, 44.2 mmol, 0.67 eq), methyl 3-hydroxy-2-nitrobenzoate (U.S. Publication No. 2012/0035194 A1 [0202]) (13 g, 65.9 mmol), pyridine (26.7 mL, 330 mmol), and molecular sieves (1 g). The resulting deep blue mixture was stirred at room temperature for 5 days, with the reaction opened to the air. The reaction solution was filtered through a pad of CELITE®, washing with some dichloromethane. The filtrate was washed with 3M aqueous ammonium acetate (2×), water, and brine, and then dried and concentrated in vacuo. The crude product mixture was purified via silica gel chromatography (0% to 20% EtOAC in DCM over 15 minutes, 120 g column) to give Intermediate A-1A (7.42 g, 33.2 mmol, 50.4% yield). HPLC: RT=2.487 min (H$_2$O/MeOH with TFA, SunFire C18 3.5 μm, 2.1×30 mm, gradient=4 min, wavelength=220 nm); MS(ES):m/z=246 [M+Na]$^+$; $^1$H NMR (400 MHz, chloroform-d) δ 7.77 (dd, J=7.8, 1.2 Hz, 1H), 7.55 (t, J=8.1 Hz, 1H), 7.38 (dd, J=8.4, 1.3 Hz, 1H), 6.61 (dd, J=13.6, 5.9 Hz, 1H), 4.95 (dd, J=13.6, 2.4 Hz, 1H), 4.69 (dd, J=5.9, 2.4 Hz, 1H), 3.93 (s, 3H), 1.56 (s, 1H), 0.03 (s, 1H).

Intermediate A-1B: Methyl 3-cyclopropoxy-2-nitrobenzoate

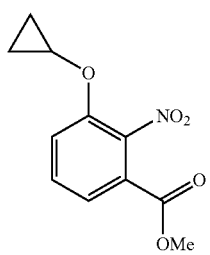

(A-1B)

In a 3 necked, 500 mL flask, a solution of 2,2,2-trichloroacetic acid (16.30 g, 100 mmol) in dichloromethane (100 mL) was slowly added via an addition funnel to a −10° C. solution of diethylzinc (1M hexanes, 100 mL, 100 mmol) under a nitrogen atmosphere. The reaction mixture was stirred for 10 min. Next, diiodomethane (8 mL, 100 mmol) was dropwise added by syringe, and the reaction solution was stirred for 10 min. A solution of Intermediate A-1A (7.42 g, 33.2 mmol) in dichloromethane (20 mL) was added slowly via an addition funnel. The solution was allowed to warm to room temperature overnight. The reaction mixture was cooled to 0° C. and quenched with 1M HCl. The reaction solution was transferred to a reparatory funnel, and the aqueous layer was extracted with dichloromethane (3×). The combined extracts were washed with saturated sodium bicarbonate, water and brine, dried over anhydrous sodium sulfate, filtered and concentrated. The crude product mixture was purified by silica gel chromatography (0%-30% EtOAc/Heptane over 15 minutes, 220 g column) to provide Intermediate A-1B (4.7 g, 19.81 mmol, 60.0% yield). HPLC: RT=2.66 min (H$_2$O/MeOH with TFA, SunFire C18 3.5 μm, 2.1×30 mm, gradient=4 min, wavelength=220 nm); MS(ES):m/z=260 [M+Na]$^+$; $^1$H NMR (400 MHz, chloroform-d) δ 7.68-7.57 (m, 2H), 7.57-7.41 (m, 1H), 4.03-3.82 (m, 4H), 0.94-0.78 (m, 4H).

Intermediate A-1C: 3-Cyclopropoxy-2-nitrobenzoic acid

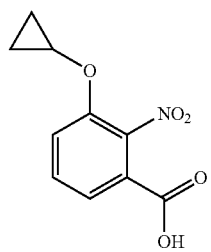

(A-1C)

A solution of Intermediate A-1B (4.7 g, 19.81 mmol) in THF (30 mL) and MeOH (30 mL) was treated with a solution of lithium hydroxide (2.88 g, 120 mmol) in water (15 mL, 833 mmol). The mixture was stirred at room temperature for 2 hours. The organic solvents were removed under reduced pressure. The resulting aqueous slurry was diluted with water, acidified with 1M HCl and extracted with ethyl acetate (3×). The extracts were combined and washed with brine, dried over anhydrous sodium sulfate, filtered and concentrated to provide Intermediate A-1C (4.35 g, 19.8 mmol, 98% yield) as a yellow solid. HPLC: RT=2.186 min (H$_2$O/MeOH with TFA, SunFire C18 3.5 μm, 2.1×30 mm, gradient=4 min, wavelength=220 nm); MS(ES):m/z=246 [M+Na]$^+$; $^1$H NMR (400 MHz, chloroform-d) δ 7.76 (dd, J=7.7, 1.8 Hz, 1H), 7.68-7.46 (m, 2H), 4.02 (tt, J=6.0, 2.9 Hz, 1H), 1.00-0.52 (m, 4H).

Intermediate A-1D: 2-Amino-3-cyclopropoxybenzoic acid

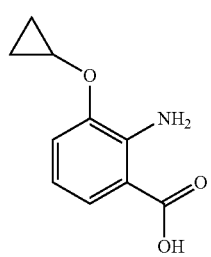

(A-1D)

A 50 mL RB flask was charged with Intermediate A-1C (205 mg, 0.919 mmol), 10% Pd/C (25 mg, 0.919 mmol) and methanol (6 mL). The flask was vacuum flushed with nitrogen (3×) followed by a vacuum flush with a hydrogen balloon (3×). The resulting suspension was stirred under a balloon of hydrogen at room temperature overnight. The solution was filtered through CELITE®, washed with methanol, and the filtrate was concentrated to provide an oil. The crude material was azeotroped with toluene (2×), and dried under vacuum to provide crude Intermediate A-1D (175 mg, 0.906 mmol, 99% yield) as a solid. The product was used without further purification in the next reaction. HPLC: RT=2.31 min (H$_2$O/MeOH with TFA, SunFire C18 3.5 µm, 2.1×30 mm, gradient=4 min, wavelength=220 nm); MS(ES):m/z=194.12 [M+H]$^+$.

Intermediate A-1E:
2-Amino-3-cyclopropoxy-N-methoxy-N-methylbenzamide

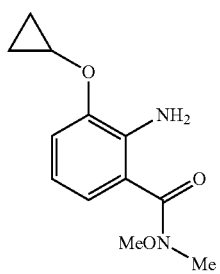

(A-1E)

In a flask, at room temperature, was added Intermediate A-1D (6.61 g, 34.2 mmol), N,O-dimethylhydroxylamine hydrochloride (10.01 g, 103 mmol), N-Ethyl-N'''-(3-Dimethylaminopropyl)carbodiimide hydrochloride (7.87 g, 41.1 mmol) and 1-hydroxybenzotriazole hydrate (6.29 g, 41.1 mmol) in 50 mL of DMF. To the solution was added triethylamine (19.07 mL, 137 mmol). The reaction solution was stirred at 60° C. overnight and then cooled to room temperature. The reaction mixture was partitioned between water and ethyl acetate and transferred to a separatory funnel and the organic layer was washed with 10% LiCl, water, and brine. The organic phase was dried over anhydrous sodium sulfate, filtered and concentrated to provide a dark oil. The crude product mixture was purified via silica gel chromatography (0%-50% of EtOAc/DCM over 15 minutes, 120 g column) to give Intermediate A-1E (5.2 g, 22.01 mmol, 64.3% yield). HPLC: RT=1.975 min (H$_2$O/MeOH with TFA, SunFire C18 3.5 µm, 2.1×30 mm, gradient=4 min, wavelength=220 nm); MS(ES):m/z=237.12 [M+H]$^+$; $^1$H NMR (400 MHz, chloroform-d) δ 7.17 (dd, J=8.0, 1.2 Hz, 1H), 7.02 (dd, J=7.9, 1.3 Hz, 1H), 6.67 (t, J=7.9 Hz, 1H), 4.78 (br. s., 2H), 3.88-3.73 (m, 1H), 3.69-3.56 (m, 3H), 3.36 (s, 3H), 0.92-0.72 (m, 4H).

Intermediate A-1

A solution of 1-fluoro-3-iodobenzene (1.009 mL, 8.59 mmol) in tetrahydrofuran (100 mL) was cooled to −78° C. in a dry ice/acetone bath under nitrogen. Then a solution of n-BuLi (1.8 M in hexanes, 5.37 mL, 8.59 mmol) was added via syringe over 15 minutes and stirred for 60 minutes to give a dark-yellow suspension. Then a solution of Intermediate A-1E (0.58 g, 2.455 mmol) in 10 mL of THF was added via syringe and the reaction mixture was stirred for 40 minutes at −78° C. After 40 minutes, the mixture was poured into a mixture of ice and 1N HCl and extracted into ethyl acetate. The organic layer was washed with water and brine and concentrated. The crude product mixture was purified via silica gel chromatography (0%-100% of EtOAC heptane in 15 minutes, 40 g column) to give Intermediate A-1 (0.46 g, 1.696 mmol, 69.1% yield). HPLC: RT=3.481 min (H$_2$O/MeOH with TFA, SunFire C18 3.5 µm, 2.1×30 mm, gradient=4 min, wavelength=220 nm); MS(ES):m/z=272.16 [M+H]$^+$; $^1$H NMR (400 MHz, chloroform-d) δ 7.48-7.40 (m, 2H), 7.36 (ddd, J=9.3, 1.9, 1.1 Hz, 1H), 7.27-7.18 (m, 2H), 7.08 (dd, J=8.3, 1.2 Hz, 1H), 6.58 (t, J=8.0 Hz, 1H), 6.39 (br. s., 2H), 3.83 (t, J=4.5 Hz, 1H), 0.86 (d, J=4.4 Hz, 4H).

Intermediates A-2 to A-5, listed below in Table 1, were prepared according to the general synthetic procedure described for Intermediate A-1, using the appropriate aniline and organometallic reagent.

TABLE 1

| Int. | Structure | Name | HPLC RT (Min) | LC/MS [M + H]$^+$ |
|---|---|---|---|---|
| A-2 | 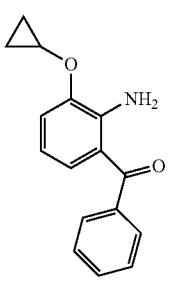 [SMILES: Nc1c(OC2CC2)cccc1C(=O)c1ccccc1] | (2-amino-3-cyclopropoxyphenyl)(phenyl)methanone | 3.32[1] | 254 |
| A-3 | 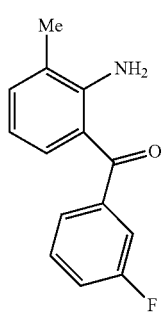 [SMILES: Cc1cccc(C(=O)c2cccc(F)c2)c1N] | (2-amino-3-methylphenyl)(3-fluorophenyl)methanone | 2.84[2] | 230 |
| A-4 | 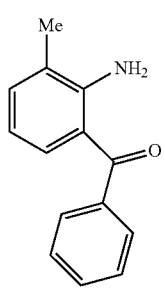 [SMILES: Cc1cccc(C(=O)c2ccccc2)c1N] | (2-amino-3-methylphenyl)(phenyl)methanone | 0.98[3] | 212 |

TABLE 1-continued

| Int. | Structure | Name | HPLC RT (Min) | LC/MS [M + H]+ |
|---|---|---|---|---|
| A-5 | ![structure] | (2-amino-3-bromophenyl)(phenyl)methanone | 1.89[4] | 330 |

Intermediate A-6:
(2-Amino-4-methoxyphenyl)(phenyl)methanone

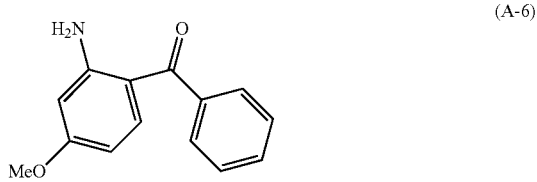 [SMILES: COc1ccc(C(=O)c2ccccc2)c(N)c1]

(A-6)

Trichloroborane (1M in dichloromethane) (180 mL, 180 mmol) was dropwise added to a 0° C. solution of 3-methoxyaniline (20 g, 160 mmol) in tetrachloroethane (50 mL) and the mixture was stirred for 15 min. Benzonitrile (32 g, 310 mmol), followed by aluminum trichloride (24 g, 179 mmol) were added and the mixture was allowed to warm to room temperature over 30 minutes and then refluxed for 5 h. The mixture was cooled to 0° C. and 1.5 N HCl (300 mL) was cautiously added and the mixture was then heated to 80° C. for 30 minutes. The mixture was cooled to room temperature and extracted with DCM. The combined organic layers were dried and then concentrated to afford the crude product. The crude material was purified by silica gel chromatography (pet. ether/ethyl acetate) to provide Intermediate A-6 (7.0 g). HPLC RT=1.783 min (MeOH/H$_2$O/ 0.1% TFA, ZORBAX® SB C18 5 g, 4.6×50 mm, Flow=5 mL/min, 2 min gradient, wavelength=220 nm); MS(ES): m/z=228 [M+H$^+$].

Intermediate A-7:
(2-Amino-3-fluorophenyl)(phenyl)methanone

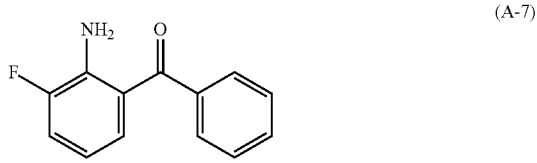 [SMILES: Nc1c(F)cccc1C(=O)c1ccccc1]

(A-7)

Intermediate A-7A:
7-Fluoro-3-hydroxy-3-phenylindolin-2-one

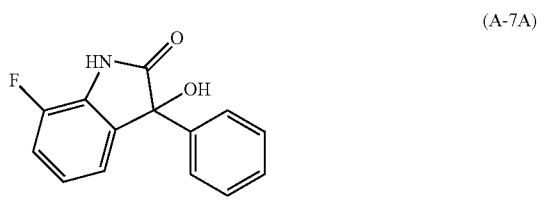 [SMILES: O=C1Nc2c(F)cccc2C1(O)c1ccccc1]

(A-7A)

To a stirring solution of 7-fluoroindoline-2,3-dione (12.22 g, 74 mmol) in THF (40 mL) at 0° C. was added phenylmagnesium bromide (148 mL, 148 mmol) dropwise. The reaction mixture was allowed to stir at room temperature for 15 min after the addition was completed. The reaction mixture was quenched with saturated NH$_4$Cl and extracted with EtOAc. The combined extracts were washed with brine, dried (Na$_2$SO$_4$), filtered and concentrated. The residue was purified by silica gel chromatography (EtOAc/hexane) to afford Intermediate A-7A (18.84 g, 88%) as a yellow solid: $^1$H NMR (400 MHz, DMSO-d$_6$) δ 10.92 (s, 1H), 7.37-7.25 (m, 5H), 7.19 (ddd, J=10.4, 8.1, 1.3 Hz, 1H), 7.04-6.92 (m, 2H); HPLC: RT=1.810 min (CHROMOLITH® SpeedROD column 4.6×50 mm, 10-90% aqueous methanol over 4 minutes containing 0.1% TFA, 4 mL/min, monitoring at 220 nm); MS(ES): m/z=599 [M+H–H$_2$O]$^+$.

Intermediate A-7

To a stirring solution of potassium ferrocyanide (20.87 g, 56.7 mmol), sodium bicarbonate (4.94 g, 58.8 mmol) and NaOH (0.959 g, 23.97 mmol) in water (100 mL) at 110-120° C. was added a solution of Intermediate A-7A (5.3 g, 21.79 mmol) in DMF (12 mL) dropwise over 10 min. After refluxing for 1.5 hr, the reaction mixture was cooled to room temperature. The mixture was extracted twice with DCM. The combined extracts were washed with water and 10% LiCl, dried (MgSO$_4$), filtered and concentrated. The residue was purified by silica gel chromatography (EtOAc/hexane) to give Intermediate A-7 (2.97 g, 63%) as yellow solid: $^1$H NMR (400 MHz, CDCl$_3$) δ 7.63-7.71 (2H, m), 7.54-7.60 (1H, m), 7.45-7.53 (2H, m), 7.25-7.31 (1H, m), 7.17 (1H, ddd, J=11.11, 7.81, 1.32 Hz), 6.56 (1H, td, J=8.03, 5.06 Hz), 6.12 (2H, br. s.); HPLC: RT=2.513 min (CHROMOLITH® SpeedROD column 4.6×50 mm, 10-90% aqueous methanol over 4 minutes containing 0.1% TFA, 4 mL/min, monitoring at 220 nm); MS(ES): m/z=216 [M+H]$^+$.

Intermediate A-8:
(2-Amino-3-fluorophenyl)(phenyl)methanone

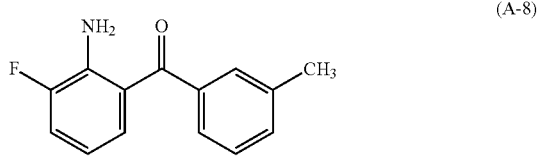 [SMILES: Cc1cccc(C(=O)c2cccc(F)c2N)c1]

(A-8)

Intermediate A-8 was prepared according to the procedures described for Intermediate A-7. HPLC: RT=2.07 min (H₂O/MeOH with TFA, SunFire C18 2.5 μm, 2.1×30 mm, gradient=3 min, wavelength=220 nm); MS(ES): m/z=230 [M+H]⁺.

Intermediate A-9:
(2-Amino-3-methoxyphenyl)(phenyl)methanone

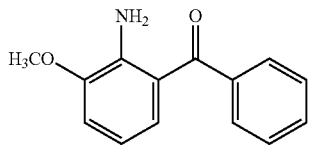

(A-9)

Intermediate A-9A:
8-Methoxy-2-methyl-4H-benzo[d][1,3]oxazin-4-one

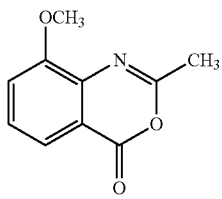

(A-9A)

A solution of 2-amino-3-methoxybenzoic acid (10.1 g, 60.4 mmol) in acetic anhydride (50 ml, 530 mmol) was heated to 140° C. with stirring for 180 min. The reaction mixture was cooled to room temperature and concentrated to provide Intermediate A-9A (11.51 g, 100%): ¹H NMR (400 MHz, DMSO-d₆) δ 7.59 (dd, J=6.9, 2.3 Hz, 1H), 7.52-7.42 (m, 2H), 3.89 (s, 3H), 2.39 (s, 3H); HPLC: RT=0.795 min (H₂O/MeOH with TFA, SunFire C18 2.5 μm, 2.1×30 mm, gradient=2 min, wavelength=220); MS(ES): m/z=292 [M+H]⁺.

Intermediate A-9

A 100 mL round-bottomed flask containing Intermediate A-9A (1.0 g, 5.23 mmol) in diethyl ether (20 mL), toluene (10 mL) and THF (10 mL) was cooled to 0° C. Phenyl magnesium bromide (1.9 mL, 5.75 mmol, 3M in Et₂O) was added in one portion. The reaction mixture was allowed to warm to room temperature and stirred overnight. The reaction mixture was cooled to 0° C. and 30 g crushed ice and 25 mL 6N HCl were added. The reaction mixture was allowed to slowly warm to room temperature. The reaction mixture was partitioned between ethyl acetate (100 mL) and brine (50 mL). The aqueous phase was separated and extracted with ethyl acetate (1×100 mL). The combined organic layers were dried (MgSO₄), filtered and concentrated. The residue was purified by silica gel chromatography to provide 882 mg of a colorless solid. This material was dissolved in AcOH (10 mL) and treated with concentrated HCl (6 mL, 72.0 mmol), then heated to 100° C. with stirring overnight. The reaction mixture was cooled to room temperature, concentrated and dried under vacuum. The residue was diluted with ethyl acetate (100 mL), the pH was adjusted to pH 10 with saturated NaHCO₃, and then the phases were separated. The aqueous phase was extracted with ethyl acetate (2×50 mL), the combined organic phases were dried (MgSO₄), filtered and concentrated. The residue was purified by silica gel chromatography (EtOAc/hexane) to provide Intermediate A-9 (370 mg, 31%): ¹H NMR (400 MHz, DMSO-d₆) δ 9.43 (br. s., 2H), 7.70-7.63 (m, 1H), 7.33-7.22 (m, 5H), 7.10-7.03 (m, 1H), 6.91 (dd, J=6.7, 2.1 Hz, 1H), 3.87 (s, 3H): HPLC: RT=1.888 min (H₂O/MeOH with TFA, SunFire C18 2.5 μm, 2.1×30 mm, gradient=2 min, wavelength=220); MS(ES): m/z=228[M+H]⁺.

Intermediate A-10:
(2-Amino-3-chlorophenyl)(m-tolyl)methanone

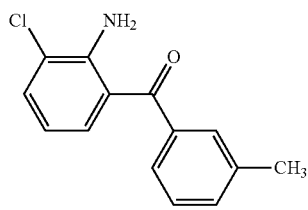

(A-10)

Intermediate A-10A:
(3-Chloro-2-nitrophenyl)(m-tolyl)methanone

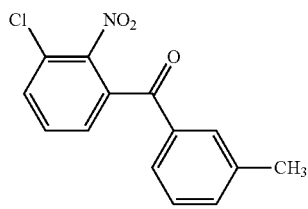

(A-10A)

A 200 mL round-bottomed flask was charged with 3-chloro-2-nitrobenzoic acid (2.5 g, 12.40 mmol) and tetrahydrofuran (50 mL). Oxalyl chloride (1.194 mL, 13.64 mmol) was added slowly followed by DMF (0.096 mL, 1.240 mmol). The reaction mixture was stirred at room temperature for 2 hrs. After cooling to 0° C., a 1M solution of m-tolylmagnesium bromide (24.81 mL, 24.81 mmol) was added. After 1 hr, another portion of m-tolylmagnesium bromide (24.81 mL, 24.81 mmol) was added. After a further hour, the reaction mixture was partitioned between ethyl acetate (200 mL) and 1N HCl (150 mL). The aqueous layer was back extracted with ethyl acetate (2×100 mL). The combined organic phases were dried with Na₂SO₄, filtered and concentrated. The crude material was purified by flash chromatography (Teledyne ISCO CombiFlash Rf, 0% to 100% solvent A/B=ethyl acetate/heptane, REDISEP® SiO₂ 120 g). Concentration of the appropriate fractions provided Intermediate A-10A (0.700 g, 21%). ¹H NMR (400 MHz, DMSO-d₆) δ 8.04 (dd, J=8.1, 1.1 Hz, 1H), 7.82 (t, J=7.9 Hz, 1H), 7.71 (dd, J=7.7, 1.1 Hz, 1H), 7.66-7.54 (m, 3H), 7.52-7.46 (m, 1H), 2.40 (s, 3H).

Intermediate A-10:
(2-Amino-3-chlorophenyl)(m-tolyl)methanone

A 100 mL round-bottomed flask, was charged with Intermediate A-10A (0.710 g, 2.58 mmol) and THF (7.5 mL). The reaction mixture was diluted with ethanol (14.75 mL) and water (3.7 mL). To this was added saturated aqueous ammonium chloride (4 mL) and iron (0.647 g, 11.59 mmol). The mixture was then heated to 100° C. with stirring. After 2 hours, the reaction mixture was filtered through CELITE® and the filtrate was partitioned between ethyl acetate (100 mL) and sat NaHCO₃ (75 mL). The aqueous layer was back extracted with ethyl acetate (1×50 mL). The combined organic phases were dried with Na₂SO₄, filtered and concentrated. The crude material was purified by flash chromatography (Teledyne ISCO CombiFlash Rf, 0% to 100% solvent A/B=ethyl acetate/heptane, REDISEP® SiO₂ 24 g). Concentration of the appropriate fractions provided Intermediate A-10 (0.417 g, 66%). $^1$H NMR (400 MHz, DMSO-d₆) δ 7.56 (dd, J=7.8, 1.4 Hz, 1H), 7.47-7.35 (m, 4H), 7.31 (dd, J=8.0, 1.4 Hz, 1H), 7.01 (s, 2H), 6.61 (t, J=7.9 Hz, 1H), 2.39 (s, 3H).

Intermediate A-11: (2-Amino-3-isopropylphenyl)(3-chlorophenyl)methanone

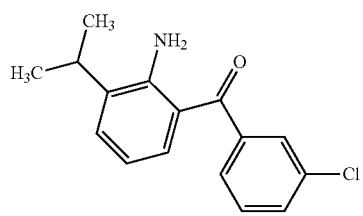

(A-11)

2-Isopropylaniline (3 mL, 21.19 mmol) was added dropwise to a 0° C. solution of trichloroborane (1M in dichloromethane) (23.31 mL, 23.31 mmol) and dichloroethane (50 mL) and the mixture was stirred for 10 min. 3-Chlorobenzonitrile (5.83 g, 42.4 mmol), followed by aluminum trichloride (3.11 g, 23.31 mmol) were added and the mixture was stirred at 0° C. for a 25 minutes. The ice bath was removed and the mixture was heated to 75° C. overnight. The mixture was cooled to room temperature. 6N HCl (60 mL, 10 eq) was cautiously added and the mixture was heated to 75° C. After 4 hrs, 12 N HCl (10 mL) was added and heating was continued overnight at 75° C. The mixture was cooled to room temperature, transferred to an Erlenmeyer flask, diluted with ethyl acetate, cooled to 0° C. and cautiously brought to pH 10 with 50% aqueous NaOH. The resulting mixture was extracted with ethyl acetate (4×). The ethyl acetate extracts were combined, washed with brine, dried over anhydrous sodium sulfate, filtered and concentrated to give a clear amber oil. The oil was suspended in a minimum of heptane and purified on an ISCO companion chromatography system (220 g silica cartridge, eluting with 0-20% ethyl acetate/heptane, 150 mL/min) to provide Intermediate A-11 (2.85 g, 10.41 mmol, 49.1% yield). HPLC RT=3.876 min 10/90 to 90/10 (MeOH/H₂O/0.1% TFA, Waters SunFire C18 3.5µ, 2.1×30 mm, 1 mL/min, 4 min gradient, wavelength=254 nm); MS(ES): m/z=274 [M+1]; $^1$H NMR (400 MHz, chloroform-d) δ 7.63 (t, J=1.7 Hz, 1H), 7.55-7.48 (m, 2H), 7.44-7.29 (m, 3H), 6.65 (t, J=7.7 Hz, 1H), 6.43 (br. s., 2H), 3.11-2.87 (m, 1H), 1.34 (d, J=6.8 Hz, 6H).

Intermediate A-12: (2-Amino-3-chlorophenyl)(phenyl)methanone

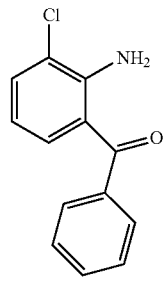

(A-12)

Intermediate A-12 was prepared according to the procedures described for Intermediate A-9. HPLC RT=2.11 min (PHENOMENEX® Luna 5 micron C18 4.6×30 mm, MeOH/H₂O/TFA, 2 min gradient, wavelength=254 nm). [M+H]⁺=232.

Intermediate B-1: (S)-3-Amino-9-methyl-5-phenyl-1H-benzo[e][1,4]diazepin-2(3H)-one

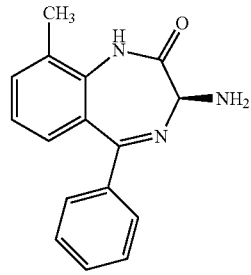

(B-1)

Intermediate B-1A: (S)-Benzyl (9-methyl-2-oxo-5-phenyl-2,3-dihydro-1H-benzo[e][1,4]diazepin-3-yl)carbamate

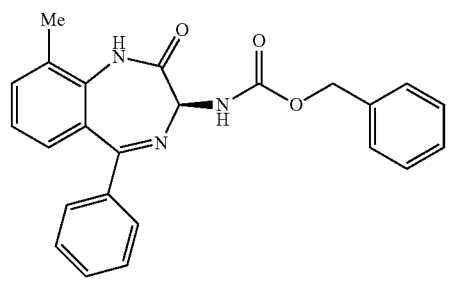

(B-1A)

A suspension of 2-(1H-benzo[d][1,2,3]triazol-1-yl)-2-(((benzyloxy)carbonyl)amino)acetic acid (J. Org. Chem., 55:2206-2214 (1990)) (17.30 g, 53.0 mmol) in THF (128 mL) was cooled to 0° C. Oxalyl chloride (4.64 mL, 53.0 mmol) was added, followed by 50 μL DMF. The reaction mixture was stirred for 2 h at 0° C. A solution of Intermediate A-4 (5.09 g, 24.09 mmol) and N-methyl morpholine (7.95 ml, 72.3 mmol) was added, and the reaction mixture was allowed to warm gradually to room temperature. After 2.5 h ammonia (7 M in MeOH) (21.29 ml, 149 mmol) was added and the reaction mixture was stirred overnight. The resulting mixture was diluted with EtOAc (250 mL), and then washed with $H_2O$ (250 mL), 1 M NaOH (250 mL), and brine (250 mL). The organic layer was concentrated and then suspended in acetic acid (48.2 ml). Ammonium acetate (9.29 g, 120 mmol) was added. After 2.5 hours, $H_2O$ was added to precipitate the product resulting in a sticky solid. The solid was collected by filtration and suspended in a minimal amount of MeOH and cooled to 0° C. The resulting white solid was collected by filtration, washed with cold MeOH and then diethyl ether. The resulting material was dried under vacuum. The mixture of enantiomers was separated using SFC (Berger SFC MGII, CHIRALCEL® OJ-H 25×3 cm, 5 cm, 70/30 $CO_2$/MeOH, 200 mL/min, detection at 220 nm) to afford the desired compound Intermediate B-1A (1.6 g, 16.63%). HPLC RT=2.773 min (CHROMOLITH® SpeedROD, 5.0 μm, 4.6 mm×50 mm, 10-90% aqueous methanol containing 0.1% TFA, 4 min gradient, monitored at 220 nm). [M+H$^+$]=400.4. $^1$H NMR (400 MHz, DMSO-d$_6$) δ 8.35 (d, J=8.6 Hz, 1H), 7.56-7.37 (m, 11H), 7.23-7.17 (m, 1H), 7.16-7.12 (m, 1H), 5.12-4.99 (m, 3H), 2.42 (s, 3H).

Intermediate B-1

A solution of Intermediate B-1A (1.6 g, 4.01 mmol) in 33% HBr in HOAc (6.59 ml, 40.1 mmol) was stirred at room temperature for 2 hr. Ether (100 mL) was added and the resulting yellow suspension was cooled to 0° C. for 1 h. The resulting solid was collected by filtration and rinsed with ether. The hygroscopic solid was then dissolved in MeOH, concentrated to dryness and dried under vacuum. The solid (HBr salt) was triturated and sonicated with hexane (with a little of EtOAc, to remove residual HOAc), the solid was collected by filtration, and dried under vacuum to afford the desired product. HPLC RT=1.378 min (CHROMOLITH® SpeedROD, 5.0 μm, 4.6 mm×50 mm, 10-90% aqueous methanol containing 0.1% TFA, 4 min gradient, monitored at 220 nm). [M+H$^+$]=266.4. $^1$H NMR (400 MHz, DMSO-d$_6$) δ 10.63 (s, 1H), 8.99 (br. s., 3H), 7.64-7.45 (m, 6H), 7.28-7.22 (m, 1H), 7.20-7.15 (m, 1H), 5.05 (d, J=4.6 Hz, 1H), 2.43 (s, 3H).

The compounds listed below in Table 2 (Intermediates B-2-B-4) were prepared according to the general synthetic procedure described for Intermediate B-1, using the appropriate aminobenzophenone.

TABLE 2

| Int. | Structure | Name | HPLC RT (min) | LC/MS [M + H]$^+$ | Starting Material |
| --- | --- | --- | --- | --- | --- |
| B-2[a] | 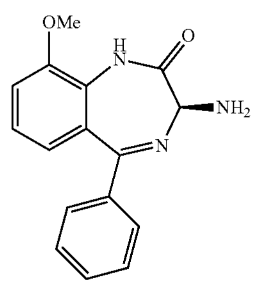 [SMILES: COc1cccc2c1NC(=O)[C@@H](N)N=C2c1ccccc1] | (S)-3-amino-9-methoxy-5-phenyl-1H-benzo[e][1,4]diazepin-2(3H)-one | 3.21[1] | 282 | A-9 |
| B-3[b] | 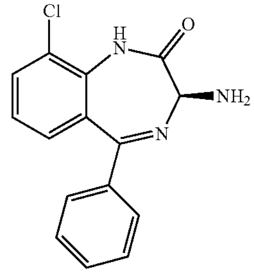 [SMILES: N[C@H]1N=C(c2ccccc2)c2cccc(Cl)c2NC1=O] | (S)-3-amino-9-chloro-5-phenyl-1H-benzo[e][1,4]diazepin-2(3H)-one | 0.63[2] | 286 | A-12 |

TABLE 2-continued

| Int. | Structure | Name | HPLC RT (min) | LC/MS [M + H]+ | Starting Material |
|---|---|---|---|---|---|
| B-4[c] | 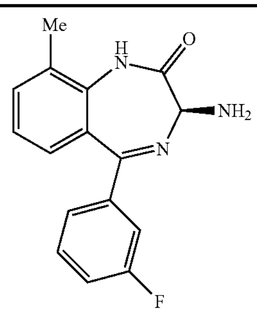 | (S)-3-amino-5-(3-fluorophenyl)-9-methyl-1H-benzo[e][1,4]diazepin-2(3H)-one | 1.72[3] | 284.2 | A-3 |

[1]Luna C18 4.6 × 30 mm 3 μ H$_2$O/MeOH TFA, gradient = 5 min, wavelength = 220 nm.
[2]BEH C18 2.1 × 50 mm 1.7 μ; H$_2$O/CH$_3$CN TFA, gradient = 1 min, wavelength = 220 nm.
[3]H$_2$O/MeOH with TFA, CHROMOLITH® ODS S5, 4.6 × 50 mm, gradient = 4 min, wavelength = 220 nm.
Chiral Separation Conditions:
[a]Instrument: Berger SFC MGII, Lux Cell-4 25 × 5 cm, 5 cm, 60/40 CO$_2$/MeOH, 180 mL/min, detection at 220 nm.
[b]Instrument: Berger SFC MGII, Lux Cell-4 25 × 5 cm, 5 cm, 70/30 CO$_2$/MeOH, 180 mL/min, detection at 220 nm.
[c]Instrument: Berger SFC MGII, Chiral IC 25 × 3 cm, 5 cm, 150/45 CO$_2$/MeOH, 180 mL/min, detection at 220 nm.

The compounds listed below in Table 3 (Intermediates B-5-B-10) were prepared according to the synthetic procedure described for Intermediate B-1, using the indicated aminobenzophenone. However, the final chiral separation was not attempted and the racemates were used in subsequent steps.

TABLE 3

| (Racemic Cores) | | | | | |
|---|---|---|---|---|---|
| Int. | Structure | Name | HPLC RT (min) | LC/MS [M + H]+ | Starting Material |
| B-5 | | (S)-3-amino-9-fluoro-5-phenyl-1H-benzo[e][1,4]diazepin-2(3H)-one | 1.295 | 270 | A-7 |
| B-6 | | 3-amino-9-cyclopropoxy-5-(3-fluorophenyl)-1H-benzo[e][1,4]diazepin-2(3H)-one | 2.251 | 326.2 | A-1 |

TABLE 3-continued (Racemic Cores)

| Int. | Structure | Name | HPLC RT (min) | LC/MS [M + H]⁺ | Starting Material |
|---|---|---|---|---|---|
| B-7 | 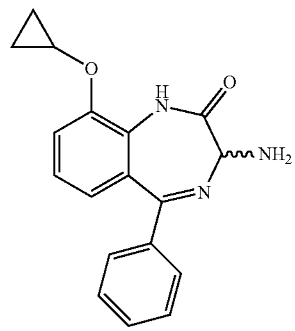 [SMILES: NC1N=C(c2ccccc2)c2cccc(OC3CC3)c2NC1=O] | 3-amino-9-cyclopropoxy-5-phenyl-1H-benzo[e][1,4]diazepin-2(3H)-one | 2.181 | 308.1 | A-2 |
| B-8 | 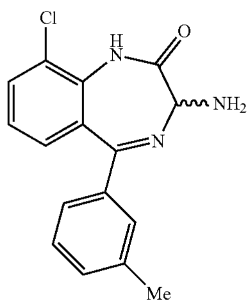 [SMILES: Cc1cccc(C2=NC(N)C(=O)Nc3c(Cl)cccc32)c1] | 3-amino-9-chloro-5-(m-tolyl)-1H-benzo[e][1,4]diazepin-2(3H)-one | 1.472 | 300 | A-10 |
| B-9 | 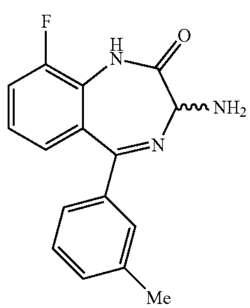 [SMILES: Cc1cccc(C2=NC(N)C(=O)Nc3c(F)cccc32)c1] | 3-amino-9-fluoro-5-(m-tolyl)-1H-benzo[e][1,4]diazepin-2(3H)-one | 0.613 | 284 | A-8 |
| B-10 | 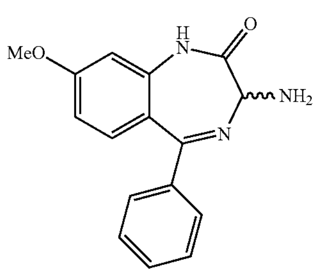 [SMILES: COc1ccc2c(c1)NC(=O)C(N)N=C2c1ccccc1] | 3-amino-8-methoxy-5-phenyl-1H-benzo[e][1,4]diazepin-2(3H)-one | 1.574 | 282.2 | A-6 |

[1] MeOH/H₂O/0.1% TFA, Waters SunFire C18 3.5 μ, 2.1 × 30 mm, 1 mL/min, 4 min gradient, wavelength = 254 nm.

[2] H₂O/CH₃CN with TFA, SunFire C18 3.5 μm, 2.1 × 30 mm, gradient = 2 min, wavelength = 220 nm.

[3] H₂O/MeOH with TFA, BEH C18 1.7 μm, 2.1 × 50 mm, gradient = 2 min, wavelength = 220 nm.

[4] H₂O/MeOH with TFA, PHENOMENEX ® C18, 2.5 μm, 2.0 × 30 mm, gradient = 2 min, wavelength = 220 and 254 nm.

[5] H₂O/MeOH with TFA, CHROMOLITH ® ODS S5, 4.6 × 50 mm, gradient = 4 min, wavelength = 220 nm.

Intermediate B-11: 3-(S)-3-Amino-9-cyclopropyl-5-phenyl-1H-benzo[e][1,4]diazepin-2(3H)-one

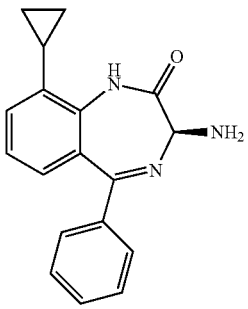

(B-11)

Intermediate B-11A: Benzyl (9-bromo-2-oxo-5-phenyl-2,3-dihydro-1H-benzo[e][1,4]diazepin-3-yl)carbamate

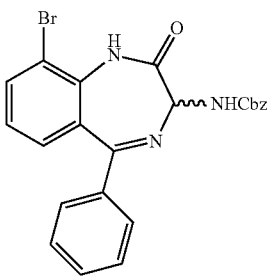

(B-11A)

Intermediate B-11A was prepared from Intermediate A-5 by the general procedure given for Intermediate B-1. HPLC: RT=2.048 min (H₂O/MeOH with TFA, Ascentis Express C18 2.7 μm, 2.1×50 mm, gradient=4 min, wavelength=220 nm); MS(ES):m/z=464 [M+H⁺].

Intermediate B-11B: Benzyl (9-cyclopropyl-2-oxo-5-phenyl-2,3-dihydro-1H-benzo[e][1,4]diazepin-3-yl)carbamate

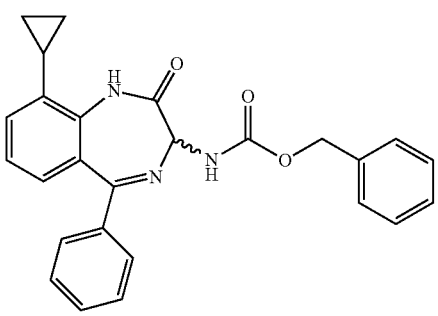

(B-11B)

To a stirred mixture of Intermediate B-11A (2.00 g, 4.31 mmol), palladium dichloride dppf (946 mg, 1.29 mmol), potassium phosphate dibasic (2.25 g, 12.9 mmol) and cyclopropylboronic acid methyliminodiacetic acid ester (1.70 g, 8.61 mmol) in dioxane (12 mL) under nitrogen was added water (3 mL). The reaction mixture was heated at 85° C. for 20 h and then cooled to room temperature. The mixture was diluted with EtOAc (40 mL) and filtered through a 1' pad of silica gel which was topped by a ½' pad of CELITE®. This was further eluted with EtOAc. The filtrate was concentrated under reduced pressure and purified by flash chromatography (Teledyne ISCO CombiFlash 0% to 17% solvent A/B=DCM/Acetone, REDISEP® SiO₂ 120 g, detecting at 254 nM, and monitoring at 220 nM). Concentration of appropriate fractions provided Intermediate B-11B (1.20 g, 65%). HPLC: RT=3.246 min (CHROMOLITH® SpeedROD column 4.6×50 mm, 10-90% aqueous methanol over 4 minutes containing 0.1% TFA, 4 mL/min, monitoring at 220 nm). MS(ES):m/z=426.1 [M+H⁺]; ¹H NMR (400 MHz, DMSO-d₆) δ 10.29 (s, 1H), 8.38 (d, J=8.6 Hz, 1H), 7.57-7.32 (m, 10H), 7.30 (d, J=7.5 Hz, 1H), 7.20 (t, J=7.6 Hz, 1H), 7.11 (d, J=7.3 Hz, 1H), 5.08 (s, 2H), 5.04 (d, J=8.4 Hz, 1H), 2.26-2.13 (m, 1H), 1.09-0.95 (m, 2H), 0.87-0.78 (m, 1H), 0.61-0.52 (m, 1H).

Intermediate B-11

Intermediate B-11 was prepared from Intermediate B-11B by treatment with 33% HBr/acetic acid according to the general procedure detailed for Intermediate B-1. The racemate was separated by SFC chromatography (Instrument: Berger SFC MGII, Chiral OD 25×3 cm ID, 5 μm, 82/18 CO₂/MeOH, 85 mL/min, detection at 220 nm). HPLC: RT=2.085 min (CHROMOLITH® SpeedROD column 4.6×50 mm, 10-90% aqueous methanol over 4 minutes containing 0.1% TFA, 4 mL/min, monitoring at 220 nm). LC/MS: M+H=292.1. ¹H NMR (400 MHz, DMSO-d₆) δ 10.78 (s, 1H), 9.01 (br. s., 3H), 7.65-7.48 (m, 5H), 7.38 (dd, J=7.6, 1.2 Hz, 1H), 7.26 (t, J=7.8 Hz, 1H), 7.19-7.14 (m, 1H), 2.27-2.16 (m, 1H), 1.14-0.98 (m, 2H), 0.91-0.80 (m, 1H), 0.67-0.56 (m, 1H).

Intermediate B-12: (3S)-3-Amino-5-phenyl-1,3-dihydro-2H-1,4-benzodiazepin-2-one

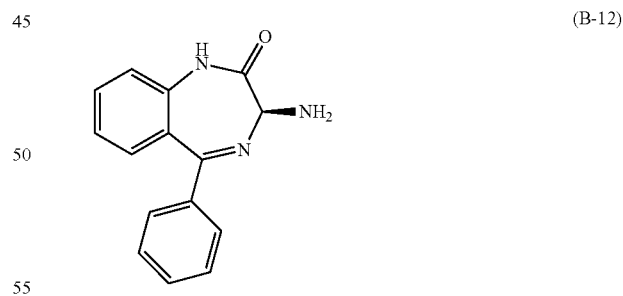

(B-12)

Racemic 3-amino-5-phenyl-1,3-dihydro-2H-1,4-benzodiazepin-2-one (*J. Med. Chem.*, 49:2311-2319 (2006), compound #5) was prepared according to the literature procedure. The enantiomers were separated on Berger SFC MGIII Column: Lux 25×3 cm, 5 cm; Mobile Phase: 30% MeOH+ 0.1% DEA in CO₂; Flow rate: 150 mL/min; Temperature: 40° C.; Detector wavelength: 250 nM. Obtained the S-enantiomer Intermediate B-12 as a white solid: ¹H NMR (400 MHz, DMSO-d₆) δ ppm 10.67 (1H, br. s.), 7.58 (1H, td, J=7.65, 1.76 Hz), 7.37-7.53 (5H, m), 7.23-7.30 (2H, m), 7.14-7.22 (1H, m), 4.23 (1H, s), 2.60 (2H, br. s.); HPLC:

RT=3.0625 min (30% MeOH+0.1% DEA in CO₂ on OD-H Column, 3 mL/min, 35° C., 96 bar, 230 nm, 10 µl in); [α]$_D$=−208.3° (5.05 mg/mL, MeOH).

Intermediate B-13: (S)-3-Amino-9-fluoro-5-phenyl-1H-benzo[e][1,4]diazepin-2(3H)-one

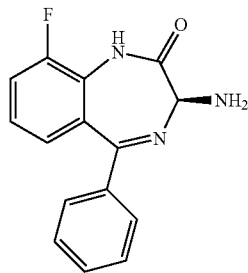

(B-13)

Intermediate B-13 was prepared from Intermediate A-7 according to the general procedure detailed for Intermediate B-1. The individual enantiomers were separated after the deprotection step (Berger SFC MGIII Chiral IA 25×2 cm ID, 5 µm; Mobile Phase: 15% MeOH in CO₂; Flow rate: 60 mL/min; Temperature: 30° C.; Detector wavelength: 220 nm) and then treated with 1N HCl to afford Intermediate B-13 as an HCl salt. HPLC: RT=1.29 min (H₂O/MeOH with TFA, CHROMOLITH® ODS S5, 4.6×50 mm, gradient=4 min, wavelength=220 nm). LC/MS: M+H=270. ¹H NMR (400 MHz, DMSO-d₆) δ 11.27 (br. s., 1H), 9.08 (br. s., 3H), 7.75-7.47 (m, 6H), 7.42-7.29 (m, 1H), 7.17 (s, 1H), 5.21 (s, 1H).

Example 1

(2R,3S)-3-((3,3-Difluorocyclobutyl)methyl)-N-((3S)-9-methyl-2-oxo-5-phenyl-2,3-dihydro-1H-1,4-benzodiazepin-3-yl)-2-(3,3,3-trifluoropropyl)succinamide

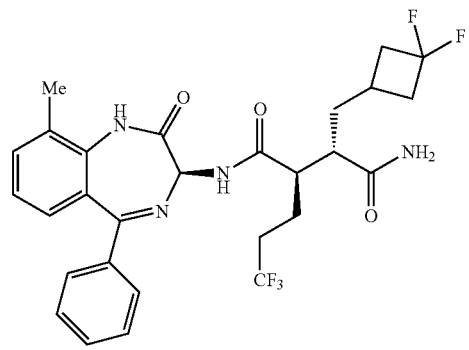

(1)

Example 1A (2S,3R)-tert-Butyl 2-((3,3-difluorocyclobutyl)methyl)-6,6,6-trifluoro-3-(((S)-9-methyl-2-oxo-5-phenyl-2,3-dihydro-1H-benzo[e][1,4]diazepin-3-yl)carbamoyl)hexanoate

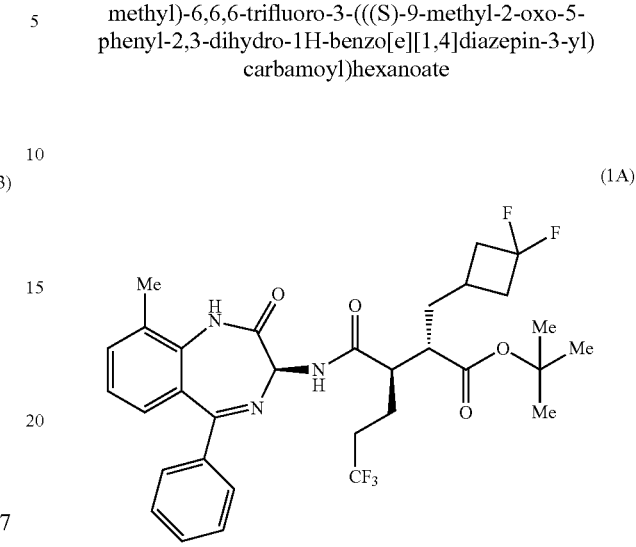

(1A)

To a solution of Intermediate B-1, 2 hydrobromide (308 mg, 0.721 mmol), Intermediate S-1 (225 mg, 0.601 mmol) and TBTU (289 mg, 0.902 mmol) in DMF (4 mL) was added TEA (0.335 mL, 2.404 mmol). The mixture was stirred at room temperature for 50 min. A dilute solution of NaHCO₃ was added while stirring. The resulting solid was collected by filtration, rinsed with water, dried and then purified by silica gel chromatography (12 g column, EtOAc/hexane=0-70%) to give Example 1A (327 mg, 99% yield). HPLC: RT=3.400 min (H₂O/MeOH with TFA, CHROMOLITH® SpeedROD, 4.6×50 mm, gradient=4 min, wavelength=220 nm) MS(ES):m/z=622 [M+H⁺].

Example 1

A solution of Example 1A (370 mg, 0.595 mmol) in TFA/DCM (4 mL, 1/1) was stirred at room temperature for 1 h. The reaction mixture was then diluted with toluene, concentrated, and azeotroped with DCM/toluene two additional times. The resulting solid was dried under high vacuum. The residue was dissolved in THF (8 mL), and HOBT (319 mg, 2.083 mmol) was added and the mixture was stirred for 5 min. Then EDC (399 mg, 2.083 mmol) was added and stirring continued for an additional 5 min. 2N ammonia (2.381 mL, 4.76 mmol) was then added. The reaction mixture was stirred at room temperature overnight and the concentrated. Water was added to the stirring residue and the mixture was sonicated. The resulting solid was collected by filtration, rinsed with water and then dried. The solid was purified by silica gel chromatography (12 g column, EtOAc/hexane=0-100) to give Example 1 as a white solid (237 mg, 71% yield). HPLC: RT=2.711 min (H₂O/MeOH with TFA, CHROMOLITH® SpeedROD, 4.6×50 mm, gradient=4 min, wavelength=220 nm) MS(ES): m/z=565 [M+H⁺]; ¹H NMR (400 MHz, methanol-d₄) δ 7.63-7.48 (m, 4H), 7.47-7.40 (m, 2H), 7.21 (s, 2H), 5.38 (s, 1H), 2.77 (td, J=10.5, 4.0 Hz, 1H), 2.73-2.58 (m, 2H), 2.56-2.42 (m, 5H), 2.34-2.06 (m, 5H), 2.02-1.91 (m, 1H), 1.88-1.70 (m, 2H), 1.70-1.60 (m, 1H).

Example 2

(2R,3S)-3-(4,4-Difluorocyclohexyl)-N-((3S)-9-methoxy-2-oxo-5-phenyl-2,3-dihydro-1H-1,4-benzodiazepin-3-yl)-2-(3,3,3-trifluoropropyl)succinamide

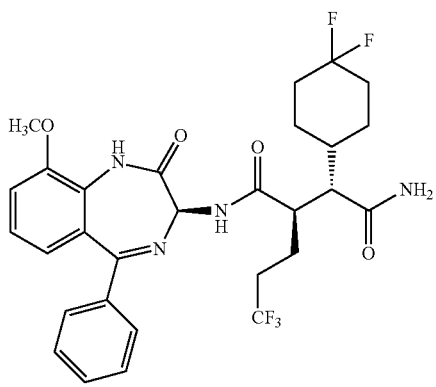

(2)

Example 2 was prepared from Intermediate B-2 and Intermediate S-3 according to the general procedure shown for Example 1. Example 2 was obtained HPLC: RT=10.27 min (H$_2$O/CH$_3$CN with TFA, SunFire C18 3.5 µm, 4.6×150 mm, gradient=15 min, wavelength=220 and 254 nm); MS(ES):m/z=595 [M+H$^+$]; $^1$H NMR (400 MHz, methanol-d$_4$) δ 10.08 (s, 1H), 9.48 (d, J=7.5 Hz, 1H), 7.60-7.42 (m, 5H), 7.38-7.19 (m, 2H), 6.96 (br. s., 1H), 6.92-6.83 (m, 1H), 5.27 (d, J=7.5 Hz, 1H), 3.94 (s, 2H), 3.05-2.89 (m, 1H), 2.57 (d, J=5.1 Hz, 1H), 2.31-2.19 (m, 1H), 2.10-1.90 (m, 3H), 1.87-1.75 (m, 1H), 1.73-1.41 (m, 5H), 1.37-1.22 (m, 1H).

Example 3

(2R,3S)—N-((3S)-9-(Cyclopropyloxy)-5-(3-fluorophenyl)-2-oxo-2,3-dihydro-1H-1,4-benzodiazepin-3-yl)-3-(4,4-difluorocyclohexyl)-2-(3,3,3-trifluoropropyl)succinamide

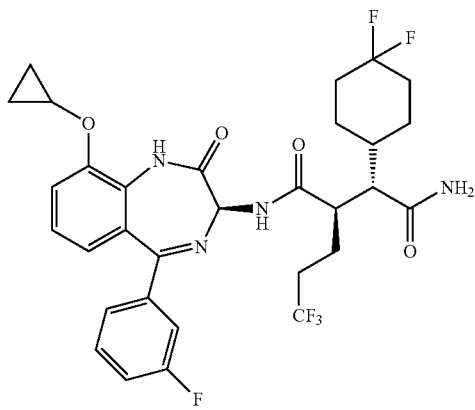

(3)

Example 3 was prepared from Intermediate B-6 and Intermediate S-3 according to the general procedure shown for Example 1. This solid was purified by preparative SFC chromatography (Welk O(RR) 250×30 mm ID, 5 µm, 84/16 CO$_2$/MeOH, 120 mL/min) to give Example 3. HPLC: RT=10.95 min (H$_2$O/CH$_3$CN with TFA, SunFire C18 3.5 µm, 4.6×150 mm, gradient=15 min, wavelength=220 and 254 nm); MS(ES):m/z=639 [M+H$^+$]; $^1$H NMR (400 MHz, methanol-d$_4$) δ 10.05 (s, 1H), 9.47 (d, J=7.3 Hz, 1H), 7.60 (dd, J=8.3, 1.2 Hz, 1H), 7.55-7.45 (m, 2H), 7.44-7.24 (m, 4H), 6.94 (dd, J=7.9, 1.1 Hz, 2H), 5.27 (d, J=7.3 Hz, 1H), 4.03 (tt, J=5.9, 2.9 Hz, 1H), 3.05-2.91 (m, 1H), 2.32-2.17 (m, 1H), 2.00 (d, J=12.1 Hz, 4H), 1.77-1.41 (m, 8H), 1.38-1.20 (m, 2H), 0.99-0.92 (m, 1H), 0.90-0.81 (m, 2H), 0.80-0.67 (m, 1H).

Example 4

(2R,3S)—N-((3S)-9-Chloro-2-oxo-5-phenyl-2,3-dihydro-1H-1,4-benzodiazepin-3-yl)-3-(4-(trifluoromethyl)cyclohexyl)-2-(3,3,3-trifluoropropyl)succinamide

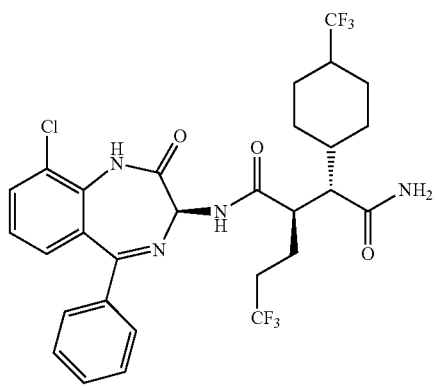

(4)

Example 4 was prepared from Intermediate B-3 and Intermediate S-8 according to the general procedure shown for Example 1. This solid was purified by preparative SFC chromatography (OD 250×30 mm ID, 5 µm, 85/15 CO$_2$/MeOH, 200 mL/min) to give Example 4 as a single diastereomer with unknown stereochemistry. HPLC: RT=9.56 min (H$_2$O/CH$_3$CN with TFA, SunFire C18 3.5 µm, 4.6×150 mm, gradient=15 min, wavelength=220 and 254 nm); MS(ES): m/z=631 [M+H$^+$]; $^1$H NMR (400 MHz, methanol-d$_4$) δ 10.47 (br. s., 1H), 9.46 (d, J=7.0 Hz, 1H), 7.90-7.81 (m, 1H), 7.61-7.50 (m, 3H), 7.50-7.40 (m, 3H), 7.33 (d, J=3.7 Hz, 2H), 6.92 (br. s., 1H), 5.31 (d, J=7.0 Hz, 1H), 3.08-2.96 (m, 1H), 2.50-2.42 (m, 2H), 2.32-2.00 (m, 2H), 1.89 (t, J=12.3 Hz, 2H), 1.74 (d, J=12.5 Hz, 1H), 1.66-1.53 (m, 2H), 1.41 (d, J=9.5 Hz, 1H), 1.35-1.07 (m, 5H).

Example 5

(2R,3S)—N-((3S)-9-Chloro-2-oxo-5-phenyl-2,3-dihydro-1H-1,4-benzodiazepin-3-yl)-3-(4,4-difluorocyclohexyl)-2-(3,3,3-trifluoropropyl)succinamide (5)

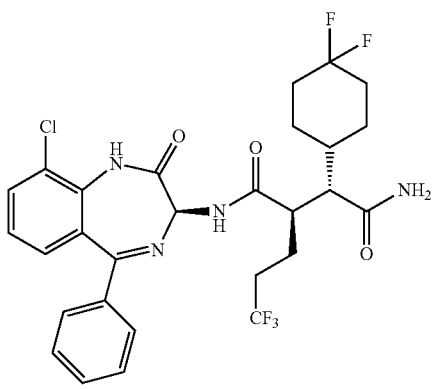

Example 5 was prepared from Intermediate B-3 and Intermediate S-3 according to the general procedure shown for Example 1. This solid was purified by preparative SFC chromatography (Berger SFC MGII, Whelk—O1 AS-H 250×30 mm ID, 5 μm, 85/15 CO$_2$/MeOH, 85 mL/min) to give Example 5. HPLC: RT=9.21 min (H$_2$O/CH$_3$CN with TFA, SunFire C18 3.5 μm, 4.6×150 mm, gradient=15 min, wavelength=220 and 254 nm); MS(ES):m/z=599 [M+H$^+$]; $^1$H NMR (400 MHz, methanol-d$_4$) δ 10.47 (br. s., 1H), 9.50 (br. s., 1H), 7.84 (br. s., 1H), 7.63-7.42 (m, 6H), 7.32 (br. s., 2H), 6.96 (s, 1H), 5.30 (br. s., 1H), 3.09-2.92 (m, 1H), 2.26 (br. s., 1H), 2.00 (d, J=11.2 Hz, 4H), 1.74-1.56 (m, 6H), 1.40-1.19 (m, 3H).

Example 6

(2R,3S)-3-((3,3-Difluorocyclobutyl)-N-((3S)-2-oxo-5-phenyl-2,3-dihydro-1H-1,4-benzodiazepin-3-yl)-2-(3,3,3-trifluoropropyl)succinamide (6)

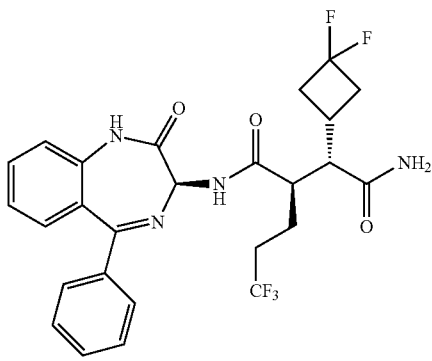

Example 6 was prepared from Intermediate B-12 and Intermediate S-9 according to the general procedure shown for Example 1. The mixture of diastereomers was separated by preparative HPLC (Gemini C18 25×2 cm ID, 5 μm, 60/40 to 25/75 water/ACN with 0.1% TFA in 10 min, hold for 2 min, 20.0 mL/min) to give Example 6. HPLC RT=2.24 min (PHENOMENEX® Luna 5 micron C18 4.6×30 mm, 30 to 100 B in 4 min with 1 min hold time, Flow rate=5 ml/min, detection at 254 nm, Solvent A: 10% methanol/90% water 0.1% TFA; Solvent B: 10% water 90% methanol 0.1% TFA), (M+H=537.29). $^1$H NMR (500 MHz, methanol-d$_4$) δ 7.66-7.59 (m, 2H), 7.57-7.53 (m, 2H), 7.52-7.47 (m, 1H), 7.45-7.39 (m, 2H), 7.37 (dd, J=7.9, 1.2 Hz, 1H), 7.32 (d, J=8.3 Hz, 1H), 7.28-7.22 (m, 1H), 5.39 (s, 1H), 2.83-2.73 (m, 2H), 2.59 (t, J=9.4 Hz, 2H), 2.54-2.15 (m, 6H), 1.87-1.77 (m, 1H), 1.76-1.66 (m, 2H).

Example 7

(2R,3S)—N-((3S)-9-(Cyclopropyloxy)-2-oxo-5-phenyl-2,3-dihydro-1H-1,4-benzodiazepin-3-yl)-3-((3,3-difluorocyclobutyl)methyl)-2-(3,3,3-trifluoropropyl)succinamide (7)

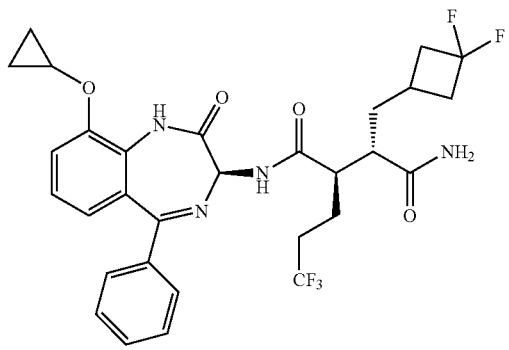

Example 7 was prepared from Intermediate B-7 and Intermediate S-1 according to the general procedure shown for Example 1. After separation of the diastereomers (Berger SFC MGII, Regis Whelk—O R,R 25×3 cm ID, 5 μm, 80/20 CO$_2$/MeOH, 85 mL/min, detection at 220 nm), Example 7 was obtained. HPLC: RT=10.714 min (H$_2$O/CH$_3$CN with TFA, SunFire C18 3.5 μm, 4.6×150 mm, gradient=15 min, wavelength=220 and 254 nm); MS(ES):m/z=607 [M+H$^+$]; $^1$H NMR (400 MHz, methanol-d$_4$) δ 7.65-7.47 (m, 1H), 7.49-7.36 (m, 1H), 7.25 (t, J=8.1 Hz, 1H), 6.95 (dd, J=7.9, 1.1 Hz, 1H), 5.40 (s, 1H), 4.06-3.89 (m, 1H), 2.88-2.40 (m, 5H), 2.35-1.55 (m, 8H), 1.01-0.81 (m, 4H).

Example 8

(2R,3S)-3-((3,3-Difluorocyclobutyl)methyl)-N-((3S)-9-methoxy-2-oxo-5-phenyl-2,3-dihydro-1H-1,4-benzodiazepin-3-yl)-2-(3,3,3-trifluoropropyl)succinamide (8)

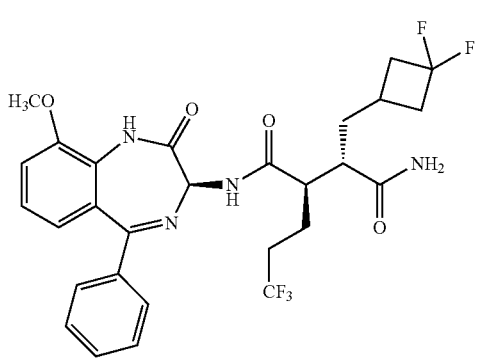

Example 8 was prepared from Intermediate B-2 and Intermediate S-1 according to the general procedure shown for Example 1 to afford Example 8. HPLC: RT=10.99 min (H₂O/CH₃CN with TFA, SunFire C18 3.5 μm, 4.6×150 mm, gradient=15 min, wavelength=220 and 254 nm); MS(ES): m/z=581.5 [M+H⁺]; ¹H NMR (400 MHz, chloroform-d) δ 8.05 (s, 1H), 7.55-7.49 (m, 2H), 7.49-7.44 (m, 1H), 7.42-7.33 (m, 1H), 7.21-7.12 (m, 1H), 7.11-7.05 (m, 1H), 6.98 (dd, J=7.9, 1.3 Hz, 1H), 5.84 (br. s., 1H), 5.53 (m, 2H), 3.99 (s, 3H), 2.79-2.56 (m, 3H), 2.51-2.42 (m, 1H), 2.35-2.06 (m, 6H), 1.96-1.74 (m, 3H).

Example 9

(2R,3S)-3-((3,3-Difluorocyclobutyl)methyl)-N-((3S)-5-(3-fluorophenyl)-9-methyl-2-oxo-2,3-dihydro-1H-1,4-benzodiazepin-3-yl)-2-(3,3,3-trifluoropropyl)succinamide

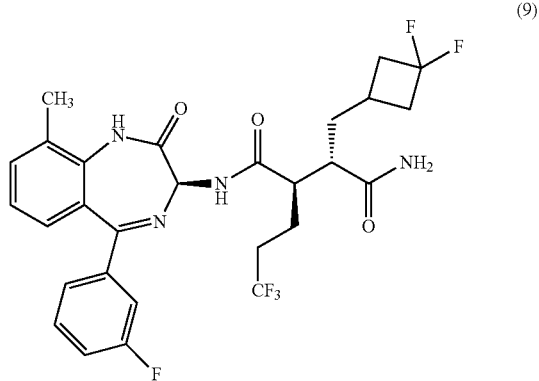 [SMILES: Cc1cccc2c1NC(=O)[C@@H](NC(=O)[C@H](CCC(F)(F)F)[C@H](CC1CC(F)(F)C1)C(N)=O)N=C2c1cccc(F)c1]

(9)

Example 9 was prepared from Intermediate B-4 and Intermediate S-1 according to the general procedure shown for Example 1 to afford Example 9. HPLC: RT=10.653 min (H₂O/CH₃CN with TFA, Xbridge Phenyl 3.5 μm, 3×150 mm, gradient=15 min, wavelength=220 and 254 nm); MS(ES):m/z=583.4 [M+H⁺]; ¹H NMR (400 MHz, methanol-d₄) δ 7.56-7.50 (m, 1H), 7.47-7.40 (m, 1H), 7.39-7.32 (m, 2H), 7.28-7.22 (m, 1H), 7.22-7.18 (m, 2H), 5.36 (s, 1H), 2.75 (td, J=10.5, 4.2 Hz, 1H), 2.70-2.57 (m, 2H), 2.56-2.41 (m, 5H), 2.29-2.04 (m, 4H), 1.98-1.87 (m, 1H), 1.86-1.68 (m, 2H), 1.67-1.57 (m, 1H).

Example 10

(2R,3S)—N-((3S)-9-Chloro-5-(3-methylphenyl)-2-oxo-2,3-dihydro-1H-1,4-benzodiazepin-3-yl)-3-((3,3-difluorocyclobutyl)methyl)-2-(3,3,3-trifluoropropyl)succinamide

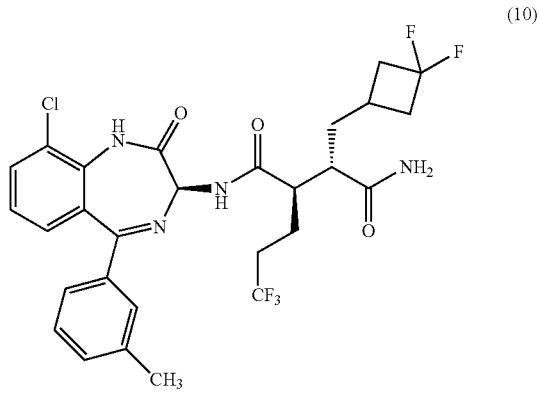 [SMILES: Cc1cccc(C2=N[C@H](NC(=O)[C@H](CCC(F)(F)F)[C@H](CC3CC(F)(F)C3)C(N)=O)C(=O)Nc3c(Cl)cccc32)c1]

(10)

Example 10 was prepared from Intermediate B-8 and Intermediate S-1 according to the general procedure shown for Example 1. After separation of the diastereomers (Instrument: Berger SFC MGIII, Column: CHIRALPAK® IC 25×3 cm, 5 μm; Mobile Phase: 88/12 CO₂/MeOH Flow rate: 85 mL/min; Detection at 220 nm), Example 10 was obtained. HPLC: RT=10.578 min (H₂O/CH₃CN with TFA, SunFire C18 3.5 μm, 4.6×150 mm, gradient=15 min, wavelength=220 and 254 nm); MS(ES):m/z=599.3 [M+H⁺]; ¹H NMR (400 MHz, methanol-d₄) δ 7.79 (dd, J=7.7, 1.5 Hz, 1H), 7.44 (s, 1H), 7.39-7.23 (m, 5H), 5.40 (s, 1H), 2.77 (td, J=10.4, 4.1 Hz, 1H), 2.72-2.60 (m, 2H), 2.57-2.44 (m, 2H), 2.38 (s, 3H), 2.32-2.08 (m, 4H), 2.01-1.89 (m, 1H), 1.88-1.70 (m, 2H), 1.68-1.57 (m, 1H).

Example 11

(2R,3S)-3-((3,3-Difluorocyclobutyl)methyl)-N-((3S)-9-fluoro-5-(3-methylphenyl)-2-oxo-2,3-dihydro-1H-1,4-benzodiazepin-3-yl)-2-(3,3,3-trifluoropropyl)succinamide

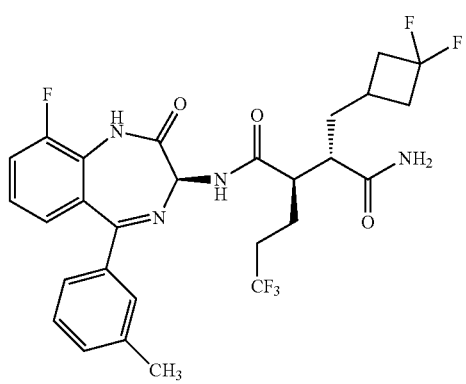

(11)

Example 11 was prepared from Intermediate B-9 and Intermediate S-1 according to the general procedure shown for Example 1. After separation of the diastereomers (Instrument: Berger SFC MGIII, Column: PHENOMENEX® Lux Cellulose-4 25×3 cm ID, 5 μm; Mobile Phase: 85/15 CO₂/MeOH Flow rate: 85 mL/min; Detection at 220 nm), Example 11 was obtained. HPLC: RT=10.984 min (H₂O/CH₃CN with TFA, Xbridge Phenyl 3.5 μm, 3×150 mm, gradient=15 min, wavelength=220 and 254 nm); MS(ES): m/z=583.3 [M+H⁺]; ¹H NMR (400 MHz, methanol-d₄) δ 7.50-7.43 (m, 1H), 7.41 (s, 1H), 7.36-7.21 (m, 4H), 7.17 (d, J=7.9 Hz, 1H), 5.43 (s, 1H), 2.75 (td, J=10.5, 4.2 Hz, 1H), 2.71-2.57 (m, 2H), 2.55-2.42 (m, 2H), 2.36 (s, 3H), 2.30-2.05 (m, 4H), 1.99-1.88 (m, 1H), 1.86-1.69 (m, 2H), 1.67-1.57 (m, 1H).

Example 12

(2R,3S)—N-((3S)-9-Cyclopropyl-2-oxo-5-phenyl-2,3-dihydro-1H-1,4-benzodiazepin-3-yl)-3-((3,3-difluorocyclobutyl)methyl)-2-(3,3,3-trifluoropropyl)succinamide

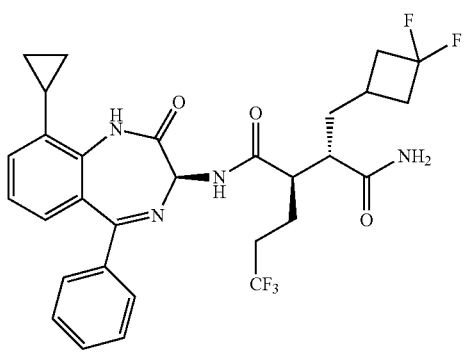

(12)

Example 12 was prepared from Intermediate B-11 and Intermediate S-1 according to the general procedure shown for Example 1. Example 12 was obtained. HPLC: RT=8.551 min (H₂O/CH₃CN with TFA, SunFire C18 3.5 μm, 4.6×150 mm, gradient=15 min, wavelength=220 and 254 nm); MS(ES):m/z=591.5 [M+H⁺]; $^1$H NMR (400 MHz, methanol-$d_4$) δ 7.63-7.48 (m, 3H), 7.47-7.36 (m, 3H), 7.26-7.17 (m, 2H), 5.39 (s, 1H), 2.78 (td, J=10.5, 4.0 Hz, 1H), 2.73-2.58 (m, 2H), 2.58-2.42 (m, 2H), 2.36-2.04 (m, 5H), 2.02-1.90 (m, 1H), 1.89-1.70 (m, 2H), 1.69-1.59 (m, 1H), 1.21-1.05 (m, 2H), 0.87-0.70 (m, 2H).

Example 13

(2R,3S)—N-((3S)-9-Chloro-2-oxo-5-phenyl-2,3-dihydro-1H-1,4-benzodiazepin-3-yl)-3-((3,3-difluorocyclobutyl)methyl)-2-(3,3,3-trifluoropropyl)succinamide

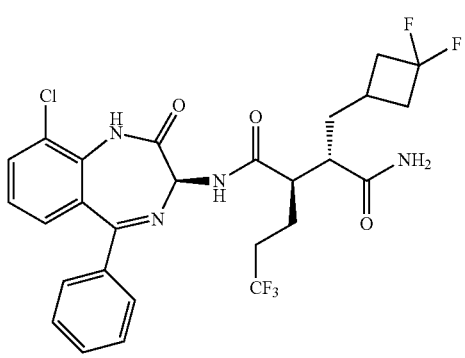

(13)

Example 13 was prepared from Intermediate B-3 and a 1.3:1 mixture of Intermediates S-1:S-1J according to the general procedure shown for Example 1. After separation of the diastereomers (Instrument: Berger SFC MGIII, Column: Chiral IC 25×3 cm ID, 5 μm; Mobile Phase: 80/20 CO₂/MeOH Flow rate: 85 mL/min; Detection at 220 nm), Example 13 was obtained. HPLC: RT=10.124 min (H₂O/CH₃CN with TFA, SunFire C18 3.5 μm, 4.6×150 mm, gradient=15 min, wavelength=220 and 254 nm); MS(ES): m/z=585.0 [M+H⁺]; $^1$H NMR (400 MHz, methanol-$d_4$) δ 7.79 (dd, J=7.7, 1.5 Hz, 1H), 7.63-7.50 (m, 3H), 7.48-7.40 (m, 2H), 7.36-7.24 (m, 2H), 5.42 (s, 1H), 2.78 (td, J=10.5, 4.1 Hz, 1H), 2.73-2.59 (m, 2H), 2.56-2.40 (m, 2H), 2.34-2.04 (m, 4H), 2.02-1.90 (m, 1H), 1.88-1.70 (m, 2H), 1.70-1.59 (m, 1H).

Example 14

(2R,3S)-3-((3,3-Difluorocyclobutyl)methyl)-N-((3S)-9-fluoro-2-oxo-5-phenyl-2,3-dihydro-1H-1,4-benzodiazepin-3-yl)-2-(3,3,3-trifluoropropyl)succinamide

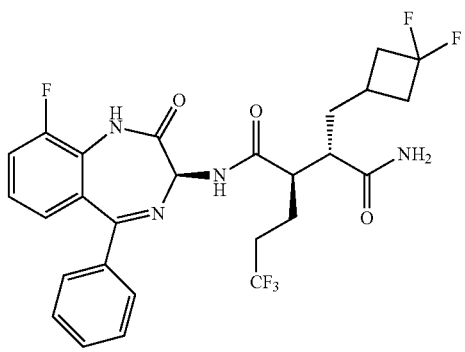

(14)

Example 14 was prepared from Intermediate B-5 and a 1.3:1 mixture of Intermediates S-1:S-1J according to the general procedure shown for Example 1. After separation of the diastereomers, (Instrument: Berger SFC MGIII, Column: Chiral IC 25×3 cm ID, 5 μm; Mobile Phase: 80/20 CO₂/MeOH Flow rate: 85 mL/min; Detection at 220 nm) Example 14 was obtained. HPLC: RT=7.770 min (H₂O/CH₃CN with TFA, SunFire C18 3.5 μm, 4.6×150 mm, gradient=15 min, wavelength=220 and 254 nm); MS(ES): m/z=569.2 [M+H⁺]; $^1$H NMR (400 MHz, methanol-$d_4$) δ 7.61-7.40 (m, 6H), 7.25 (td, J=8.0, 5.0 Hz, 1H), 7.20-7.15 (m, 1H), 5.43 (s, 1H), 2.83-2.57 (m, 3H), 2.56-2.38 (m, 2H), 2.35-2.04 (m, 4H), 2.03-1.92 (m, 1H), 1.89-1.62 (m, 3H).

Example 15

(2R,3S)-3-((3,3-Difluorocyclobutyl)methyl)-N-((3S)-2-oxo-5-phenyl-2,3-dihydro-1H-1,4-benzodiazepin-3-yl)-2-(3,3,3-trifluoropropyl)succinamide

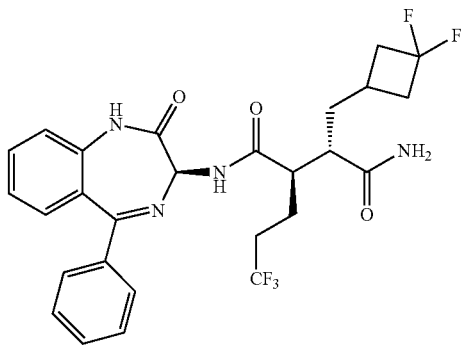

(15)

Example 15 was prepared from Intermediate B-12 and a 1.3:1 mixture of Intermediates S-1:S-1J according to the general procedure shown for Example 1. After separation of the diastereomers (Instrument: Berger SFC MGIII, Column: Chiral IC 25×3 cm ID, 5 μm; Mobile Phase: 80/20 $CO_2$/MeOH Flow rate: 85 mL/min; Detection at 220 nm), Example 15 was obtained. HPLC: RT=7.690 min ($H_2O$/$CH_3CN$ with TFA, SunFire C18 3.5 μm, 4.6×150 mm, gradient=15 min, wavelength=220 and 254 nm); MS(ES): m/z=551.3 [M+H$^+$]; $^1$H NMR (400 MHz, methanol-$d_4$) δ 7.64 (ddd, J=8.4, 7.3, 1.5 Hz, 1H), 7.59-7.49 (m, 3H), 7.47-7.40 (m, 2H), 7.36 (ddd, J=16.2, 8.1, 1.0 Hz, 2H), 7.30-7.23 (m, 1H), 5.41 (s, 1H), 2.82-2.58 (m, 3H), 2.55-2.40 (m, 2H), 2.34-2.04 (m, 4H), 2.03-1.91 (m, 1H), 1.89-1.61 (m, 3H).

Example 16

(2R,3S)-3-(3-Fluoropropyl)-N-((3S)-9-methoxy-2-oxo-5-phenyl-2,3-dihydro-1H-1,4-benzodiazepin-3-yl)-2-(3,3,3-trifluoropropyl)succinamide

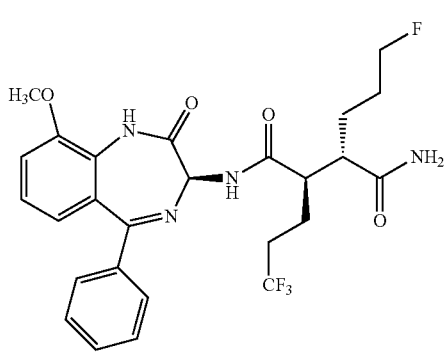

(16)

Example 16 was prepared from Intermediate B-2 and Intermediate S-6 according to the general procedure shown for Example 1. This solid was purified by preparative SFC chromatography (Berger SFC MGII, IC-H 250×21 mm ID, 5 μm, 75/25 $CO_2$/MeOH, 65 mL/min) to give Example 6. HPLC: RT=8.06 min ($H_2O$/$CH_3CN$ with TFA, SunFire C18 3.5 μm, 4.6×150 mm, gradient=15 min, wavelength=220 and 254 nm); MS(ES):m/z=537 [M+H$^+$]; $^1$H NMR (400 MHz, methanol-$d_4$) δ 10.07 (s, 1H), 9.43 (d, J=7.0 Hz, 1H), 7.60 (br. s., 1H), 7.57-7.50 (m, 3H), 7.50-7.43 (m, 2H), 7.36-7.30 (m, 1H), 7.28-7.22 (m, 1H), 7.02 (br. s., 1H), 6.88 (dd, J=7.8, 1.2 Hz, 1H), 5.22 (d, J=7.0 Hz, 1H), 4.45 (t, J=5.7 Hz, 1H), 4.33 (t, J=5.8 Hz, 1H), 3.94 (s, 3H), 2.81-2.70 (m, 1H), 2.61 (br. s., 1H), 2.48-2.37 (m, 2H), 2.31-2.18 (m, 1H), 1.69-1.48 (m, 5H).

Example 17

(2R,3S)-3-(3-Fluoropropyl)-N-((3S)-8-methoxy-2-oxo-5-phenyl-2,3-dihydro-1H-1,4-benzodiazepin-3-yl)-2-(3,3,3-trifluoropropyl)succinamide

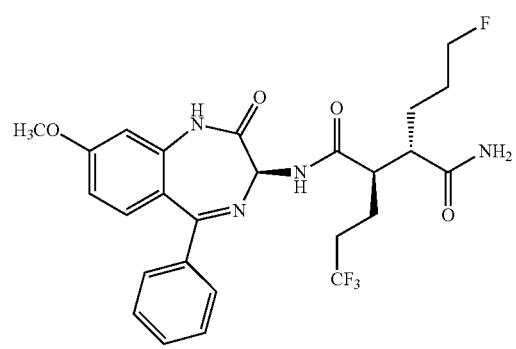

(17)

Example 17 was prepared from Intermediate B-10 and Intermediate S-6 according to the general procedure shown for Example 1. The diastereoisomers were purified by preparative SFC chromatography (Berger SFC MGII, Chiral IC 250×30 mm ID, 5 μm, 80/20 $CO_2$/MeOH, 85 mL/min) to give Example 17. HPLC: RT=7.95 min ($H_2O$/$CH_3CN$ with TFA, SunFire C18 3.5 μm, 4.6×150 mm, gradient=15 min, wavelength=220 and 254 nm); MS(ES):m/z=537.3 [M+H$^+$]; $^1$H NMR (400 MHz, DMSO-$d_6$) δ 10.76 (s, 1H), 9.43 (d, J=7.5 Hz, 1H), 7.61 (br. s., 1H), 7.56-7.49 (m, 3H), 7.47-7.41 (m, 2H), 7.23 (d, J=8.8 Hz, 1H), 7.05 (br. s., 1H), 6.88-6.83 (m, 1H), 6.81 (s, 1H), 5.23 (d, J=7.3 Hz, 2H), 4.44 (t, J=5.6 Hz, 2H), 4.33 (t, J=5.7 Hz, 2H), 3.85 (s, 3H), 2.78-2.57 (m, 2H), 2.47-2.38 (m, 1H), 2.30-2.15 (m, 1H), 1.68-1.56 (m, 3H).

Example 18

(2R,3S)-3-(2,2-Difluoropropyl)-N-((3S)-2-oxo-5-phenyl-2,3-dihydro-1H-1,4-benzodiazepin-3-yl)-2-(3,3,3-trifluoropropyl)succinamide

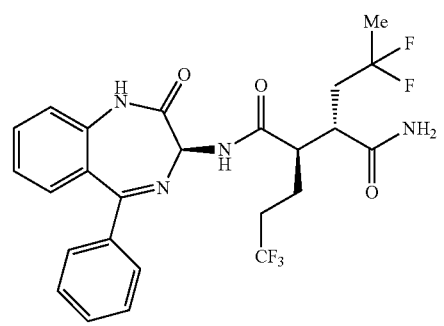

(18)

Example 18 was prepared from Intermediate B-12 and Intermediate S-4 according to the general procedure shown for Example 1. After separation of the diastereomers, (Berger SFC, Column: Chiral AD-H 25×3 cm, 5 mm; Mobile Phase: 80/20 $CO_2$/MeOH Flow rate: 80 mL/min;

Detection at 220 nm), Example 18 was obtained. MS(ES): m/z 525.1 [M+H+]. HPLC RT=0.85 min (BEH C18 2.1×50 mm, 1.7µ, 0 to 100 B in 1 min with 0.5 min hold time, Flow rate=1 ml/min, detection at 254 nm, Solvent A: 100% water 0.1% TFA; Solvent B: 100% ACN 0.1% TFA). $^1$H NMR (400 MHz, MeOD) δ ppm 7.58-7.66 (1H, m), 7.54 (3H, d, J=1.54 Hz), 7.41 (4H, s), 7.19-7.29 (1H, m), 5.39 (1H, s), 2.78-2.92 (1H, m), 2.64-2.78 (1H, m), 2.34-2.59 (2H, m), 2.13-2.31 (1H, m), 1.95-2.14 (1H, m), 1.73-1.92 (2H, m), 1.47-1.69 (3H, m).

Example 19

(2R,3S)—N-((3S)-9-Fluoro-2-oxo-5-phenyl-2,3-dihydro-1H-1,4-benzodiazepin-3-yl)-3-((2S)-3,3,3-trifluoro-2-methylpropyl)-2-(3,3,3-trifluoropropyl)succinamide (19)

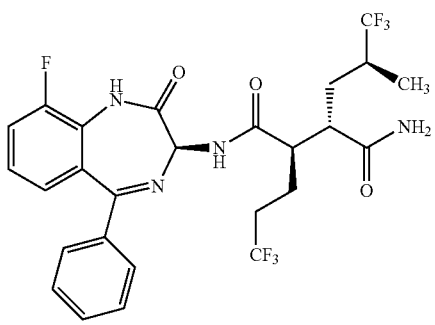

Example 19 was prepared from Intermediate B-13 and Intermediate S-5 according to the general procedure shown for Example 1. After separation of the diastereomers, (Berger SFC MGII, Column: CHIRALPAK® IC 25×3 cm, 5 mm; Mobile Phase: 90/10 CO$_2$/MeOH Flow rate: 85 mL/min; Detection at 220 nm), Example 19 was obtained. LC/MS, m/z 575.4 (M+1). HPLC RT=0.91 min. LC/MS (BEH C18 2.1×50 mm, 1.7µ, 0 to 100 B in 1 min with 0.5 min hold time, Flow rate=1 ml/min, detection at 254 nm, Solvent A: 100% water 0.1% TFA; Solvent B: 100% ACN 0.1% TFA). $^1$H NMR (400 MHz, methanol-d$_4$) δ 7.64-7.40 (m, 6H), 7.29 (d, J=4.8 Hz, 1H), 7.24-7.18 (m, 1H), 5.48 (s, 1H), 2.87-2.63 (m, 2H), 2.61-2.42 (m, 1H), 2.14 (s, 3H), 1.96-1.67 (m, 2H), 1.56-1.34 (m, 1H), 1.16 (d, J=6.8 Hz, 3H).

Example 20

(2R,3S)—N-((3S)-9-Chloro-2-oxo-5-phenyl-2,3-dihydro-1H-1,4-benzodiazepin-3-yl)-3-(3-fluoropropyl)-2-(3,3,3-trifluoropropyl)succinamide (20)

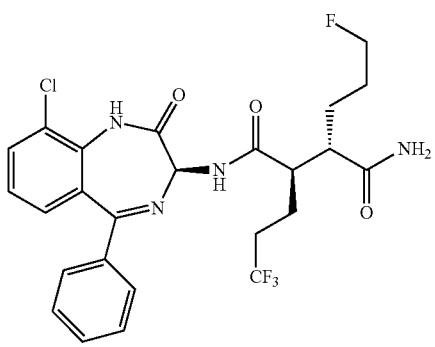

Example 20 was prepared from Intermediate B-3 and Intermediate S-6 according to the general procedure shown for Example 1. HPLC: RT=10.04 min (H$_2$O/CH$_3$CN with TFA, SunFire C18 3.5 µm, 4.6×150 mm, gradient=15 min, wavelength=220 and 254 nm); MS(ES):m/z=541.1 [M+H+]; $^1$H NMR (400 MHz, chloroform-d) δ 8.10 (s, 1H), 7.68 (dd, J=7.9, 1.3 Hz, 1H), 7.60 (d, J=5.9 Hz, 1H), 7.52-7.46 (m, 2H), 7.42-7.37 (m, 2H), 7.33 (dd, J=7.9, 1.3 Hz, 1H), 7.23-7.13 (m, 2H), 6.32 (br. s., 1H), 6.17 (br. s., 1H), 5.53 (d, J=7.5 Hz, 1H), 4.63-4.57 (m, 1H), 4.56-4.50 (m, 1H), 4.49-4.44 (m, 1H), 4.43-4.35 (m, 1H), 4.29 (d, J=3.3 Hz, 1H), 2.73-2.58 (m, 1H), 2.39-2.12 (m, 4H), 1.99-1.76 (m, 1H), 1.70-1.57 (m, 1H).

Example 21

(2R,3S)-3-((3,3-Difluorobutyl)-N-((3S)-9-methoxy-2-oxo-5-phenyl-2,3-dihydro-1H-1,4-benzodiazepin-3-yl)-2-(3,3,3-trifluoropropyl)succinamide (21)

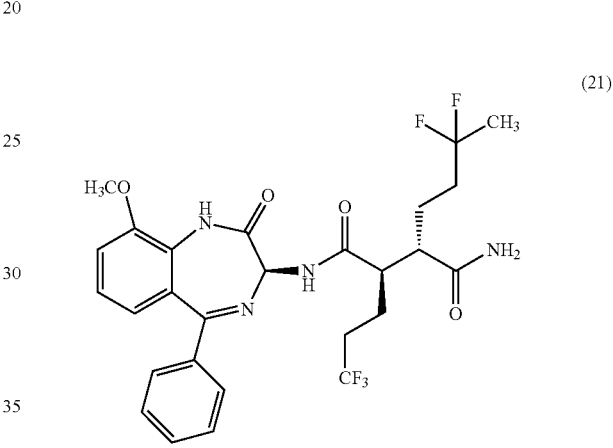

Example 21A (2S,3R)-tert-Butyl 2-(3,3-difluorobutyl)-6,6,6-trifluoro-3-((9-methoxy-2-oxo-5-phenyl-2,3-dihydro-1H-benzo[e][1,4]diazepin-3-yl)carbamoyl)hexanoate (21A)

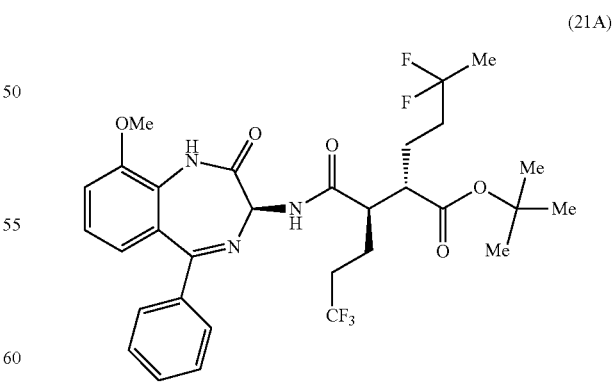

To a suspension of Intermediate B-2, 2 hydrobromide (66.0 mg, 0.149 mmol), Intermediate S-7 (53.0 mg, 0.146 mmol, and HOAt (8 mg, 0.06 mmol) in CH$_2$Cl$_2$ (3 mL) was added N-methylmorpholine (0.100 mL, 0.91 mmol) followed by EDC (40.0 mg, 0.209 mmol). The mixture was stirred at room temperature for 5 h, and purified by flash chromatography (SiO$_2$, 0% ethyl acetate/methylene chloride to 15% ethyl acetate/methylene chloride over 9 column volumes, 25 g column) to afford Example 21A (55.0 mg, 59.0%) which was used directly in the next step. HPLC: RT=4.28 min (H$_2$O/MeOH with TFA, PHENOMENEX® Luna, 2.0×50 mm, gradient=4 min, wavelength=254 nm) MS(ES):m/z=626 [M+H$^+$]; $^1$H NMR (500 MHz, chloroform-d) δ 8.02 (s, 1H), 7.56-7.52 (m, 2H), 7.49-7.45 (m, 1H), 7.42-7.33 (m, 2H), 7.19-7.14 (m, 1H), 7.11-7.06 (m, 1H), 6.98 (dd, J=7.9, 1.1 Hz, 1H), 6.97-6.85 (m, 1H), 5.56 (d, J=8.1 Hz, 1H), 3.99 (s, 3H), 2.71-2.56 (m, 2H), 2.38-2.18 (m, 2H), 2.02-1.74 (m, 6H), 1.62 (t, J=18.6 Hz, 3H), 1.53-1.50 (s, 9H).

Example 21

A solution of Example 21A (55.0 mg, 0.088 mmol) in DCM (10 mL) was treated with TFA (10 mL) and stirred at room temperature for 45 min. The solvent was evaporated, and then the residue was dissolved in DCM and evaporated again. After dilution with toluene and evaporation in vacuo, the resulting solid was dried under high vacuum for several hours. The residue was dissolved in THF (1.5 mL), and HOAT (52.0 mg, 0.382 mmol) was added and the mixture was stirred for 5 min. Then EDC (71.5 mg, 0.373 mmol) was added and stirring continued for an additional 1 min. 2N Ammonia in IPA (0.285 mL, 0.570 mmol) was then added and the reaction mixture was stirred at room temperature overnight. THF (8 mL) and CH$_2$Cl$_2$ (15 mL) were added, the reaction mixture was stirred for 5 min, and the solids were removed by filtration. The filtrate was evaporated and the crude product was dissolved in a small amount of methylene chloride and purified by flash chromatography (SiO$_2$, 0% ethyl acetate/methylene chloride to 50% ethyl acetate/methylene chloride over 10 column volumes, 25 g column) to afford the compound of Example 21 (34 mg, 68.1%): HPLC: 95/5 to 5/95 H$_2$O/CH$_3$CN/0.05% TFA, flow=1 mL/min, gradient=30 min: SunFire C18 3.5 µm, 3.0×150 mm: RT=16.24 min; MS(ES) m/z=569 [M+H]'; $^1$H NMR (500 MHz, chloroform-d) δ 8.07 (s, 1H), 7.56-7.44 (m, 4H), 7.42-7.35 (m, 2H), 7.20-7.14 (m, 1H), 7.11-7.07 (m, 1H), 6.98 (dd, J=8.0, 1.1 Hz, 1H), 5.98 (br. s., 1H), 5.57 (br. s., 1H), 5.55 (d, J=7.8 Hz, 1H), 3.99 (s, 3H), 2.71-2.58 (m, 2H), 2.36-2.14 (m, 2H), 2.02-1.80 (m, 6H), 1.63 (t, J=18.5 Hz, 3H).

Example 22

(2R,3S)—N-((3S)-9-Chloro-2-oxo-5-phenyl-2,3-dihydro-1H-1,4-benzodiazepin-3-yl)-3-((2R)-3,3,3-trifluoro-2-methylpropyl)-2-(3,3,3-trifluoropropyl)succinamide

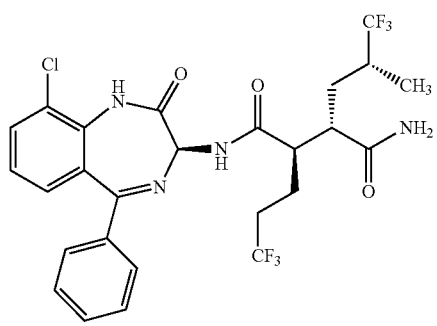

(22)

Example 22 was prepared from Intermediate B-3 and Intermediate S-5 according to the general procedure shown for Example 1. After separation of the diastereomers, (Berger SFC MGII, Column: CHIRALPAK® IC 25×3 cm, 5 mm; Mobile Phase: 90/10 CO$_2$/MeOH Flow rate: 85 mL/min; Detection at 220 nm), Example 22 was obtained. MS(ES), m/z 591.3 (M+H). HPLC RT=0.94 min. (BEH C18 2.1×50 mm, 1.7µ, 0 to 100 B in 1 min with 0.5 min hold time, Flow rate=1 ml/min, detection at 254 nm, Solvent A: 100% water 0.1% TFA; Solvent B: 100% ACN 0.1% TFA). $^1$H NMR (400 MHz, methanol-d$_4$) δ 7.82-7.76 (m, 1H), 7.63-7.50 (m, 3H), 7.45 (d, J=7.7 Hz, 2H), 7.37-7.26 (m, 2H), 5.41 (s, 1H), 2.80-2.64 (m, 2H), 2.60-2.37 (m, 1H), 2.34-2.12 (m, 2H), 2.03-1.66 (m, 4H), 1.16 (d, J=7.0 Hz, 3H).

Example 23

(2R,3S)—N-((3S)-9-Chloro-2-oxo-5-phenyl-2,3-dihydro-1H-1,4-benzodiazepin-3-yl)-3-((2S)-3,3,3-trifluoro-2-methylpropyl)-2-(3,3,3-trifluoropropyl)succinamide

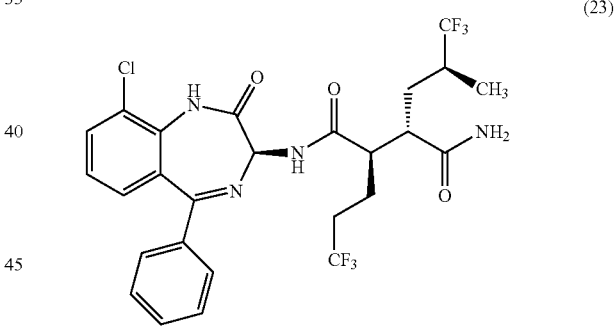

(23)

Example 23 was prepared from Intermediate B-3 and Intermediate S-5 according to the general procedure shown for Example 1. After separation of the diastereomers, (Berger SFC MGII, Column: CHIRALPAK® IC 25×3 cm, 5 mm; Mobile Phase: 90/10 CO$_2$/MeOH Flow rate: 85 mL/min; Detection at 220 nm), Example 23 was obtained. MS(ES), m/z 591.3 (M+H$^+$). HPLC RT=0.95 min. (BEH C18 2.1×50 mm, 1.7µ, 0 to 100 B in 1 min with 0.5 min hold time, Flow rate=1 ml/min, detection at 254 nm, Solvent A: 100% water 0.1% TFA; Solvent B: 100% ACN 0.1% TFA). $^1$H NMR (400 MHz, methanol-d$_4$) δ 7.79 (dd, J=7.9, 1.5 Hz, 1H), 7.65-7.57 (m, 2H), 7.53 (s, 1H), 7.45 (d, J=7.7 Hz, 2H), 7.35 (d, J=1.5 Hz, 1H), 7.30 (d, J=7.9 Hz, 1H), 5.43 (s, 1H), 2.85-2.64 (m, 2H), 2.60-2.43 (m, 1H), 2.35-2.08 (m, 3H), 1.96-1.73 (m, 2H), 1.51-1.39 (m, 1H), 1.15 (d, J=6.8 Hz, 3H).

Example 24

(2R,3S)—N-((3S)-9-Chloro-2-oxo-5-phenyl-2,3-dihydro-1H-1,4-benzodiazepin-3-yl)-3-(3,3-difluorobutyl)-2-(3,3,3-trifluoropropyl)succinamide

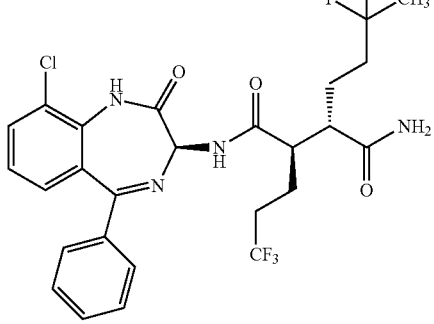

Example 24 was prepared from Intermediate B-3, 2 hydrobromide and Intermediate S-7 according to the general procedure shown for Example 21. The crude product was dissolved in a small amount of methylene chloride and purified by flash chromatography (SiO$_2$, 0% ethyl acetate/methylene chloride to 50% ethyl acetate/methylene chloride over 10 column volumes, 40 g column) to afford the compound of Example 24. HPLC: 95/5 to 5/95 H$_2$O/CH$_3$CN/0.05% TFA, flow=1 mL/min, gradient=30 min: SunFire C18 3.5 μm, 3.0×150 mm: RT=16.8 min. MS(ES) m/z=573 [M+H]$^+$; $^1$H NMR (500 MHz, chloroform-d) δ 8.16 (br. s., 1H), 7.74 (d, J=7.9 Hz, 1H), 7.68 (dd, J=7.9, 1.4 Hz, 1H), 7.55-7.47 (m, 3H), 7.43-7.37 (m, 2H), 7.34 (dd, J=7.9, 1.2 Hz, 1H), 7.20 (t, J=7.9 Hz, 1H), 5.99 (br. s., 1H), 5.69 (br. s., 1H), 5.55 (d, J=7.8 Hz, 1H), 2.80-2.71 (m, 1H), 2.66-2.56 (m, 1H), 2.32-2.13 (m, 2H), 2.03-1.80 (m, 6H), 1.61 (t, 3H, J=18.4 Hz).

Example 25

(2R,3S)-3-((1-Fluorocyclobutyl)methyl)-N-((3S)-9-methyl-2-oxo-5-phenyl-2,3-dihydro-1H-1,4-benzodiazepin-3-yl)-2-(3,3,3-trifluoropropyl)succinamide

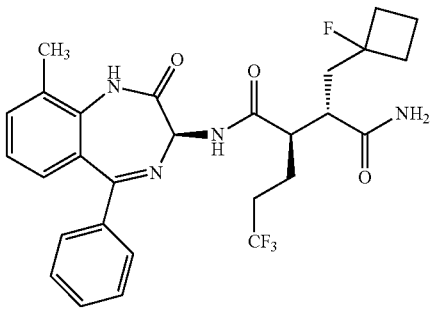

A solution of Intermediate B-1 (31.9 mg, 0.120 mmol), Intermediate S-2 (30 mg, 0.100 mmol), HOBT (30.7 mg, 0.200 mmol), and water (10.84 μl, 0.601 mmol) in THF (2 mL) was cooled in a salt ice-water bath and then treated with EDC (23.06 mg, 0.120 mmol). The mixture was stirred in a salt ice-water bath for 5.5 h, and then slowly warmed to room temperature overnight. The solvent was removed under a stream of nitrogen, and the residue was dissolved in DMF/MeOH, and purified by preparative reversed-phase HPLC (YMC ODS C18 5μ 20×100 mm, eluting with 40%-90% aqueous methanol over 15 minutes containing 0.1% TFA, 20 mL/min, monitor 254 nm). The desired fraction was concentrated, and then dried under vacuum to afford Example 25 (14 mg, 23%). HPLC: RT=7.750 min (H$_2$O/CH$_3$CN with TFA, SunFire C18 3.5 μm, 4.6×150 mm, gradient=15 min, wavelength=220 and 254 nm); MS(ES): m/z=547.4 [M+H$^+$]; $^1$H NMR (400 MHz, methanol-d$_4$) δ 7.61-7.55 (m, 2H), 7.54-7.47 (m, 2H), 7.46-7.39 (m, 2H), 7.26-7.19 (m, 1H), 7.06 (dd, J=7.9, 1.3 Hz, 1H), 5.36 (s, 1H), 3.61 (t, J=5.6 Hz, 2H), 3.45-3.36 (m, 5H), 3.26-3.13 (m, 2H), 3.10-2.89 (m, 4H), 2.89-2.77 (m, 3H), 2.38-1.72 (m, 12H).

Comparative Compounds 26 to 29

Comparative Compounds 26 to 29 can be prepared according to the procedures described in U.S. Pat. No. 7,053,084 for Examples 8, 12a, 38, and 45a, respectively.

TABLE 4

| Comparative Compound | U.S. Pat. No. 7,053,084 | Structure |
|---|---|---|
| 26 | Ex. 8 | 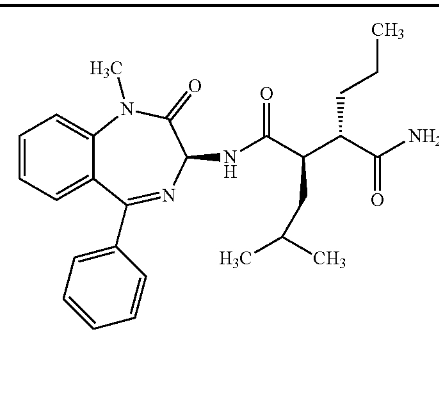 |

TABLE 4-continued

| Comparative Compound | U.S. Pat. No. 7,053,084 | Structure |
|---|---|---|
| 27 | Ex. 12a | 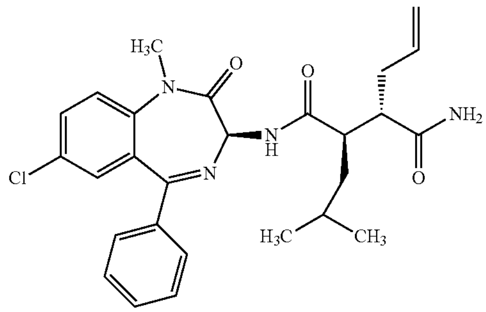 [SMILES: C=CC[C@H](C(N)=O)[C@@H](CC(C)C)C(=O)N[C@H]1N=C(c2ccccc2)c2cc(Cl)ccc2N(C)C1=O] |
| 28 | Ex. 38 | 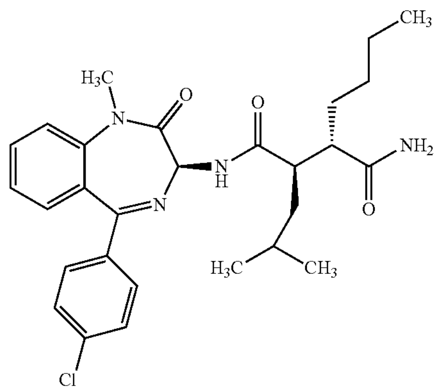 [SMILES: CCCC[C@H](C(N)=O)[C@@H](CC(C)C)C(=O)N[C@H]1N=C(c2ccc(Cl)cc2)c2ccccc2N(C)C1=O] |
| 29 | Ex. 45a | 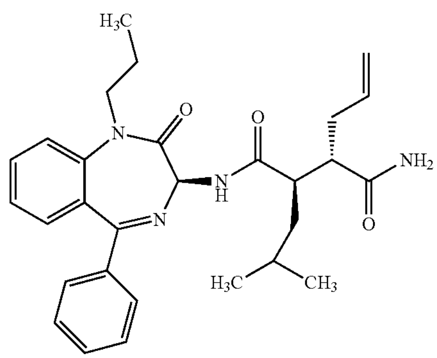 [SMILES: C=CC[C@H](C(N)=O)[C@@H](CC(C)C)C(=O)N[C@H]1N=C(c2ccccc2)c2ccccc2N(CCC)C1=O] |

Biological Assays

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask (4.5×10$^6$ cells/flask) using the Monster Transfection Kit (Minis #MIR$_{2906}$) according to manufacturers specifications. Table 5 denotes respective DNA quantity for the transfections.

TABLE 5

| | DNA (µg) | CBF1 (µg) | Vector (µg) | Total DNA (µg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of 5×10$^3$ cells/well in 95 µL assay media (DMEM (high glucose with HEPES), 1× glutamine/penicillin/streptomycin, 0.0125% BSA, 1× non-essential amino acids). Assay media (5 μL) containing test compounds in final concentrations ranging from 5 μM to 8.4× $10^{-5}$ μM (3 fold serial dilutions) were added to the cells and the cell plates were then incubated for 18 hours at 37° C. and 5% $CO_2$. Control wells contained DMSO vehicle (total counts) or 0.5 μM of an in-house small molecule inhibitor (background counts). Duplicates were used for each sample. Luciferase activity was measured after a 20-minute incubation with 50 μl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100×[1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 6 below lists the Notch 1 and Notch 3 $IC_{50}$ values for Examples 1-25 of this invention and Comparative Compounds 26-29 measured in the Notch-CBF1 Transactivation Assay hereinabove. In some instances, the value is an average of multiple experiments where N is the number of experiments conducted. The compounds of the present invention, as exemplified by the Examples 1-25 showed Notch 1 values of 14.0 nM or less and Notch 3 $IC_{50}$ values of 21.2 nM or less.

TABLE 6

| Example | Notch 1 ($IC_{50}$, nM) | N | Notch 3 ($IC_{50}$, nM) | N |
|---|---|---|---|---|
| 1 | 3.0 | 5 | 2.4 | 3 |
| 2 | 7.0 | 2 | 6.0 | 2 |
| 3 | 4.2 | 2 | 8.9 | 1 |
| 4 | 11.9 | 2 | 21.2 | 1 |
| 5 | 4.4 | 2 | 7.3 | 1 |
| 6 | 14.0 | 2 | 18.9 | 2 |
| 7 | 3.9 | 2 | 2.1 | 2 |
| 8 | 2.9 | 3 | 4.0 | 3 |
| 9 | 3.5 | 5 | 3.2 | 5 |
| 10 | 1.7 | 2 | 4.4 | 2 |
| 11 | 2.1 | 3 | 2.2 | 2 |
| 12 | 5.6 | 2 | 4.3 | 2 |
| 13 | 2.8 | 2 | 2.4 | 1 |
| 14 | 4.5 | 2 | 1.4 | 1 |
| 15 | 4.4 | 2 | 3.8 | 2 |
| 16 | 7.0 | 2 | 15.4 | 2 |
| 17 | 5.8 | 2 | 11.0 | 2 |
| 18 | 2.7 | 1 | 10.8 | 1 |
| 19 | 2.9 | 2 | 2.4 | 2 |
| 20 | 10.8 | 2 | 16.5 | 1 |
| 21 | 7.5 | 9 | 13.8 | 9 |
| 22 | 3.2 | 2 | 9.3 | 2 |
| 23 | 5.1 | 4 | 3.2 | 4 |
| 24 | 3.9 | 2 | 5.4 | 2 |
| 25 | 3.8 | 2 | 20.1 | 2 |
| Comparative Compound 26 | 64.1 | 1 | 48.3 | 1 |
| Comparative Compound 27 | 42.4 | 2 | 74.5 | 2 |
| Comparative Compound 28 | 5.1 | 3 | 13.5 | 4 |
| Comparative Compound 29 | 12.3 | 1 | 12.5 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 7.

TABLE 7

Metabolic Stability - Result Interpretation Guidelines

| CYP-Mediated Clearance | Percent Remaining after 10 minutes | | | | |
|---|---|---|---|---|---|
| | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials

Incubation with Liver Microsomes

Test compound was received as a 3.5 mM stock solution in 100 percent DMSO. The test compound was diluted to create a 50 μM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 μl of liver microsome suspension, protein concentration of 1.1 mg/ml in 100 mM $NaP_i$, pH 7.4, 5 mM $MgCl_2$ buffer, was pre-warmed at 37° C.

2. 1.7 μl of 50 μM compound (98.6% ACN, 1.4% DMSO) was added to the same tube and pre-incubated at 37° C. for 5 minutes.

3. The reaction was initiated by the addition of 17 μl of pre-warmed 10 mM NADPH solution in 100 mM $NaP_i$, pH 7.4.

The reaction components were mixed well, and 75 μl of the reaction mixture was immediately transferred into 150 μl quench/stop solution (zero-time point, $T_0$). Reactions were incubated at 37° C. for 10 minutes and then an additional 75 μl aliquot was transferred into 150 μl quench solution. Acetonitrile containing 100 μM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 8

Metabolic Stability Assay - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-H$_2$O. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 9

Metabolic Stability - Structural Integrity Gradient

| Gradient Time (min) | A % | B % |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 10

Metabolic Stability - Sample Analysis Gradient

| Gradient Time (min) | A % (or C %) | B % (or D %) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10minute}$ samples to those from the $T_{0minute}$ samples for each compound.

Quality Control

A set of three compounds was tested along with the test compound in each assay plate. Data was accepted and uploaded only if the results for these control compounds fall into the expected ranges shown below.

TABLE 11

Metabolic Stability Assay - Control Compound Values by Microsome Species

| Compound | Average Percent Remaining ± SD | | | | |
|---|---|---|---|---|---|
| | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al, 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 12

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the percent of parent compound that was remaining in the mixture.

TABLE 13

Metabolic Stability Half-Life Assays - Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 µM DMN) | 130 µl |
| Sample of Reaction | 65 µl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Table 14 below lists the CYP-mediated metabolic half life value for Examples 1-25 of this invention and Comparative Compounds 26-29 measured in the human metabolic stability half-life assay. In some instances, the value is an average of multiple experiments where N is the number of experiments conducted. The compounds of the present invention, as exemplified by Examples 1-25 had metabolic stability half life values of 33 minutes or longer. In contrast, Comparative Compounds 26-29 had metabolic stability half life values of 8 minutes or less.

TABLE 14

| Example | HLM ($t_{1/2}$, min) | N |
|---|---|---|
| 1 | 60 | 3 |
| 2 | 43 | 1 |
| 3 | 80 | 1 |
| 4 | >120 | 1 |
| 5 | 72 | 2 |
| 6 | >120 | 1 |
| 7 | >120 | 1 |
| 8 | 58 | 4 |
| 9 | 91 | 4 |
| 10 | 69 | 2 |
| 11 | 46 | 2 |
| 12 | 41 | 3 |
| 13 | >120 | 1 |
| 14 | >120 | 1 |
| 15 | 35 | 2 |
| 16 | 88 | 2 |
| 17 | >120 | 1 |
| 18 | >120 | 1 |
| 19 | 80 | 1 |
| 20 | 107 | 1 |
| 21 | 76 | 3 |
| 22 | 117 | 2 |
| 23 | 111 | 2 |
| 24 | >120 | 1 |
| 25 | 33 | 1 |
| Comparative Compound 26 | 8 | 1 |
| Comparative Compound 27 | 6 | 1 |
| Comparative Compound 28 | 6 | 1 |
| Comparative Compound 29 | 3 | 1 |

The exemplified compounds of the invention showed the surprising advantage of low clearance due to CYP-mediated metabolism in the human metabolic stability half life assay. The compounds of the present invention, as exemplified by Examples 1-25, had metabolic half lives in the range of 33 minutes or longer in the human metabolic stability half life assay. In contrast, Comparative Compounds 26-29 had metabolic stability half life values of 8 minutes or less in the human metabolic stability assay. Comparative Compounds 26-29 showed high clearance in the human metabolic stability assay, indicating that the compounds were removed by liver microsomes.

The compounds of the present invention (Examples 1-25) have been compared to the Comparative Compounds 26-29 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 6 and 14, in the reported tests, Examples 1-25 of this invention had Notch 1 $IC_{50}$ values of 14.0 nM or less and Notch 3 $IC_{50}$ values of 21.2 nM or less; and human metabolic stability half lives of 33 minutes or longer in the human metabolic stability half life assay. In contrast, in similar tests, Comparative Compounds 26-29 had Notch 1 $IC_{50}$ values of in the range of from 5.1 nM to 64.1 nM and Notch 3 $IC_{50}$ values in the range of 12.5 nM to 74.5 nM; and human metabolic stability half lives of 8 minutes or less.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromised balb/c nu/nu nude or NOD-SCID mice (Harlan Sprague Dawley). Tumors were propagated as subcutaneous transplants in the appropriate mouse strain (Table 15) using tumor fragments obtained from donor mice.

TABLE 15

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| HPB-ALL | ALL | NOD-SCID | female |
| ALL-SIL | ALL | NOD-SCID | female |
| MDA-MB-157 | breast | NOD-SCID | female |
| MDA-MB-468 | breast | NOD-SCID | female |
| PAT-34 | ovarian | nude | female |
| PAT-50 | ovarian | nude | female |
| PAT-26 | pancreas | nude | female |
| PAT-27 | pancreas | nude | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 15) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

Tumor weight=(length×width)÷2

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where, $C_t$=Median control tumor size at end of treatment $C_0$=Median control tumor size at treatment initiation $T_t$=Median tumor size of treated group at end of treatment $T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. The following excipients were used for administration of the Notch inhibitors to rodents: ETOH/TPGS/PEG300 (10:10:80). Notch inhibitors were typically administered orally on a schedule of QD×15, 10 day-on-2 day-off-5 day-on, although other schedules had also been evaluated and shown to be efficacious. For example, dosing regimen consisting of QD×12, 4 day-on-3 day-off was shown to be equally efficacious as QD×15, 10 day-on-2 day-off-5 day-on. In the BID studies, the second dose was given 6 to 12 hours after the first dose.

In Vivo Antitumor Activity

Table 16 below lists the antitumor activity of examples of this invention measured in the Human Tumor Xenograft Models in mice. The compounds of the present invention, as exemplified by Examples 1, showed antitumor activity with oral administration (PO).

TABLE 16

| Oral Administration | | |
|---|---|---|
| Example | Dose | Antitumor Activity in TALL-1 (LCK) BID dosing |
| 1 | 10 | 2.7 |

Schedule: BIDx10;
BID—twice daily;
LCK—Log Cell Kill

What is claimed is:

1. A compound of Formula (I):

wherein:

$R_1$ is —CH$_2$CH$_2$CF$_3$;

$R_2$ is —CH$_2$CH$_2$CH$_2$F, —CH$_2$CF$_2$CH$_3$, —CH$_2$CH(CH$_3$)CF$_3$, —CH$_2$CH$_2$CF$_2$CH$_3$, $R_3$ is H or —CH$_3$;

Ring A is phenyl or pyridinyl;

each $R_a$ is independently F, Cl, —CN, —OH, —CH$_3$, cyclopropyl, —CF$_3$, —OCH$_3$, —OCF$_3$, and/or —O(cyclopropyl);

each $R_b$ is independently F, Cl, —CH$_3$, —CF$_3$, —CN, and/or —OCH$_3$;

y is zero, 1, or 2; and z is zero, 1, or 2.

2. The compound according to claim 1 wherein:

$R_3$ is H;

Ring A is phenyl;

each $R_a$ is independently F, Cl, —CH$_3$, cyclopropyl, —OCH$_3$, and/or —O(cyclopropyl);

$R_b$ is F or —CH$_3$;

y is zero, 1, or 2; and z is zero or 1.

3. The compound according to claim 1 wherein:

Ring A is phenyl.

4. The compound according to claim 1 wherein:
R₂ is:

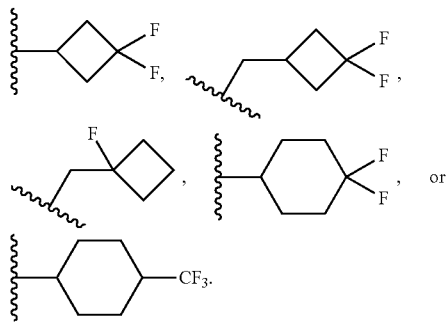

5. The compound according to claim 1 wherein:
R₂ is —CH₂CH₂CH₂F, —CH₂CH(CH₃)CF₃, or —CH₂CH₂CF₂CH₃.

6. A compound according to claim 1 selected from: (2R,3S)-3-((3,3-difluorocyclobutyl) methyl)-N-((3S)-9-methyl-2-oxo-5-phenyl-2,3-dihydro-1H-1,4-benzodiazepin-3-yl)-2-(3,3,3-trifluoropropyl)succinamide (1); (2R,3S)-3-(4,4-difluorocyclohexyl)-N-((3S)-9-methoxy-2-oxo-5-phenyl-2,3-dihydro-1H-1,4-benzodiazepin-3-yl)-2-(3,3,3-trifluoropropyl)succinamide (2); (2R,3S)—N-((3S)-9-(cyclopropyloxy)-5-(3-fluorophenyl)-2-oxo-2,3-dihydro-1H-1,4-benzodiazepin-3-yl)-3-(4,4-difluorocyclohexyl)-2-(3,3,3-trifluoropropyl)succinamide (3); (2R,3S)—N-((3S)-9-chloro-2-oxo-5-phenyl-2,3-dihydro-1H-1,4-benzodiazepin-3-yl)-3-(4-(trifluoromethyl)cyclohexyl)-2-(3,3,3-trifluoropropyl)succinamide (4); (2R,3S)—N-((3S)-9-chloro-2-oxo-5-phenyl-2,3-dihydro-1H-1,4-benzodiazepin-3-yl)-3-(4,4-difluorocyclohexyl)-2-(3,3,3-trifluoropropyl)succinamide (5); (2R,3S)-3-((3,3-difluorocyclobutyl)-N-((3S)-2-oxo-5-phenyl-2,3-dihydro-1H-1,4-benzodiazepin-3-yl)-2-(3,3,3-trifluoropropyl) succinamide (6); (2R,3S)—N-((3S)-9-(cyclopropyloxy)-2-oxo-5-phenyl-2,3-dihydro-1H-1,4-benzodiazepin-3-yl)-3-((3,3-difluorocyclobutyl)methyl)-2-(3,3,3-trifluoropropyl) succinamide (7); (2R,3S)-3-((3,3-difluorocyclobutyl) methyl)-N-((3S)-9-methoxy-2-oxo-5-phenyl-2,3-dihydro-1H-1,4-benzodiazepin-3-yl)-2-(3,3,3-trifluoropropyl)succinamide (8); (2R,3S)-3-((3,3-difluorocyclobutyl)methyl)-N-((3S)-5-(3-fluorophenyl)-9-methyl-2-oxo-2,3-dihydro-1H-1,4-benzodiazepin-3-yl)-2-(3,3,3-trifluoropropyl) succinamide (9); (2R,3S)—N-((3S)-9-chloro-5-(3-methylphenyl)-2-oxo-2,3-dihydro-1H-1,4-benzodiazepin-3-yl)-3-((3,3-difluorocyclobutyl)methyl)-2-(3,3,3-trifluoropropyl)succinamide (10); (2R,3S)-3-((3,3-difluorocyclobutyl)methyl)-N-((3S)-9-fluoro-5-(3-methylphenyl)-2-oxo-2,3-dihydro-1H-1,4-benzodiazepin-3-yl)-2-(3,3,3-trifluoropropyl) succinamide (11); (2R,3S)—N-((3S)-9-cyclopropyl-2-oxo-5-phenyl-2,3-dihydro-1H-1,4-benzodiazepin-3-yl)-3-((3,3-difluorocyclobutyl)methyl)-2-(3,3,3-trifluoropropyl)succinamide (12); (2R,3S)—N-((3S)-9-chloro-2-oxo-5-phenyl-2,3-dihydro-1H-1,4-benzodiazepin-3-yl)-3-((3,3-difluorocyclobutyl)methyl)-2-(3,3,3-trifluoropropyl)succinamide (13); (2R,3S)-3-((3,3-difluorocyclobutyl)methyl)-N-((3S)-9-fluoro-2-oxo-5-phenyl-2,3-dihydro-1H-1,4-benzodiazepin-3-yl)-2-(3,3,3-trifluoropropyl)succinamide (14); (2R,3S)-3-((3,3-difluorocyclobutyl)methyl)-N-((3S)-2-oxo-5-phenyl-2,3-dihydro-1H-1,4-benzodiazepin-3-yl)-2-(3,3,3-trifluoropropyl)succinamide (15); (2R,3S)-3-(3-fluoropropyl)-N-((3S)-9-methoxy-2-oxo-5-phenyl-2,3-dihydro-1H-1,4-benzodiazepin-3-yl)-2-(3,3,3-trifluoropropyl)succinamide (16); (2R,3S)-3-(3-fluoropropyl)-N-((3S)-8-methoxy-2-oxo-5-phenyl-2,3-dihydro-1H-1,4-benzodiazepin-3-yl)-2-(3,3,3-trifluoropropyl)succinamide (17); (2R,3S)-3-(2,2-difluoropropyl)-N-((3S)-2-oxo-5-phenyl-2,3-dihydro-1H-1,4-benzodiazepin-3-yl)-2-(3,3,3-trifluoropropyl)succinamide (18); (2R,3S)—N-((3S)-9-fluoro-2-oxo-5-phenyl-2,3-dihydro-1H-1,4-benzodiazepin-3-yl)-3-((2S)-3,3,3-trifluoro-2-methylpropyl)-2-(3,3,3-trifluoropropyl) succinamide (19); (2R,3S)—N-((3S)-9-chloro-2-oxo-5-phenyl-2,3-dihydro-1H-1,4-benzodiazepin-3-yl)-3-(3-fluoropropyl)-2-(3,3,3-trifluoropropyl)succinamide (20); (2R,3S)-3-(3,3-difluorobutyl)-N-((3S)-9-methoxy-2-oxo-5-phenyl-2,3-dihydro-1H-1,4-benzodiazepin-3-yl)-2-(3,3,3-trifluoropropyl) succinamide (21); (2R,3S)—N-((3S)-9-chloro-2-oxo-5-phenyl-2,3-dihydro-1H-1,4-benzodiazepin-3-yl)-3-((2R)-3,3,3-trifluoro-2-methylpropyl)-2-(3,3,3-trifluoropropyl)succinamide (22); (2R,3S)—N-((3S)-9-chloro-2-oxo-5-phenyl-2,3-dihydro-1H-1,4-benzodiazepin-3-yl)-3-((2S)-3,3,3-trifluoro-2-methylpropyl)-2-(3,3,3-trifluoropropyl) succinamide (23); (2R,3S)—N-((3S)-9-chloro-2-oxo-5-phenyl-2,3-dihydro-1H-1,4-benzodiazepin-3-yl)-3-(3,3-difluorobutyl)-2-(3,3,3-trifluoropropyl)succinamide (24); and (2R,3S)-3-((1-fluorocyclobutyl)methyl)-N-((3S)-9-methyl-2-oxo-5-phenyl-2,3-dihydro-1H-1,4-benzodiazepin-3-yl)-2-(3,3,3-trifluoropropyl)succinamide (25).

7. A pharmaceutical composition comprising at least one compound according claim 1; and a pharmaceutically acceptable carrier.

* * * * *